(12) United States Patent
Oard

(10) Patent No.: US 10,988,740 B2
(45) Date of Patent: Apr. 27, 2021

(54) DEVELOPMENT OF MICROORGANISMS FOR HYDROGEN PRODUCTION

(71) Applicant: Svetlana Oard, Baton Rouge, LA (US)

(72) Inventor: Svetlana Oard, Baton Rouge, LA (US)

(73) Assignee: Svetlana Oard, Baton Rouge, LA (US)

( * ) Notice: Subject to any disclaimer, the term of this patent is extended or adjusted under 35 U.S.C. 154(b) by 100 days.

(21) Appl. No.: 14/542,291

(22) Filed: Nov. 14, 2014

(65) Prior Publication Data

US 2015/0140592 A1 May 21, 2015

Related U.S. Application Data

(60) Provisional application No. 61/905,010, filed on Nov. 15, 2013.

(51) Int. Cl.
| | |
|---|---|
| *C12N 1/20* | (2006.01) |
| *C12N 1/12* | (2006.01) |
| *C12N 15/67* | (2006.01) |
| *C12N 9/02* | (2006.01) |
| *C12P 3/00* | (2006.01) |
| *C12N 15/82* | (2006.01) |
| *C12Q 1/26* | (2006.01) |

(52) U.S. Cl.
CPC ....... *C12N 9/0067* (2013.01); *C12N 15/8243* (2013.01); *C12P 3/00* (2013.01); *C12Q 1/26* (2013.01); *C12Y 112/07002* (2013.01)

(58) Field of Classification Search
CPC .. C12N 9/02; C12N 1/12; C12N 15/74; C12P 3/00; C12P 21/06
See application file for complete search history.

(56) References Cited

U.S. PATENT DOCUMENTS

| | | | |
|---|---|---|---|
| 7,135,290 B2* | 11/2006 | Dillon | C12N 9/0004 435/6.13 |
| 2006/0228774 A1* | 10/2006 | King | C12N 9/001 435/69.1 |
| 2007/0009942 A1* | 1/2007 | Dillon | C12N 9/0004 435/6.13 |
| 2010/0041121 A1* | 2/2010 | Wang | C12N 9/0067 435/168 |

OTHER PUBLICATIONS

Fouchard et al., Biotechnol. Bioeng., 102(1), 232-245, 2008.*

* cited by examiner

*Primary Examiner* — Maryam Monshipouri
(74) *Attorney, Agent, or Firm* — Svetlana Oard

(57) ABSTRACT

Methods and compositions are provided for engineering microorganisms, which permit enhanced $H_2$ production. The methods and compositions provided include novel chimeric gene constructs encoding $H_2$-forming $H_2$ase and maturation proteins, allowing for generation of $H_2$ continuously in large quantities. In one illustrated embodiment, novel engineered algae are provided with increased levels of $H_2$ production.

9 Claims, 17 Drawing Sheets
Specification includes a Sequence Listing.

pX-HydA pX-HydG pX-HydEF pCh-HydA1:       *5'RbcS2-SP-petF-hydA1m-3'RbcS2*   in pChlamy_1
pCh-HydA1-HydG:  *5'RbcS2-SP-petF-hydA1m-3'RbcS2*   and
                 *5'Cyc6-SP-crgfp-hydGm-3'Cyc6*   in pChlamy_1
pJR-HydEF:       *5'Cyc6-SP-hydEFm-3'Cyc6*   in pJR38

*FIG. 2*

HydA1 (genomic) (SEQ ID NO:1)
TCTTACATGAACACACAAACACTCTCGCAGGCACTAGCCTCAAACCCTCGAAACCTT
TTTCCAACAGTTTACACCCCAATTCGGACGCCGCTCCAAGCTCGCTCCGTTGCTCCTT
CATCGCACCACCTATTATTTCTAATATCGTAGACGCGACAAGATGTCGGCGCTCGTG
CTGAAGCCCTGCGCGGCCGTGTCTATTCGCGGCAGCTCCTGCAGGGCGCGGCAGGTC
GCCCCCGCGCTCCGCTCGCAGCCAGCACCGTGCGTGTAGCCCTTGCAACACTTGAG
GCGCCCGCACGCCGCCTAGGTGAGGGCGACGCAGTGAACGCAGTTTCGATGGGTCA
CTTTGTCGCTTTTGCGGAAGCCTCCGAAACGTCCCGCGAGGTTCAAACGGCCCCGAA
TGACCACACCCATATGGCCACTGGAAATAATAACGCAGGCAACGTCGCTTGCGCGG
CTGCCGCACCCGCTGCGGAGGCGCCTTTGAGTCATGTCCAGCAGGCGCTCGCCGAGC
TTGGTGAGCGAACGGCCGAGCGAGCGCGCACGCATTGTTGTGGTCAAGTCTCTCCAC
TCAGTCCGACCCCCACACGGCGTAGGGGTCTGAAGTCCACCAACTCCTCACACACC
CCAAGGAAGGGACGTAAGCCCCCTGGCTACGCTTTACCCAGCAGCCACAGCGACA
GAGCGCCCCAACATAGGCTCGAGATAGAACGCACCTGAACTGTGACACTTACAATG
GAAAGGAACTGCGGATGGCCTTAAAGTCAA GCATTTTGTGACGAGTCGGCTCGGAA
TCCCCATCGGCGCCCGTCCGTTCGTCTTCATCACCGCCTGAAACGGCGCACGCGCAA
TAGTGCGCACTTGATGCCTTTCGGTCCAACGCCTCTGTCAGCTAACACTTTCCAGGG
CCAGCGCGGACTCGAGAACCCTCTTTCCTGGCAACCTTGGTTTGGCTGGCACCTGGC
AACCTTGGTTTGGCTGGCACCAACCTTGACCCACATAAATCTCTCCCCCCCCCCTTA
TGCCCACAGCCAAGCCCAAGGACGACCCCACGCGCAAGCACGTCTGCGTGCAGGTG
GCTCCGGCCGTTCGTGTCGCTATTGCCGAGACCCTGGGCCTGGCGCCGGGCGCCACC
ACCCCCAAGCAGCTGGCCGAGGGCCTCCGCCGCCTCGGCTTTGACGAGGTAGGTGC
GCTCGCTGCTGCAGTGCCCAACACGCATCTTCCAGCTCACCGCCTACCAGTCAGCAC
CTTGGCATGCATGCTTGGCGCATCTGCCGCC TCATTGCCGCCTCGCGGCCTCGCCGC
TGCCTGCATCAAGCCTGCCTGCCTGCCTGCCCGCCCTCACGCCCAGGTGTTTGACAC
GCTGTTTGGCGCCGACCTGACCATCATGGAGGAGGGCAGCGAGCTGCTGCACCGCC
TCACCGAGCACCTGGAGGCCCACCCGCACTCCGACGAGCCGCTGCCCATGTTCACCA
GCTGCTGCCCCGGCTGGATCGGTGAGCAGCGCGGCGTGCTTGCTTAGGGCCCCATAA
CCTGTCTTGGGCCCCCGCGTCCGCCTCTCCACCTACCTGCAACATGTACGTGCCTAC
GGTATTGTCGCATGTCTCTTGACGATTTGGGTCGACCTTACCTTTGCCTTGTGTCCTT
TCTCCACCCCCACCCGCCTCTTTCCTCGCCGGCCCCCTCGCGCAGCTATGCTGGAG
AAATCTTACCCGGACCTGATCCCCTACGTGAGCAGCTGCAAGAGCCCCCAGATGAT
GCTGGCGGCCATGGTCAAGTCCTACCTAGC GGAAAAGAAGGGCATCGCGCCAAAGG
ACATGGTCATGGTGTCCATCATGCCCTGGTGAGAGCCCCGGGGGGGAGGCGGGGAT
TGCGGGGGGCAGGGGGTGCGGGGGGCAGGGTTTGCCGGCGTGGTGGAAGGCTGCCC
CAGGATGGTCGAGGAGCCCGCCGTGGGGGTCTGCCGGCGTAAAATTTGGTATGTG
GGTCGAATGGTTCAGCCGCGGAGCCATGGCGCCGCCCTGCACCAGCATTCAAGCT
GCCTGTGCTGACCCAACCCACCTGCTTCACCGCCCTGCACACACCGGTGCGCAGCAC
GCGCAAGCAGTCGGAGGCTGACCGCGACTGGTTCTGTGTGGACGCCGACCCCACCC
TGCGCCAGCTGGACCACGTCATCACCACCGTGGAGCTGGGCAACATCTTCAAGGTG
GGCCGGGGGCGGGGGGCGGGCGCGCGGGGCGTTATGATTCGGGCCTTAAGGGTTG
TTCGCATCATCATCAGAAAGCCCACCCAGCGCGGAAA TGCGAGTCGAACGCGAGTA
GGAGTAGTAGTACTCCTCGCTCTCTGGCACTGCTGTAAGCGCACACGCGCACCCACA
CGCACACGCACACGCACACGCAACCGCACACGTGCACCAACGTCACATCCACACGC

*FIG. 7A*

```
AGGAGCGCGGCATCAACCTGGCCGAGCTGCCCGAGGGCGAGTGGGACAATCCAATG
GGCGTGGGCTCGGGCGCCGGCGTGCTGTTCGGCACCACCGGCGGTGTCATGGAGGC
GGCGCTGCGCACGGTGGGTCTGTGAGAGCCGGTTGATTGGCCCGGCAGAACGCATA
CACTTGCTGAACCTTTGATGCGGGATAAGCAAGGCTACCGATCCGCGTCTTTTTACA
CCTGTTTATCACGTCGCTGAGCAAGCTCGTGACACCTGCAGGCCTATGAGCTGTTCA
CGGGCACGCCGCTGCCGCGCCTGAGCCTGAGCGAGGTGCGCGGCATGGACGGCATC
AAGGAGACCAACATCACCATGGTGCCCGCGCCCGGGTCCAAG TTTGAGGAGCTGCT
GAAGCACCGCGCCGCCGCGCGCCGAGGCCGCCGCGCACGGCACCCCCGGGCCGC
TGGCCTGGGACGGCGGCGCGGGCTTCACCAGCGAGGACGGCAGGGGCGGCATCACA
CTGCGCGTGGCCGTGGCCAACGGGCTGGGCAACGCCAAGAAGCTGATCACCAAGAT
GCAGGCCGGCGAGGCCAAGTACGACTTTGTGGAGATCATGGCCTGCCCCGCGGGCT
GTGTGGGCGGCGGCGGCCAGCCCCGCTCCACCGACAAGGCCATCACGCAGAAGCGG
CAGGCGGCGCTGTACAACCTGGACGAGAAGTGAGCGGGCGGCGCTGCTGGGATTGG
GCAGGGGAGGGAAGGGACTGCGGGGCAGGGTGCGGCGGGAAACGGAAATGGGCAA
GGCTCGAGGTGGAGGGCGGGGTGGGTTGGGGTTACTTGCTACAGGTTGGCGGGCAG
GATGTGATGGAAGCAGTGTGGAGGAGGTGTGCGTAGGGTCCCGACGACGGT ATTCG
CACGAGCAAAGAGGGTCGGCACTTCCTGACACAATGTGCGCCTGCACGTGCGCTCC
TGTTGCTGCCCCAGGTCCACGCTGCGCCGCAGCCACGAGAACCCGTCCATCCGCGAG
CTGTACGACACGTACCTCGGAGAGCCGCTGGGCCACAAGGTGGGGGGGGGTTGTAA
CTACCAGCCCAAATGACGGGGCTGGTCGGGGGCGTTGGAGAGGCGGGCCGGGAGG
GAGGCGGGCTGGGTGTGGGCAACAGCAGGTGAAGGGACGGGGGGGCACACTGGG
CAGGGCGGTACATGCCTTGTCCTGATAGCTACCCACACGCGACTGTTGCTACATGGA
TGCATGACGTGTGCCGTGTGCTTGACCCCTGCAGGCGCACGAGCTGCTGCACACCCA
CTACGTGGCCGGCGGCGTGGAGGAGAAGGACGAGAAGAAGTGAGGAGCGCCAGAG
GCTCTTTGGGCGGAGACAGCTTCAAAGCGAGGGGGCGTATTAGCAGTACCGTAAAT
ATGCACTGATGGGTGATGCGGGTGTCCTCCTTTATATTGAATGGGGTCAAAATAGGC
GGCGGGTCAAATGTTTCCTTTTTGAGTGGTGTCACAGCATGGGGCACGTGTGCGGAG
GCCAGTTGCCCTCCAGTGCACGCGCTCCCGGTGTGTGGCCGCACTGGCCTTGGATAA
TGCACCGGTGGAGGATTATGGAAGAGGGGACTCAGAAGGCTCATTATTGGACAAT
GCCTGGTCTCTTCCACATTGGTGTGAGCGCGGCTCCGCATAGGCTGTTCACTGCACG
CTGGCATTAGGCGTAGGTACTGGCATGAGGGAGCGCGGCTTGCTAACCGAATGGCG
TATCCCTCCAGGGCACGTCGGAATGGCGCGTGCCCATCAACGCAAATTCTTGGCCTT
CATCGCTTCTGGATATTGAAGCTGCACAAACCTGCATTCTATTTGCTTGTTTACACGT
GCCCCAATCTTGGTTGGAAGCTAAACATGTTTGGGAACAATTCATCTTACTAAAGCG
TGTGGGGGTTGAGGATGCGCACGTTGTGCGCTGGTGGTGGGCGGGAACGTGGGTA
GCATTTAGGCTAGCTGGCATACGACAACGGGGCCCGTGAGGATTGAGCACTTGACT
CGCGAACTTATGAACGTAGCGCTTTATACCCACCGTATGCGATTGACGTTGGTGTAG
GCAACCAGGCGGTAGGAAGGCGGAGAGATGCATTGCAAACGCCTGTAAAAGAACG
GCATAGCTACTAGACACTCTGATGTGGACCCTTGG CGCAGCCACGACAGGAGAGGT
GTGCATCAGCCGCTTGTAAGCACGCACTTCTGAG
```

*FIG. 7B*

HydA1 (cDNA) – wild type (SEQ ID NO:2)
ATGTCGGCGCTCGTGCTGAAGCCCTGCGCGGCCGTGTCTATTCGCGGCAGCTCCTGC
AGGGCGCGGCAGGTCGCCCCCCGCGCTCCGCTCGCAGCCAGCACCGTGCGTGTAGC
CCTTGCAACACTTGAGGCGCCCGCACGCCGCCTAGGCAACGTCGCTTGCGCGGCTGC
CGCACCCGCTGCGGAGGCGCCTTTGAGTCATGTCCAGCAGGCGCTCGCCGAGCTTGC
CAAGCCCAAGGACGACCCCACGCGCAAGCACGTCTGCGTGCAGGTGGCTCCGGCCG
TTCGTGTCGCTATTGCCGAGACCCTGGGCCTGGCGCCGGGCGCCACCACCCCCAAGC
AGCTGGCCGAGGGCCTCCGCCGCCTCGGCTTTGACGAGGTGTTTGACACGCTGTTTG
GCGCCGACCTGACCATCATGGAGGAGGGCAGCG AGCTGCTGCACCGCCTCACCGAG
CACCTGGAGGCCCACCCGCACTCCGACGAGCCGCTGCCCATGTTCACCAGCTGCTGC
CCCGGCTGGATCGCTATGCTGGAGAAATCTTACCCGGACCTGATCCCCTACGTGAGC
AGCTGCAAGAGCCCCCAGATGATGCTGGCGGCCATGGTCAAGTCCTACCTAGCGGA
AAAGAAGGGCATCGCGCCAAAGGACATGGTCATGGTGTCCATCATGCCCTGCACGC
GCAAGCAGTCGGAGGCTGACCGCGACTGGTTCTGTGTGGACGCCGACCCCACCCTG
CGCCAGCTGGACCACGTCATCACCACCGTGGAGCTGGGCAACATCTTCAAGGAGCG
CGGCATCAACCTGGCCGAGCTGCCCGAGGGCGAGTGGACAATCCAATGGGCGTGG
GCTCGGGCGCCGGCGTGCTGTTCGGCACCACCGGCGGTGTCATGGAGGCGGCGCTG
CGCACGGCCTATGAGCTGTTCACGGGCACGCCGCTGCCG CCCTGAGCCTGAGCGA
GGTGCGCGGCATGGACGGCATCAAGGAGACCAACATCACCATGGTGCCCGCGCCCG
GGTCCAAGTTTGAGGAGCTGCTGAAGCACCGCGCCGCCGCGCGCCGAGGCCGCC
GCGCACGGCACCCCCGGGCCGCTGGCCTGGGACGGCGGCGCGGGCTTCACCAGCGA
GGACGGCAGGGGCGGCATCACACTGCGCGTGGCCGTGGCCAACGGGCTGGGCAACG
CCAAGAAGCTGATCACCAAGATGCAGGCCGGCGAGGCCAAGTACGACTTTGTGGAG
ATCATGGCCTGCCCCGCGGGCTGTGTGGGCGGCGGCGGCCAGCCCCGCTCCACCGA
CAAGGCCATCACGCAGAAGCGGCAGGCGGCGCTGTACAACCTGGACGAGAAGTCCA
CGCTGCGCCGCAGCCACGAGAACCCGTCCATCCGCGAGCTGTACGACACGTACCTC
GGAGAGCCGCTGGGCCACAAGGCGCACGAGCTGCTGCACACCCACTACGTGGCCGG
CGGCGTGGAGGAGAAGGACGAGAAGAAGTGA

*FIG. 8*

HydA1 (cDNA) – optimized; removal of selected structures and putative regulatory motifs via silent nucleotide substitutions and codon optimization (SEQ ID NO:3)
GCTAGCGCCGCTCCTGCTGCTGAGGCTCCTCTGAGCCACGTGCAGCAGGCCCTGGCT
GAGCTGGCCAAGCCCAAGGACGACCCCACCCGCAAGCACGTGTGCGTCCAGGTCGC
CCCTGCTGTGCGCGTGGCCATTGCTGAGACTCTGGGCCTGGCTCCCGGCGCTACCAC
CCCTAAGCAGCTGGCTGAGGGCCTGCGCCGCCTGGGCTTTGATGAGGTGTTCGACAC
CCTGTTCGGCGCCGACCTGACCATCATGGAGGAGGGCTCTGAGCTGCTGCACCGCCT
GACCGAGCACCTGGAGGCTCACCCTCACAGCGACGAGCCCCTGCCCATGTTCACCA
GCTGCTGCCCCGGCTGGATCGCCATGCTGGAGAAGTCCTACCCCGACCTGATCCCCT
ACGTGTCCAGCTGCAAGAGCCCCCAGATGATGCTGGCCGCTATGGTCAAGAGCTAC
CTGGCCGAGAAGAAGGGCATTGCCCCCAAGGACATGGTCATGGTGTCCATCATGCC
CTGCACGCGCAAGCAGAGCGAGGCCGACCGCGACTGGTTCTGCGTCGACGCAGACC
CTACCCTGCGCCAGCTGGACCACGTGATCACCACCGTCGAGCTGGGCAACATCTTCA
AGGAGCGCGGCATCAACCTGGCGGAGCTGCCTGAGGGCGAGTGGGACAACCCTATG
GGCGTGGGTTCTGGCGCTGGCGTGCTGTTCGGCACCACTGGCGGTGTCATGGAGGCC
GCCCTGCGCACCGCTTACGAGCTGTTCACCGGCACCCCTCTGCCCCGCCTGTCTCTGT
CTGAGGTCCGCGGCATGGACGGCATCAAGGAGACTAACATCA CGATGGTGCCCGCT
CCCGGCAGCAAGTTCGAGGAGCTCCTGAAGCACCGCGCTGCCGCTCGCGCTGAGGC
TGCTGCTCACGGTACTCCCGGTCCTCTGGCTTGGGACGGCGGTGCTGGCTTCACTAG
CGAGGACGGTCGCGGCGGTATTACCCTGCGCGTGGCAGTGGCTAACGGCCTGGGCA
ACGCCAAGAAGCTGATCACCAAGATGCAGGCCGGCGAGGCGAAGTACGACTTCGTC
GAGATCATGGCCTGCCC CGCTGGCTGCGTCGGTGGTGGTGGCCAGCCTCGCAGCACC
GACAAGGCCATCACCCAGAAGCGCCAGGCCGCGCTGTACAACCTGGACGAGAAGTC
CACCCTGCGCCGCAGCCACGAGAACCCCAGCATCCGCGAGCTGTACGACACCTACC
TGGGCGAGCCCCTGGGCCACAAGGCTCACGAGCTGCTCCACACCCACTACGTGGCA
GGCGGCGTCGAGGAGAAGGACGAGAAGAAGTAG

*FIG. 9*

HydA1 (amino acid) (SEQ ID NO:4)
MSALVLKPCAAVSIRGSSCRARQVAPRAPLAASTVRVALATLEAPARRLGNVACAAAA
PAAEAPLSHVQQALAELAKPKDDPTRKHVCVQVAPAVRVAIAETLGLAPGATTPKQLA
EGLRRLGFDEVFDTLFGADLTIMEEGSELLHRLTEHLEAHPHSDEPLPMFTSCCPGWIAM
LEKSYPDLIPYVSSCKSPQMMLAAMVKSYLAEKKGIAPKDMVMVSIMPCTRKQSEADR
DWFCVDADPTLRQLDHVITTVELGNIFKERGINLAELPEGEWDNPMGVGSGAGVLFGTT
GGVMEAALRTAYELFTGTPLPRLSLSEVRGMDGIKETNITMVPAPGSKFEELLKHRAAA
RAEAAAHGTPGPLAWDGGAGFTSEDGRGGITLRVAVANGLGNAKKLITKMQAGEAKY
DFVEIMACPAGCVGGGQPRSTDKAITQKRQAALYNLDEKSTLRRSHENPSIRELYDTY
LGEPLGHKAHELLHTHYVAGGVEEKDEKK*

*FIG. 10*

Chimeric gene encoding a translational N-terminal fusion of an electron transfer protein PetF to HydA1 (SEQ ID NO:5)
CTCCACCTTCGCCGCCCGCGTTGGCGCTAAGCCCGCTGTACGCGGTGCTCGCCCCGC
CAGCCGCATGAGCTGCATGGCCTACAAGGTCACCCTGAAGACCCCTTCGGGCGACA
AGACCATTGAGTGCCCCGCTGACACCTACATCCTGGACGCTGCTGA GGAGGCCGGC
CTGGACCTGCCCTACTCTTGCCGCGCTGGTGCTTGCTCCAGCTGCGCCGGCAAGGTC
GCTGCCGGCACCGTGGACCAGTCGGACCAGTCCTTCCTGGACGATGCCCAGATGGG
CAACGGCTTCGTGCTGACCTGCGTGGCCTACCCCACCTCGGACTGCACCATCCAGAC
CCACCAGGAGGAGGCCCTGTACACCGGTGGTGGTGCATCTTGGAGCCACCCGCAGT
TCGAGAAGAGCGGCGGTGGTGCTAGCGCCGCTCCTGCTGCTGAGGCTCCTCTGAGCC
ACGTGCAGCAGGCCCTGGCTGAGCTGGCCAAGCCCAAGGACGACCCCACCCGCAAG
CACGTGTGCGTCCAGGTCGCCCTGCTGTGCGCGTGGCCATTGCTGAGACTCTGGGC
CTGGCTCCCGGCGCTACCACCCCTAAGCAGCTGGCTGAGGGCCTGCGCCGCCTGGGC
TTTGATGAGGTGTTCGACACCCTGTTCGGCGCCGACCTGACCATCATGG AGGAGGGC
TCTGAGCTGCTGCACCGCCTGACCGAGCACCTGGAGGCTCACCCTCACAGCGACGA
GCCCCTGCCCATGTTCACCAGCTGCTGCCCCGGCTGGATCGCCATGCTGGAGAAGTC
CTACCCCGACCTGATCCCCTACGTGTCCAGCTGCAAGAGCCCCCAGATGATGCTGGC
CGCTATGGTCAAGAGCTACCTGGCCGAGAAGAAGGGCATTGCCCCCAAGGACATGG
TCATGGTGTCCATCATGCCCTG CACGCGCAAGCAGAGCGAGGCCGACCGCGACTGG
TTCTGCGTCGACGCAGACCCTACCCTGCGCCAGCTGGACCACGTGATCACCACCGTC
GAGCTGGGCAACATCTTCAAGGAGCGCGGCATCAACCTGGCGGAGCTGCCTGAGGG
CGAGTGGGACAACCCTATGGGCGTGGGTTCTGGCGCTGGCGTGCTGTTCGGCACCAC
TGGCGGTGTCATGGAGGCCGCCCTGCGCACCGCTTACGAGCTGTTCACCGGC ACCCC
TCTGCCCCGCCTGTCTCTGTCTGAGGTCCGCGGCATGGACGGCATCAAGGAGACTAA
CATCACGATGGTGCCCGCTCCCGGCAGCAAGTTCGAGGAGCTCCTGAAGCACCGCG
CTGCCGCTCGCGCTGAGGCTGCTCACGGTACTCCCGGTCCTCTGGCTTGGGACG
GCGGTGCTGGCTTCACTAGCGAGGACGGTCGCGGCGGTATTACCCTGCGCGTGGCA
GTGGCTAACGGCCTGGGCAACGCCAAGAAGCTGATCACCAAGATGCAGGCCGGCGA
GGCGAAGTACGACTTCGTCGAGATCATGGCCTGCCCCGCTGGCTGCGTCGGTGGTGG
TGGCCAGCCTCGCAGCACCGACAAGGCCATCACCCAGAAGCGCCAGGCCGCGCTGT
ACAACCTGGACGAGAAGTCCACCCTGCGCCGCAGCCACGAGAACCCCAGCATCCGC
GAGCTGTACGACACCTACCTGGGCGAGCCCCTGGGCCACAAGGCTCACGAGCTGCT
CCACACCCACTACGTGGCAGGCGGCGTCGAGGAGAAGGACGAGAAGAAGTAG

*FIG. 11* pX-HydA - gene for constitutive expression of the hydrogenase HydA1 in C. reinhardtii
(SEQ ID NO:6)
TCGGGTTTCGCCACCTCTGACTTGAGCGTCGATTTTTGTGATGCTCGTCAGGGGGGC
GGAGCCTATGGAAAAACGCCAGCAACGCGGCCTTTTTACGGTTCCTGGCCTTTTGCT
GGCCTTTTGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCGCAGCG
AGTCAGTGAGCGAGGAAGCGGTCGCTGAGGCTTGACATGATTGGTGCGTATGTTTGT
ATGAAGCTACAGGACTGATTTGGCGGGCTATGAGGGCGGGGGAAGCTCTGGAAGGG
CCGCGATGGGGCGCGCGGCGTCCAGAAGGCGCCATACGGCCCGCTGGCGGCACCCA
TCCGGTATAAAAGCCCGCGACCCCGAACGGTGACCTCCACTTTCAGCGACAAACGA
GCACTTATACATACGCGACTATTCTGCCGCTATACATAACCACTCAGCTAGCTTAAG
ATCCCATCAAGCTTGCATGCCGGGCGCGCCAGAAGGAGCGCAGCCAAACCAGGATG
ATGTTTGATGGGGTATTTGAGCACTTGCAACCCTTATCCGGAAGCCCCCTGGCCCAC
AAAGGCTAGGCGCCAATGCAAGCAGTTCGCATGCAGCCCTGGAGCGGTGCCCTCC
TGATAAACCGGCCAGGGGGCCTATGTTCTTTACTTTTTACAAGAGAAGTCACTCAA
CATCTTAAAATGGCCAGGTGAGTCGACGAGCA AGCCCGGCGGATCAGGCAGCGTGC
TTGCAGATTTGACTTGCAACGCCCGCATTGTGTCGACGAAGGCTTTTGGCTCCTCTGT
CGCTGTCTCAAGCAGCATCTAACCCTGCGTCGCCGTTTCCATTTGCAGGAGATTCGA
GGTACCATACTCCACCTTCGCCGCCCGCGTTGGCGCTAAGCCCGCTGTACGCGGTGC
TCGCCCCGCCAGCCGCATGAGCTGCATGGCCTACAAGGTCACCCTGAAGACCCCTTC
GGGCGACAAGACCATTGAGTGCCCCGCTGACACCTACATCCTGGACGCTGCTGAGG
AGGCCGGCCTGGACCTGCCCTACTCTTGCCGCGCTGGTGCTTGCTCCAGCTGCGCCG
GCAAGGTCGCTGCCGGCACCGTGGACCAGTCGGACCAGTCCTTCCTGGACGATGCC
CAGATGGGCAACGGCTTCGTGCTGACCTGCGTGGCCTACCCCACCTCGGACTGCACC
ATCCAGACCCACCAGGAGGAGGCCCTGTACACCGGTGGTGGTGCATCTTGGAGCCA
CCCGCAGTTCGAGAAGAGCGGCGGTGGTGCTAGCGCCGCTCCTGCTGCTGAGGCTC
CTCTGAGCCACGTGCAGCAGGCCCTGGCTGAGCTGGCCAAGCCCAAGGACGACCCC
ACCCGCAAGCACGTGTGCGTCCAGGTCGCCCCTGCTGTGCGCGTGGCCATTGCTGAG
ACTCTGGGCCTGGCTCCCGGCGCTACCACCCCTAAGCAGCTGGCTGAGGGCCTGCGC
CGCCTGGGCTTTGATGAGGTGTTCGACACCCTGTTCGGCGCCGACCTGACCATCATG
GAGGAGGGCTCTGAGCTGCTGCACCGCCTGACCGAGCACCTGGAGGCTCACCCTCA
CAGCGACGAGCCCCTGCCCATGTTCACCAGCTGCTGCCCCGGCTGGATCGCCATGCT
GGAGAAGTCCTACCCCGACCTGATCCCCTACGTGTCCAGCTGCAAGAGCCCCCAGAT
GATGCTGGCCGCTATGGTCAAGAGCTACCTGGCCGA AGAAGGGCATTGCCCCCA
AGGACATGGTCATGGTGTCCATCATGCCCTGCACGCGCAAGCAGAGCGAGGCCGAC
CGCGACTGGTTCTGCGTCGACGCAGACCCTACCCTGCGCCAGCTGGACCACGTGATC
ACCACCGTCGAGCTGGGCAACATCTTCAAGGAGCGCGGCATCAACCTGGCGGAGCT
GCCTGAGGGCGAGTGGGACAACCCTATGGGCGTGGGTTCTGGCGCTGGCGTGCTGTT
CGGCACCACTGGCGGTGTCATGGAGGCCGCCCTGCGCACCGCTTACGAGCTGTTCAC
CGGCACCCCTCTGCCCCGCCTGTCTCTGTCTGAGGTCCGCGGCATGGACGGCATCAA
GGAGACTAACATCACGATGGTGCCCGCTCCCGGCAGCAAGTTCGAGGAGCTCCTGA
AGCACCGCGCTGCCGCTCGCGCTGAGGCTGCTGCTCACGGTACTCCCGGTCCTCTGG

FIG. 12A

```
CTTGGGACGGCGGTGCTGGCTTCACTAGCGAGGACGGTCGCGGCGGTATTACCCTGC
GCGTGGCAGTGGCTAACGGCCTGGGCAACGCCAAGAAGCTGATCACCAAGATGCAG
GCCGGCGAGGCGAAGTACGACTTCGTCGAGATCATGGCCTGCCCCGCTGGCTGCGT
CGGTGGTGGTGGCCAGCCTCGCAGCACCGACAAGGCCATCACCCAGAAGCGCCAGG
CCGCGCTGTACAACCTGGACGAGAAGTCCACCCTGCGCCGCAGCCACGAGAACCCC
AGCATCCGCGAGCTGTACGACACCTACCTGGGCGAGCCCCTGGGCCACAAGGCTCA
CGAGCTGCTCCACACCCACTACGTGGCAGGCGGCGTCGAGGAGAAGGACGAGAAG
AAGTAGGAATTCCCGCTCCGTGTAAATGGAGGCGCTCGTTGATCTGAGCCTTGCCCC
CTGACGAACGGCGGTGGATGGAAGATACTGCTCTCAAGTGCTGAAGCGGTAGCTTA
GCTCCCCGTTTCGTGCTGATCAGTCTTTTTCAACACGTAAAAGCGGAGGAGTTTTG
CAATTTGTTGGTTGTAACGATCCTCCGTTGATTTGGCCTCTTTCTCCATTGGCGGG
CTGGGCGTATTTGAAGCGAGATCT
```

*FIG. 12B* pX-HydG (chimeric gene hydGm) (SEQ ID NO:12)
GCAGAGGTTGGGAATCGCTTTGAAAATCCAGCAATCGGGTCTCAGCTGTCTCAGGCC
GCACGCGCCTTGGACAAGGCACTTCAGTAACGTACTCCAAGCCCTCTATCTGCATGC
CCACAAAGCGCAGGAATGCCGACCATCGTGCCAGACTGTGCCGCGCCCGAACCGAA
ATCCGTCACTCCCCTTGGTTCACATGGTGGCATGGTCCCCCCTGTTCGCCCAAAGCCT
GGTTCAGCGCCCAGTGGCAAACGGCTTTGGCTCAGCTCCTTGGTATTGCTGGTTTCT
AGCAATCTCGTCCGTTCCTCTGTTGCCAATGTAGCAGGTGCAAACAGTCGAATACGG
TTTTACTCAGGGGCAATCTCAACTAACAGAGGCCCTGGGCCTGTTGCCTGGAACCTA
TGAAGACGATAATGCCACGGCGACTTCGAGCCTGAGGGAAGTTTGCACCTGTACC
GCATTGTGCAAGGTTACGGTACATGATAGGGGGAGTGCGACGCGGTAAGGCTTGGC
GCAGCTTGGCGCGTCTGCCTTGCATGCATGTCCGAAACACGCCACGTCGCGCCACGA
AAAGCGGTAAAAGGACCTGACATGGTCCTCCAGGGTGTTACCACTTCCATTTCGCTC
AGCTGGGATGGTGCTCGTAGGTGCACCAGCGTTGATTATTTCAGGCAGGAAGCGGCT
GCGAAGCCCGCCTTTCACTGAAGACTGGGATGAGCGCACCTGTACCTGCCAGTATCG
TACCGGCGCGCTACCGATGCGTGTAGTAG AGCTTGCTGCCATACAGTAACTCTGGTA
CTCCCAGCCACCGGGCGTAGCGAGCAGACTCAATAAGTATGATGGGTTCTTATTGCA
GCCGCTGTTACAGTTTACAGCGCAAGGGAACACGCCCTCATTACAGAACTAACTC
AACCTACTCCATCCATATGCAGGCAAGTAATAGTCCAACCAGTCTTGCAGCGGCGCT
AGGCCGTCTCGCGCTTTCGACCCATCTGACCTTATCGCGTGCTCCCTCTCTCGTTCT G
GGTGCAGACCGTGCGTGCTCCCGCCGCCTCCGGCGTTGCCACCCGCGTGGCTGGCCG
CCGCATGTGCCGCCCCGTGGCGGCCCTGCAGgcACCGGCGGTGGCACCGCTCACGGC
AAGGCTTCCGCAACTCGCGAGTACGCCGGCGACTTCCTGCCCGGCACCACCATCTCT
CATGCTTGGAGCGTCGAGCGCGAGACTCACCACCGCTACCGCAACCCCGCCGAGTG
GATCAACGAGGCCGCCATCCACAAGGCC CTGGAGACTAGCAAGGCCGACGCTCAGG
ACGCTGGCCGCGTGCGCGAGATCCTGGCCAAGGCCAAGGAGAAGGCCTTTGTCACC
GAGCACGCCCCGTGAACGCCGAGAGCAAGAGCGAGTTCGTGCAGGGCCTGACCCT
GGAGGAGTGCGCCACCCTGATCAACGTCGACAGCAACAACGTCGAGCTGATGAACG
AGATTTTCGACACCGCCCTGGCCATCAAGGAGCGCATCTACGGCAACCGCGTGGTG
CTGTTCGCCCCCTGTACATTGCCAACCACTGCATGAACACGTGCACCTACTGCGCC
TTCCGCAGCGCCAACAAGGGCATGGAGCGCAGCATCCTGACCGACGACGACCTGCG
CGAGGAGGTGGCAGCTCTCCAGCGCCAGGGTCACCGCCGCATTCTGGCTCTGACCG
GCGAGCACCCCAAGTACACCTTCGACAACTTTCTGCACGCCGTGAACGTGATCGCCT
CTGTCAAGACCGAGCCCGAGGGCAGCATCCGCCG CATCAACGTCGAGATCCCCCCC
CTGTCCGTGTCCGACATGCGCCGCTGAAGAACACCGACTCCGTGGGCACCTTCGTG
CTGTTTCAGGAGACTTACCACCGGGACACCTTCAAGGTCATGCACCCCAGCGGCCCC
AAGAGCGACTTCGACTTCCGCGTGCTGACCCAGGACCGCGCTATGCGCGCTGGCCTG
GACGACGTGGGCATTGGCGCTCTGTTCGGCCTGTACGACTACCGCTACGAGGTCTGC
GCCATGCTGATGCACAGCGAGCACCTGGAGCGCGAGTACAACGCTGGCCCCACAC
CATCTCTGTGCCCGCATGCGCCCTGCTGATGGCAGCGAGCTGAGCATTGCTCCCCC
CTACCCTGTTAACGACGCCGACTTCATGAAGCTGGTGGCCGTGCTGCGCATTGCCGT

FIG. 13A

GCCCTACACCGGCATGATCCTGAGCACCCGCGAGAGCCCCGAGATGCGCAGCGCTC
TGCTGAAGTGCGGCATGAGCCAGATGAGCGCCGGCT CTCGCACCGACGTGGGCGCC
TACCACAAGGACCACACCCTGAGCACCGAGGCCAACCTGAGCAAGCTAGCGGGCCA
GTTTACGCTCCAGGACGAGCGCCCACCAACGAGATCGTGAAGTGGCTGATGGAGG
AGGGTTATGTCCCCAGCTGGTGCACCGCATGCTACCGCCAGGGTCGCACCGGCGAG
GACTTTATGAACATCTGCAAGGCCGGCGACATCCACGACTTTTGCCACCCCAACAGC
CTGCTGACTCTCCAGGAGTACCTGATGGACTACGCCGACCCCGACCTGCGCAAGAA
GGGCGAGCAGGTCATCGCTCGCGAGATGGGCCCTGATGCTTCCGAGCCTCTGAGCG
CACAGAGCCGCAAGCGCCTGGAGCGCAAGATGAAGCAGGTCCTGGAGGGCGAGCA
CGACGTGTACCTGTAGGAATTCTGGAAGTACGTTGATGTTGTTATTTCAACTGGGTC
ACCGTAGCTTGCTCGTGCCCAGTTGTGGATGCGAGTTATACG TCATTGCGTAACAT
GTTCATGATAGACTGCATTAGGTAGGCGTCGTGTGTGAGCACATACAGAAGTCATCA
CGCAAATGGACACGTTCCGGCGAACCCGAGGGGAAAGGCTTGGGCCAGTACATTAT
TTCAACACTAAAATATGTAACATAATGGAACTTGAGCACGGTCCGGGAGCGCAGGC
TGGGCTTGGGGGTCGCGGCTCGAAGGAGAGGGGCGACGTTGGGCAGGTCGGGGCT
TCAACCGGGTT

FIG. 13B pX-HydEF (chimeric gene hydEFm) (SEQ ID NO:13)
ACTAGAGCAGAGGTTGGGAATCGCTTTGAAAATCCAGCAATCGGGTCTCAGCTGTCT
CAGGCCGCACGCGCCTTGGACAAGGCACTTCAGTAACGTACTCCAAGCCCTCTATCT
GCATGCCCACAAAGCGCAGGAATGCCGACCATCGTGCCAGACTGTGCCGCGCCCGA
ACCGAAATCCGTCACTCCCCTTGGTTCACATGGTGGCATGGTCCCCCTGTTCGCCC
AAAGCCTGGTTCAGCGCCCAGTGGCAAACGGCTTTGGCTCAGCTCCTTGGTATTGCT
GGTTTCTAGCAATCTCGTCCGTTCCTCTGTTGCCAATGTAGCAGGTGCAAACAGTCG
AATACGGTTTTACTCAGGGGCAATCTCAACTAACAGAGGCCCTGGGCCTGTTGCCTG
GAACCTATGAAGACGATAATGCCACGGCGACTTTCGAGCCTGAGGGAAGTTTGCAC
CTGTACCGCATTGTGCAAGGTTACGGTACA TGATAGGGGAGTGCGACGCGGTAAG
GCTTGGCGCAGCTTGGCGCGTCTGCCTTGCATGCATGTCCGAAACACGCCACGTCGC
GCCACGAAAAGCGGTAAAAGGACCTGACATGGTCCTCCAGGGTGTTACCACTTCCA
TTTCGCTCAGCTGGGATGGTGCTCGTAGGTGCACCAGCGTTGATTATTTCAGGCAGG
AAGCGGCTGCGAAGCCCGCCTTTCACTGAAGACTGGGATGAGCGCACCTGTACCTG
CCAGTATCGTACCGGCGCGCTACCGATGCGTGTAGTAGAGCTTGCTGCCATACAGTA
ACTCTGGTACTCCCAGCCACCGGGCGTAGCGAGCAGACTCAATAAGTATGATGGGTT
CTTATTGCAGCCGCTGTTACAGTTTACAGCGCAAGGGAACACGCCCCTCATTCACAG
AACTAACTCAACCTACTCCATCCATATGCAGGCAAGTAATAGTCCAACCAGTCTTGC
AGCGGCGCTAGGCCGTCTCGCGCTTTCGACCC ATCTGACCTTATCGCGTGCTCCCTCT
CTCGTTCTGGGTGCAGACCGTGCGTGCTCCCGCCGCCTCCGGCGTTGCCACCCGCGT
GGCTGGCCGCCGCATGTGCCGCCCCGTGGCGGCCCTGCAGGGTGGTACTCACCACC
ACCACCACCACGGCTCTGGCGGCGGTTCTGGTGGTGGTTCTGGCGGTGTCGCTGCTC
ACGCCAGCGCCAGCAAGGCTACTCCTGATGTGCCCGTGGACGACCTGCCTCCTGCTC
ACGCGCGTGCTGCCGTGGCTGCTGCTAACCGCCGCGCTCGCGCTATGGCTTCCGCTG
AGGCTGCTGCCGAGACTCTGGGCGACTTCCTGGGCCTGGGCAAGGGTGGCCTGTCTC
CCGGCGCTACTGCTAACCTGGACCGCGAGCAGGTCCTGGGCGTGCTGGAGGCTGTG
TGGCGCCGGGGCGACCTGAACCTGGAGCGCGCTCTGTACAGCCACGCCAACGCCGT
GACCAACAAGTATTGCGGCGGTGGCGTGTACTA CCGGGGCCTGGTCGAGTTCAGCA
ACATCTGCCAGAACGACTGCTCCTACTGCGGCATCCGCAACAACCAGAAGGAGGTC
TGGCGCTACACCATGCCGGTCGAGGAGGTGGTCGAGGTCGCCAAGTGGGCCCTGGA
GAACGGCATCCGGAACATCATGCTCCAGGGCGGCGAGCTCAAGACCGAGCAGCGCC
TGGCTTACCTGGAGGCCTGCGTCCGCGCCATCCGCGAGGAGACTACTCAGCTGGACC
TGGAGATGCGCGCACGCGCTGCTTCGACCACCACTGCTGAGGCCGCTGCTTCCGCCC
AGGCCGACGCTGAGGCTAAGCGCGGCGAGCCTGAGCTGGGTGTCGTGGTGTCTCTG
AGCGTCGGCGAGCTGCCGATGGAGCAGTACGAGCGCCTGTTTCGCGCTGGCGCTCG
CCGCTACCTGATCCGCATCGAGACTAGCAACCCCGACCTGTACGCCGCCCTGCACCC
CGAGCCTATGTCTTGGCATGCTCGCGTCGAGTGCCTGC GCAACCTGAAGAAGGCCG
GCTACATGCTGGGCACCGGCGTGATGGTCGGCCTGCCTGGCCAGACTCTGCACGACC
TGGCCGGCGACGTGATGTTCTTCCGCGACATCAAGGCCGACATGATCGGCATGGGC
CCCTTCATCACCCAGCCCGGCACCCCGCTACCGACAAGTGGACCGCTCTGTACCCC
AACGCGAACAAGAACAGCCACATGAAGTCCATGTTCGACCTGACCACCGCCATGAA
CGCCCTCGTGCGCATCACGATGGGCAACGTGAACATCAGCGCCACCACCGCCCTCC
AGGCCATCATTCCCACTGGCCGCGAGATCGCTCTGGAGCGCGGTGCCAACGTGGTC
ATGCCCATCCTGACCCCCACCCAGTACCGCGAGAGCTACCAGCTGTACGAGGGCAA

FIG. 14A

```
GCCCTGCATCACCGACACCGCTGTGCAGTGCCGCCGCTGCCTGGACATGCGCCTGCA
CTCTGTGGGCAAGACCAGCGCCGCGGGCGTGTGGGCGACCCTGCTTCCTTCCTGCA
CCCCATTGTGGGCGTGCCCGTGCCCACGACCTGAGCAGCCCTGCTCTCGCTGCTGC
TGCCAGCGCCGACTTTCACGAGGTCGGCGCTGGTCCTGGAACCCCATTCGCCTGGA
GCGGCTGGTCGAGGTGCCCGACCGCTACCCTGACCCTGACAACCATGGCCGCAAGA
AGGCTGGCGCTGGCAAGGGCGGCAAGGCCCACGACTCTCACGACGACGGCGACCAC
GACGACCACCACCACCACCACGGTGCTGCTCCCGCTGGTGCTGCTGCCGGCAAGGG
TACTGGCGCTGCTGCTATTGGCGGCGGTGCTGGTGCTTCTCGCCAGCGCGTGGCAGG
CGCAGCTGCTGCTTCTGCTCGCCTGTGCGCTGGTGCTCGCCGCGCTGGTCGCGTGGT
GGCTTCTCCTCTGCGCCCTGCTGCTGCTTGCCAGGGCGTGGCCGTGAAGGCTGCTGC
TGCGGCTGCTGGCGAGGACGCAGGCGCTGGTACTTCTGGCGTGGGCAGCAACATCG
TGACCAGCCCCGGCATTGCCAGCACCACTGCTCACGGCGTGCCCCGCATCAACATCG
GCGTGTTCGGCGTGATGAACGCCGGCAAGTCGACCCTGGTCAACGCCCTGGCTCAG
CAGGAGGCCTGCATCGTCGATAGCACCCCTGGCACCACCGCCGATGTCAAGACCGT
GCTGCTGGAGCTGCACGCCCTGGGCCCTGCCAAGCTGCTGGACACTGCTGGCCTGGA
CGAGGTCGGCGGCCTGGGCGACAAGAAGCGCCGCAAGGCCCTGAACACCCTGAAG
GAGTGCGACGTCGCCGTCCTGGTGGTGGACACCGACACCGCCGCTGCCGCCATTAA
GTCTGGCCGCCTGGCTGAGGCCCTGGAGTGGGAGAGCAAGGTCATGGAGCAGGCCC
ACAAGTACAACGTGTCCCCGGTCCTGCTGCTGAACGTGAAGTCTCGCGGCCTGCCCG
AGGCCCAGGCTGCTTCTATGCTGGAGGCCGTGGCTGGCATGCTGGACCCCA GCAAG
CAGATCCCCGCATGAGCCTGGACCTGGCCAGCACTCCTCTGCACGAGCGCAGCAC
CATCACCAGCGCCTTCGTGAAGGAGGGCGCTGTCCGCTCTAGCCGCTACGGCGCTCC
TCTGCCTGGTTGCCTGCCTCGCTGGTCCCTGGGTCGCAACGCTCGCCTGCTGATGGTC
ATCCCGATGGACGCCGAGACTCCCGGTGGTCGCCTGCTGCGGCCTCAGGCTCAGGTC
ATGGAGGAGGCTATCCGCCACTG GGCCACCGTGCTGTCTGTGCGGCTGGACCTGGA
CGCTGCTCGCGGCAAGCTGGGTCCCGAGGCTTGCGAGATGGAGCGCCAGCGCTTCG
ACGGCGTGATCGCCATGATGGAGCGCAACGACGGCCCCACCCTGGTCGTGACCGAC
AGCCAGGCCATTGATGTGGTGCACCCCTGGACCCTGGACCGCTCTTCTGGGCGGCCG
CTGGTGCCCATCACCACCTTCTCGATCGCTATGGCCTACCAGCAGAACGGCGGT CGC
CTGGACCCTTTCGTCGAGGGCCTGGAGGCGCTGGAGACTCTCCAGGACGGCGACCG
CGTGCTGATCAGCGAGGCCTGCAACCACAACCGCATCACCTCCGCCTGCAACGACA
TCGGCATGGTGCAGATCCCCAACAAGCTGGAGGCTGCCCTCGGCGGCAAGAAGCTC
CAGATCGAGCACGCCTTCGGCCGCGAGTTCCCTGAGCTGGAGTCTGGCGGCATGGA
CGGCCTGAAGCTGGCCATTCACTGCGGCGGCTGCATGATCGACGCCCAGAAGATGC
AGCAGCGCATGAAGGACCTGCACGAGGCCGGCGTGCCCGTGACCAACTACGGCGTG
TTCTTCAGCTGGGCCGCGTGGCCTGATGCTCTGCGCCGCGCTCTGGAGCCTTGGGGT
GTCGAGCCTCCTGTGGGCACCCCTGCTACTCCAGCCGCTGCTCCTGCTACCGCCGCC
AGCGGTGTCTAAGAATTCTGGAAGTACGTTGATGTTGTTATTTCAACTGGGTCACCG
TAGCTTGCTCGTGCCCCAGTTGTGGATGCGAGTTATACGTCATTGCGTAACATGTTC
ATGATAGACTGCATTAGGTAGGCGTCGTGTGTGAGCACATACAGAAGTCATCACGC
AAATGGACACGTTCCGGCGAACCCGAGGGGAAAGGCTTGGGCCAGTACATTATTTC
AACACTAAAATATGTAACATAATGGAACTTGAGCACGGTCCGGGAGCGCAGGCTGG
GCTTGGGGGTCGCGGCTCGAAGGAGAGGGGCGACGTTGGGGCAGGTCGGGGCTTCA
ACCGGGTTTCACTAGA
```

FIG. 14B

DEVELOPMENT OF MICROORGANISMS FOR HYDROGEN PRODUCTION

PRIORITY STATEMENT

This application claims priority to U.S. Provisional Patent Application No. 61/905,010, filed Nov. 15, 2013, hereby incorporated by reference in its entirety.

FIELD OF THE INVENTION

The present invention relates to methods and compositions for engineering microorganisms to produce hydrogen ($H_2$).

BACKGROUND OF THE INVENTION

Nearly 10-11 million tons of $H_2$ are produced in the U.S. each year. The majority of commercial $H_2$ is produced by natural gas reformation. Oil refineries are the largest consumer of $H_2$, purchasing millions of tons of $H_2$ each year to satisfy the need for oil cracking. Ammonia plants and several other chemical industries are among the other major consumers of $H_2$. Use of $H_2$ is predicted to increase annually by nearly 1% based on the current market. In addition, a significant expansion is anticipated with introduction of $H_2$-powered vehicles/aircrafts and rise of prices of electric power.

Numerous research groups have been working on creating economical catalysts for solar-powered $H_2$ production from water [18, 19]. Quick inactivation through oxidation poses a tremendous challenge for developing chemical catalysts. Nature has solved this problem in algae by continuous regeneration and replacement of oxidized biological catalysts, namely enzymes. Green microalgae have the potential to combine the generation of $H_2$ with light powered oxidation of water molecules releasing protons and electrons needed for the formation of $H_2$ (Melis, 2007, Planta 226: 1075-86; M. Ghirardi et al., 2007, Ann. Rev. of Plant Biology 58: 71-91). Several species of algae including *C. reinhardtii* possess the ability to convert solar power into $H_2$. They possess $H_2$ evolving redox metalloenzymes referred to as [FeFe] $H_2$ases which reversibly catalyze the reaction

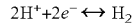

$$2H^+ + 2e^- \leftrightarrow H_2$$

These $H_2$ases combine electrons and protons from sun-light powered splitting of water to form $H_2$ [12, 20].

Green algae are among the most promising organisms for economical production of $H_2$ biofuels. Many species of microalgae are already exploited for numerous biotechnological applications such as production of food additives and animal feed that underscores economic benefits of microalgae-based manufacturing [21, 22]. Protocols for transformation of nuclear and chloroplast genomes have been established for *C. reinhardtii* [23-25]. Furthermore, a considerable knowledge has been accumulated about structure and function of $H_2$ases.

Green algae represent an advantageous model organism for the generation of $H_2$ through modification of $H_2$ase activity. Algae are eukaryotic organisms, and results obtained in algae can be used to predict similar results in other eukaryotic organisms, such as plants or fungi, or other eukaryotic cells. Further, as photosynthetic organisms, algae serve as an effective model for other photosynthesizing organisms, including plants and prokaryotic cyanobacteria.

[FeFe] $H_2$ases

[FeFe] $H_2$ases from several bacterial and algal species catalyze formation of $H_2$. The [FeFe] $H_2$ases from *C. reinhardtii* (HydA1) and from *Clostridium pasteurianum* (CpHydA) are among enzymes with the greatest catalytic activity in $H_2$ evolution reaction [11, 15]. The two enzymes share considerable similarity in the catalytic domain although the hosts belong to different kingdoms, Plantae and Bacteria [26, 27]. [FeFe] $H_2$ases contain accessory FeS clusters, $Fe_4S_4$ and $Fe_2S_2$, which transfer electrons to the active site of the enzyme. The active (catalytic) site, the H-cluster, consists of the $Fe_2S_2$ subcluster and unusual ligands [28]. Both CpHydA and HydA1 are monomers with considerable homology in the catalytic domain. HydA1, which is one of the smallest [FeFe] $H_2$ases, consists of a catalytic domain alone. HydA1 and CpHydA show similar $H_2$ evolving activity when supplied with an appropriate electron donor [29].

The *C. reinhardtii* $H_2$ase genes are nuclear-encoded and contain chloroplast targeting signal peptides. Expression of HydA1 is highly regulated. $O_2$ quickly inhibits transcription of hydA1 [16]. The classical $Fe_4S_4$ and $Fe_2S_2$ clusters are encountered in a variety of proteins. The metabolic pathway for synthesis of these clusters is functional under both aerobic and anaerobic conditions and readily available in algal cells [30]. In addition, at least three maturation proteins, HydE, HydF, and HydG, are required for assembly of the active site [29]. The genes hydE, hydF, and hydG function to couple radical S-adenosyl-L-methionine chemistry and nucleotide hydrolysis to synthesise CO and CN ligands and assemble the H-cluster [31, 32]. Insertion of the H-cluster completes maturation of HydA1.

Electron Source for $H_2$ases

Algal $H_2$ases serve as an electron sink providing a selective advantage under anaerobiosis by avoiding overreduction of photosystem I (PSI) electron acceptors [33, 34]. Two electron supply pathways have been identified for algal $H_2$ases—a direct and an indirect pathway [9, 35]. In the direct pathway, electrons are passed from photosystem II (PSII) to PSI, and then from a reduced ferredoxin to $H_2$ase. The indirect pathway starts from starch catabolism injecting electrons into the plastoquinone pool. Both pathways share electron carrier cytochrome b6/f complex, plastocyanin, and PSI. The indirect pathway is equipped with a cyclic electron flow (CEF) system which recycles excess electrons to the cytochrome b6/f complex or plastoquinone pool.

$H_2$ases receive electrons from a ferredoxin which is reduced, for example by PSI. Consequently, algal $H_2$ases compete for electron source with several metabolic pathways such as production of NADPH for $CO_2$ fixation, a CEF system of PSI, and several essential reduction reactions [36, 37]. Fusion of a *C. reinhardtii* ferredoxin (Fdx1 encoded by petF) with HydA1 switched bias of electron transfer to $H_2$ase from ferredoxin:NADP$^+$-oxidoreductase (FNR) in an in vitro bioassay [38]. FNR generates NADPH. Similarly, deletion of a Proton Gradient Regulation Like 1 (PGRL1) protein from the CEF system impaired CEF and increased photoproduction of $H_2$ in microalgae by five-fold [39]. Previously reported data also pointed to a relationship between $H_2$ase activity and CEF [40, 41]. Interestingly, the pgrl1 knockdown mutant showed the same photosynthesis rate as the wild type *Chlamydomonas*. In contrast, photosynthetic activity of *Arabidopsis* pgrl1 and pgrl5 mutants was severely affected under high light intensity [42] [43]. A mechanism of neutralization of excess reducing power in microalgae evidently is more effective than in higher plants.

$O_2$ Sensitivity $O_2$ quickly and irreversibly inhibits $H_2$-forming $H_2$ases [16, 44]. For example, the HydA1 activity is inhibited within 30-90 seconds under <2% $O_2$ [16]. Analysis of the *C. acetobutylicum* [FeFe] $H_2$ase showed that $O_2$ inhibition starts from reversible formation of an $O_2$ adduct that is followed by irreversible transformation of the catalytic cluster [45, 46]. Analysis of crystal structures, molecular dynamics (MD) simulations, and site directed mutagenesis of $H_2$ases suggested a gas access channel connecting the active site with the protein surface [47-49]. Mutation of residues, which were predicted computationally to form the channel's wall, modified rates of migration of $H_2$ and CO to the catalytic site [50, 51]. A direct connection between $O_2$ sensitivity and a gas access channel was shown on the regulatory $H_2$ase HupUV [52, 53]. Replacement of two residues in the putative gas channel in HupUV widened the gas channel and modified $O_2$ sensitivity.

$H_2$ Manufacturing Processes

Several research groups have worked on development of a process for $H_2$ production in microalgae [12-14]. Two models have been developed so far based on anaerobic S-deprivation in light [9, 10]. S-deprivation inhibits synthesis of S-rich proteins including some proteins of the PSII reaction center [17]. This leads to interruption of photosynthesis and $O_2$ formation. Anaerobosis under light enables formation of $H_2$. However, algae do not survive more than a few days in a S-depleted medium. Consequently, $H_2$ yield is low. Recently, Surzyski and co-workers engineered *Chlamydomonas* for inducible turning off/on the PSII activity [54]. As result, $H_2$ photoproduction in the recombinant strain was prolonged up to two weeks by alternating the dark/light cycles. A mutant strain with a partial $O_2$ tolerance, up to 2% (v/v), was produced by classical mutagenesis, but $H_2$ yield was several times lower that under anaerobiosis [55]. Recently, a bacterial $H_2$ase variant with a reduced rate of $O_2$ migration into the active site was created by site-directed mutagenesis [56]. However, the mutations decreased the $H_2$ forming activity.

$O_2$ sensitivity is viewed as the major obstacle in a way of developing a commercially viable process for renewable production of $H_2$ [14, 57, 58]. Metabolic engineering presents a powerful approach to overcome $O_2$ sensitivity of algal $H_2$ases. Recent breakthroughs in understanding of structure and function of these enzymes open new opportunities to engineer microalgae for commercial manufacturing of $H_2$.

No commercially viable renewable process for $H_2$ manufacturing has been developed to date. The microalgae *C. reinhardti* and the bacterium *C. pasteurianum* possess some of the most active enzymes with $H_2$-forming activity. Several research groups have worked on development of a process for $H_2$ production in microalgae. Two models of a process for $H_2$ production in algae have been developed based on anaerobic sulfur(S)-deprivation in light to prevent generation of $O_2$ during synthesis of $H_2$ [9, 10]. Accordingly, $H_2$ production is low. The limiting factor currently is $O_2$ sensitivity of $H_2$ases [15-17].

SUMMARY

The present invention provides an innovative approach to metabolically engineer a microorganism to generate $H_2$ in large quantities. Because a $H_2$ase is synthesized in an inactive pre-form, it requires maturation proteins which are responsible for a catalytic cluster and activation of $H_2$ase. According to one aspect of the invention, a gene encoding a $H_2$-forming $H_2$ase is engineered for expression in the presence of $O_2$ in microbial cells. Expression in the presence of $O_2$ enables accumulation of the pre-form of the enzyme in microbial cells under aerobic conditions. In another aspect, expression of maturation proteins is regulated in order to limit synthesis of the $O_2$-sensitive catalytic cluster to microanaerobic or anaerobic conditions. Consequently, maturation of the $H_2$-forming $H_2$ase is enabled only under microanaerobic or anaerobic conditions preventing inhibition by photosynthetic or atmospheric $O_2$, thereby permitting rapid maturation of large quantities of $H_2$ases and increase in the yield of $H_2$. Accordingly, the novel organisms of the invention are capable of synthesizing and releasing $H_2$ in large quantities and are also capable of releasing $H_2$.

In one embodiment, the engineered nucleic acid encodes an $H_2$-forming $H_2$ase derived from *C. reinhardti*, *C. pasteurianum*, or *C. acetobutylicum*. In another embodiment, the engineered nucleic acid sequences encode $H_2$ase maturation proteins that are codon-optimized for expression in the host cell. In a related embodiment, at least one nucleic acid sequence which encodes a maturation protein is optimized to limit expression to microanaerobic or anaerobic conditions.

In another aspect, a method for selecting, engineering, and using microorganisms for $H_2$ production is also disclosed. In one aspect, various microorganisms capable of metabolizing organic nutrients under microanaerobic or anaerobic conditions and supplying electrons to $H_2$ase are used. Such organisms may be autotrophic, mixotrophic, or heterotrophic. In one embodiment, a host cell is one that harbors an endogenous gene encoding for electron donor capable to supply electrons to $H_2$ase. Examples of such host cells include microalgae *C. reinhardtii* and bacteria *C. pasteurianum*.

In another embodiment, the microorganisms are introduced with one or more exogenous nucleic acid sequences encoding an elector donor capable of supplying $H_2$ases with electrons. In one embodiment, the electron donor is ferredoxin. Normally, $H_2$ase competes with other enzymes, such as ferredoxin:NADP+-oxidoreductase (FNR1) for electrons supplied by ferredoxin. However, when overexpressed in accordance with the present invention, $H_2$-forming $H_2$ases favorably compete with competitors for electrons supplied by ferredoxin under microanaerobic or anaerobic conditions in the presence of S. In vitro experimental evidence suggests that an electron donor may be available to $H_2$-forming $H_2$ases in the presence of S [38]. However, donor availability in vivo in the presence of S has not been demonstrated prior to the present invention.

In another aspect of the invention, a method is provided to introduce an engineered nucleic acid sequence encoding one or more proteins of interest into photosynthetic microorganisms such as algae. A continuous process for light-induced production of $H_2$ in microalgae may be achieved with engineered strains via balancing photosynthetic (growth) and production phases where the later undergoes under microanaerobic or anaerobic conditions. Cultures are cycled between bright light and shaded conditions. Cells exposed to bright light undergo photosynthesis while the shaded cells produce $H_2$ without S-deprivation and stress caused by depletion of S-rich proteins. Cell cultures continue to grow and undergo normal processes during $H_2$ production that improves overall health, resulting in substantial increase in $H_2$ yield compared to S-deprived methods of production.

In one aspect of the invention, light intensity can be regulated during the growth and the production phases to accelerate establishment of microanaerobiosis. The invention thereby permits high levels of $H_2$ase activity under light intensities supporting microanaerobiosis via metabolic engineering instead of S-deprivation.

In certain embodiments, the engineered cell of the invention produced $H_2$ in an amount two-fold greater than amounts produced by host cells comprising no engineered nucleic acid sequences.

The present invention is novel approach to overcome $O_2$ sensitivity of $H_2$ases by separation of expression of HydA1 and maturation proteins as proposed above. Further, the present invention provides a unique process for continuous photoproduction of $H_2$, which has clear advantages over the prior art processes such as S-deprivation. The invention thereby provides compositions and methods for $H_2$ production that improve overall health of cell population and productivity.

Therefore, it is a primary object, feature, or advantage of the present invention to improve upon the state of the art.

It is another object, feature, or advantage of the present invention to provide a method and system for producing $H_2$ by metabolically engineering a microorganism to generate $H_2$ continuously in large quantities.

It is another object, feature, or advantage of the present invention to provide methods and compositions for gene constructs to permit the expression of functional $H_2$-producing $H_2$ases in an organism.

It is another object, feature, or advantage of the present invention to provide a method and system for producing $H_2$ by metabolically engineering C. rheinhardhii to generate $H_2$ continuously in large quantities.

It is another object, feature, or advantage of the present invention to provide a method and system for $H_2$ production by a $H_2$ase enzyme in the presence of S.

It is another object, feature, or advantage of the present invention to provide a method and system for continuous expression of HydA1 in C. rheinhardhii, while expression of maturation proteins is regulated in order to limit synthesis of the $O_2$-sensitive catalytic cluster to microanaerobic or anaerobic conditions.

It is another object, feature, or advantage of the present invention to provide a method and system for maturation of HydA1 enabled only under microanaerobic or anaerobic conditions preventing inhibition by photosynthetic $O_2$, thereby permitting increase in the yield of $H_2$ and making the process economical.

A further object, feature, or advantage of the present invention is to provide microorganisms capable of producing $H_2$ by enabling sufficient competition for electrons of mature HydA1 with enzymes utilizing the same electron donor to produce considerable amounts of $H_2$.

A further object, feature, or advantage of the present invention is to separate synthesis of pre-HydA1 from incorporation of the catalytic cluster into the HydA1 enzyme.

One or more of these and/or other objects, features, or advantages of the present invention will become apparent from the specification and claims that follow.

BRIEF DESCRIPTION OF THE DRAWINGS

Illustrative embodiments of the present invention are described in detail below with reference to the attached drawing figures, which are incorporated by reference herein and wherein:

FIG. 2 shows a schematic of the constructed transformation vectors with the synthetic gene cassettes.

FIG. 7 (A-B) shows the nucleotide sequence of HydA1 gene according to a particular embodiment of the invention.

FIG. 8 shows the nucleotide sequence of wild type HydA1 cDNA according to a particular embodiment of the invention.

FIG. 9 shows the nucleotide sequence of an optimized HydA1 cDNA according to a particular embodiment of the invention.

FIG. 10 shows the amino acid sequence of HydA1 according to a particular embodiment of the invention.

FIG. 11 shows the nucleotide sequence of a chimeric gene encoding a translational N-terminal fusion of an electron transfer protein PetF to HydA1 according to a particular embodiment of the invention.

FIG. 12 (A-B) shows the nucleotide sequence of a gene for constitutive expression of the hydrogenase HydA1 in C. reinhardtii according to a particular embodiment of the invention.

FIG. 13 (A-B) shows the nucleotide sequence of a pX-HydG chimeric gene according to a particular embodiment of the invention.

FIG. 14 (A-B) shows the nucleotide sequence of a pX-Hyd EF chimeric gene according to a particular embodiment of the invention.

DETAILED DESCRIPTION OF THE PREFERRED EMBODIMENT

Definitions

Figure 1A:
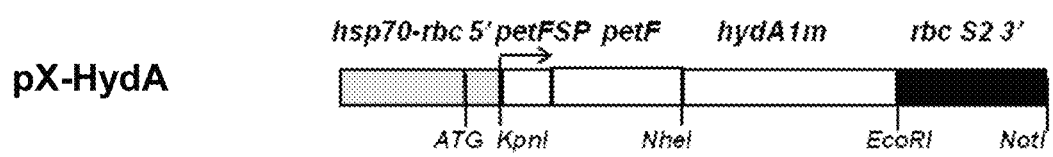
FIG. 1 (A-B) shows the schematic representations of the gene constructs according to an exemplary embodiment of the invention. (A) shows the synthesized hydA1 gene construct for constitutive expression of HydA1 in Chlamydomonast. SP, the petF signal peptide; petF, coding region for the cDNA of a ferredoxin; HydA1m, optimized coding region for the cDNA of HydA1 without the signal peptide, 5' promoter regions; 3' termination regions. (B) shows the synthesized hydGm and hydEFm gene constructs for inducible expression of HydG, HydE, and HydF in Chlamydomonas. SP, the FNR1 signal peptide; crgfp, the Chlamydomonas optimized GFP coding region; hydGm, hydEFm, optimized coding regions of cDNA for HydG, HydE, and HydF without the signal peptides, cyc6 5' and 3', Cyc6 promoter and termination region.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

As used herein, the term "mutant" comprises one or more, preferably one or several, deletions, substitutions or additions in the amino acid or nucleotide sequences of the proteins of the present invention, or homologues thereof. The mutant may include either naturally occurring mutants or artificial mutants.

Where the mutant is a protein or polypeptide, preferable substitutions are conservative substitutions, which are substitutions between amino acids similar in properties such as structural, electric, polar, or hydrophobic properties. For example, the substitution can be conducted between basic amino acids (e.g., Lys, Arg, and His), or between acidic amino acids (e.g., Asp and Glu), or between amino acids having non-charged polar side chains (e.g., Gly, Asn, Gln, Ser, Thr, Tyr, and Cys), or between amino acids having hydrophobic side chains (e.g., Ala, Val, Leu, Ile, Pro, Phe, and Met), or between amino acids having branched side chains (e.g., Thr, Val, Leu, and Ile), or between amino acids having aromatic side chains (e.g., Tyr, Trp, Phe, and His).

The term "conservatively modified variants" applies to both amino acid and nucleic acid sequences. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)).

As used herein "full-length sequence" in reference to a specified polynucleotide or its encoded protein means having the entire amino acid sequence of a biologically active form of the specified protein. Methods to determine whether a sequence is full-length are well known in the art including such exemplary techniques as northern or western blots, primer extensions, S1 protection, and ribonuclease protection. See, e.g., Plant Molecular Biology: A Laboratory Manual, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a sub-sequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. Examples of promoters under developmental control include promoters that preferentially initiate transcription at different points in the development of a microorganism, etc. A "cell type" specific promoter primarily drives expression in certain cell types in a life cycle. An "inducible" or "repressible" promoter is a promoter which is under environmental control. Examples of environmental conditions that may affect transcription by inducible promoters include anaerobic conditions, the presence of a specific molecule, or the presence of light. Cell type specific and inducible promoters constitute the class of "non-constitutive" promoters. Examples of inducible promoters include Cu-sensitive promoter, Gal1 promoter, Lac promoter, while Trp promoter, Nit1 promoter and cytochrome c6 gene (Cyc6) promoter are among repressible promoters. A "constitutive" promoter is a promoter which is active under most environmental conditions. Examples of constitutive promoters include Ubiquitin promoter, actin promoter, PsaD promoter, RbcS2 promoter, heat shock protein (hsp) promoter variants, and the like.

A skilled person appreciates a promoter sequence can be modified to provide for a range of expression levels of an operably linked heterologous nucleic acid molecule. Less than the entire promoter region can be utilized and the ability to drive expression retained. However, it is recognized that expression levels of mRNA can be decreased with deletions of portions of the promoter sequence. Thus, the promoter can be modified to be a weak or strong promoter. A promoter is classified as strong or weak according to its affinity for RNA polymerase (and/or sigma factor); this is related to how closely the promoter sequence resembles the ideal consensus sequence for the polymerase. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

As used herein "recombinant" or "engineered" includes reference to a cell or vector that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C. for 20 minutes.

Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138:267-284 (1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of the complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acids Probes, Part I, Chapter 2, Ausubel, et al., Eds., Greene Publishing and Wiley-Interscience, New York (1995). In general a high stringency wash is 2×15 min in 0.5×SSC containing 0.1% SDS at 65° C.

The term "expression", as used herein, refers to the transcription and stable accumulation of coding (mRNA) or functional RNA derived from a gene. Expression may also refer to translation of mRNA into a polypeptide. "Overexpression" refers to the production of a gene product in transgenic organisms that exceeds levels of production in normal or non-transformed organisms.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

As used herein, "vector" includes reference to a nucleic acid used in transfection of a host cell and into which can be inserted a polynucleotide. Vectors are often replicons. Expression vectors permit transcription of a nucleic acid inserted therein. The vectors may contain a selectable marker or reporter gene necessary for screening transformed cells of interest. Examples of the selectable marker include, but are not limited to, drug resistant genes such as kanamycin resistant gene (NPTII), hygromycin resistant gene (htp), biarafos resistant gene, carbenicillin resistant gene, and the like. Examples of the reporter gene include, but are not limited to, GFP (green fluorescence protein) gene, GUS (.beta.-glucuronidase) gene, luciferase gene, and .beta.-galactosidase gene.

As used herein, the term "microanaerobic," "microanaerobiosis," "microanaerobiotic" and "microanaerobic conditions" refers to conditions or states with broad parametric limits. Such conditions or states include reference to culturing microbial cells in an anaerobic system with aerobic microniches. The actual supply of $O_2$ in the gas phase does not define the availability of dissolved $O_2$ to the individual cells. $O_2$ availability is a complex function, which is affected by numerous parameters including the $O_2$ input rate, the stirring rate, the chemical composition of the medium, the biomass concentration, and the specific respiratory activity of the organism. (Alexeeva, S., Hellingwerf, K. J. and Teixeira de Mattos M. J. (2002), Quantitative assessment of $O_2$ availability: perceived aerobiosis and its effect on flux distribution in the respiratory chain of Escherichia coli. J. Bacteriol., 184 (5): 1402). Under aerobic conditions $O_2$ supply is sufficient to support fully oxidative catabolism (specifically its respiratory activity). At low $O_2$ concentrations, $O_2$ availability to the individual cells becomes sparse, and the majority of cells switch to anaerobic processes (anoxic catabolism). Under microanaerobic conditions, the individual cells predominantly undergo anoxic catabolism.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. Further, the terms are meant to include one-celled organisms capable of surviving anaerobic conditions.

The term "autotrophic," as used herein, refers to an organism that is capable of producing complex organic compounds (carbohydrates, fats, and proteins) from simple inorganic molecules using energy from light (by photosynthesis) and/or inorganic chemical reactions. The term "photoautotrophic," as used herein, refers to an organism capable of producing complex organic compounds (carbohydrates, fats, and proteins) from simple inorganic molecules, which include carbon dioxide and other nonreduced sources of carbons, such as bicarbonate, using energy from light (by photosynthesis). The term "mixotrophic," as used herein, refers to cells or organisms capable of using a mix of different sources of energy and carbon, for example, using phototrophy (meaning growth using energy from light) and chemotrophy (meaning growth using energy by the oxidation of electron donors), or between chemical autotrophy and heterotrophy. The term "heterotrophic," as used herein, refers to an organism that does not produce its own food and must acquire some of its nutrients from the environment, e.g., in the form of reduced carbon substrates.

General Methods for Engineering Microorganisms for Enhanced $H_2$ Production

The present invention utilizes recent breakthroughs in genome engineering to enable microorganisms to synthesize $H_2$ in large quantities. The benefits of the present invention are achieved in three aspects: (i) overexpression of $H_2$ase to establish sufficient competition for electron donor under microanaerobic or anaerobic conditions; (ii) separation of the production of pre-$H_2$ase from its maturation to enable accumulation of pre-$H_2$ase and rapid increase of mature $H_2$ase upon synthesis of maturation proteins; and (iii) enabling pre-$H_2$ase maturation to $H_2$ase only under anaerobic conditions to prevent $O_2$ inhibition of the mature $H_2$ase.

The mature $H_2$ase is assembled in a stepwise manner [59]. The polypeptide is synthesized, and classical $O_2$-tolerant FeS clusters are incorporated. Consequently, pre-$H_2$ase is $O_2$-tolerant. Moreover, pre-$H_2$ase is stable for many hours and can form the active enzyme upon induction of the maturation genes [60]. Therefore, it is an object of the present invention to separate synthesis of pre-$H_2$ase and the catalytic cluster.

In another aspect of the invention, genes encoding maturation proteins are engineered for inducible expression under microanaerobic or anaerobic conditions. When microanaerobic conditions are reached in a cell, expression of the maturation proteins is activated. The catalytic cluster is then safely incorporated into pre-$H_2$ase completing the maturation process. Initiation of transcription/translation of the maturation genes can be adjusted by selecting a promoter inducible with desirable concentrations of $O_2$. Because synthesis of pre-$H_2$ase continues throughout the photosynthetic phase, a significant number of mature $H_2$ase molecules are produced soon after microanaerobiotic conditions are reached. In this aspect, the present invention achieves the object of enabling sufficient competition for electrons with $H_2$ase competitors such as ferredoxin:NADP+-oxidoreductase (FNR1) to produce considerable amounts of $H_2$.

Generally, a recombinant $H_2$ase gene alone or together with genes encoding recombinant maturation proteins are expressed in a microorganism, which is capable of surviving microanaerobic or anaerobic conditions. The recombinant genes encoding the recombinant proteins can be synthesized or made using standard molecular biology methods. These genes are inserted into transformation vectors, suitable for a specific microorganism, and the vectors are used to transform the microorganism, e.g., introduce the recombinant genes into the microorganism, thus, creating a transformed (recombinant) microorganism.

According to one aspect of the invention, engineered microorganisms are characterized by increased $H_2$ production, the level of which is higher than that of wild types. This character of the microorganisms is achieved by overexpressing a recombinant DNA coding for the $H_2$ase enzyme HydA or a homologue thereof in the microorganism. As used herein, the term "HydA" is an abbreviation of $H_2$-forming [FeFe]-$H_2$ase.

HydA enzymes are $O_2$ sensitive. In particular, a catalytic cluster of HydA is $O_2$-sensitive. This invention separates synthesis of pre-HydA, the enzyme form which lacks the catalytic cluster, from maturation of pre-HydA into HydA. Maturation involves insertion of the catalytic cluster into pre-HydA. The catalytic cluster is synthesized by maturation proteins. For example, C. reinhardtii possesses three maturation proteins HydE, HydF, and HydG, which are encoded by hydEF and hydG. Separation of pre-HydA synthesis from maturation is achieved by differential expression of HydA and maturation proteins.

HydA is overexpressed in the engineered microorganism while expression of maturation proteins is limited to microanaerobic or anaerobic conditions. Accordingly, pre-Hyd accumulates in the recombinant host cells in large amounts, which facilitate rapid maturation upon availability of the catalytic clusters. Meanwhile, synthesis of the catalytic cluster occurs upon establishment of microanaerobic or anaerobic conditions. Consequently, maturation of pre-HydA occurs under microanaerobic or anaerobic conditions preventing inhibition by $O_2$.

The inventor has successfully engineered a highly regulated gene for constitutive expression. Overexpression of the key gene in $H_2$ synthesis in C. reinhardtii, hydA1, was the first necessary step for developing a continuous process for high-volume, commercial $H_2$ production by algae. $H_2$ production can clearly be increased through proper balancing in expression of HydA and maturation genes through the choice of appropriate promoters. Genes can also be added to accelerate establishment of microanaerobiosis without disturbing the function of mitochondria. Proteins participating in electron transfer (electron donors), which are capable of supplying electrons to the recombinant HydA, have to be naturally occurring or introduced into the host cells. Genes encoding electron donors can be manipulated to further increase electron flow toward HydA1 under microanaerobic and anaerobic conditions. In one aspect of the invention, the recombinant HydA and maturation proteins are co-localized with the employed electron donor. In a preferred embodiment, signal peptides of proteins naturally co-localized with the electron donor are incorporated into the recombinant genes to target the recombinant proteins to the same subcellular location.

Engineered recombinant nucleic acid molecules are introduced in host cells by transformation, and recombinant host cells are selected using standard molecular biology methods and tested for $H_2$ yields. Total yield is determined by gas chromatography (GC) or mass spectrometry (MS).

Hydrogenases $H_2$ases catalyze a bidirectional reaction $2H^+ + 2e^- \leftrightarrow H_2$. A $H_2$ uptake reaction splits a $H_2$ molecule into two protons and two electrons. A $H_2$ forming reaction combines two protons and two electrons into a $H_2$ molecule. $H_2$ forming Hoses are capable of predominantly catalyzing H2 synthesis and producing significant amounts of $H_2$. $H_2$-forming $H_2$ases are not common in nature, compared to $H_2$ases that predominantly mediate $H_2$ uptake activity. C. reinhardtii expresses two $H_2$-forming $H_2$ase encoding genes, isoform1 (HydA1) and isoform2 (HydA2) (GenBank Accession No: AAL23572 and AAL23573), but the HydA1 protein appears to be the primarily active $H_2$ase isoform in the green alga. Clostridium bacterial species possess HydA enzymes, which catalytic domains are homologous to C. reinhardtii HydA1, for example C. pasteurianum and Clostridium acetobutylicum HydA enzymes (GenBank Accession No: AAA23248 and NCBI Reference Sequence: NP_346675.1, respectively). Algae Sceneaesmus obliquus and 'Chlorella fusca and bacterium Fusobacterium ulserans possess HydA enzymes as well, and BLAST search identifies several homologues from a variety of bacterial and algal species, which function has not been experimentally tested.

According to one aspect of the invention, HydA can be engineered to increase $H_2$ production by optimizing the nucleic acid molecule for expression in the presence of $O_2$. In a preferred embodiment, the recombinant HydA gene comprises a nucleic acid molecule encoding *C. reinhardtii* HydA1 or a homologue thereof, including but not limited to *C. pasteurianum* HydA (GenBank Accession No: AAA23248.1). Because the wild-type HydA encoding genes are tightly regulated, especially by $O_2$ [83, 84], the protein encoding region has to be optimized to enable expression in the presence of $O_2$. A HydA mRNA sequence is analyzed to identify regulatory motifs and structures. Software algorithms for secondary structure prediction of single-stranded RNA and DNA sequences, such as RNAfold and Mfold, are employed to identify complex secondary structures in the mRNA. Regulatory motifs can be identified using a motif database such as the DNASIS MAX DNA motif database and literature search. The identified structures and motifs, which are thought to be involved in transcription/translation regulation and prevent constitutive expression, are next modified via silent nucleotide substitutions. The optimized sequence is tested by expressing the gene under a promoter which is operational in the presence of $O_2$ in a selected host cell. The below Table A shows examples of putative regulatory motifs which can repress HydA expression in the presence of $O_2$.

TABLE A

Exemplary putative regulatory motifs

| Regulatory Motif | Nucleotide Sequences |
|---|---|
| E_box_CS | CAGGTGGC |
| Alpha_INF.2 | AARKGA |
| CRE.1 | CGTCA |
| CREB_CS | ACGTCA |
| SIF_core_RS | CCCGTC |

In a further embodiment, the nucleic acid sequence is optimized for expression in a selected microorganism. Examples of optimization include codon optimization, targeted mutagenesis to enable expression in the presence of $O_2$, promoter swapping, replacing a signal peptide, and the like.

Promoter selection is guided to enable overexpression of the recombinant HydA1 in the presence of $O_2$ and co-localize the recombinant HydA1 with maturation proteins and a suitable electron donor. Examples of the promoter include, but are not limited to, Hsp70 promoter, RbcS2 promoter, PsaD promoter, tubulin promoter, actin promoter, and the like. A terminator may be linked to the 3'-end of the optimized DNA. Examples of the terminator include, but are not limited to, RbcS2 terminator, PsaD terminator, tubulin terminator, and the like.

As used herein, the term "homologue" means a protein from any microorganism other than the host cell, which protein comprises an amino acid sequence homologous to that of a known $H_2$-forming $H_2$ase, including but not limited to *C. reinhardtii* HydA1 or the catalytic domain of *C. pasteurianum* HydA. The term also includes HydA enzymes from *C. reinhardtii* and *C. pasteurianum* that have been modified, chimerized, or otherwise altered while retaining the activity of the endogenous protein.

In this invention, the HydA or homologues thereof may be mutated as long as the mutants have $H_2$ase activity when they are expressed in microorganisms.

The amino acid and nucleotide sequences of $H_2$-forming $H_2$ases or homologue proteins and DNAs encoding them are available from known databases such as NCBI GenBank (USA), EMBL (Europe), etc.

Specifically, HydA or homologue proteins or mutant proteins thereof comprise an amino acid sequence as shown in SEQ ID NO:4 or amino acid sequences having an at least 50%, preferably at least 70-85%, more preferably at least 86-89%, even more preferably at least 90-98% identity to the amino acid sequence of SEQ ID NO:4 and having $H_2$ase activity.

The present invention provides isolated nucleic acid molecules for recombinant HydA genes and variants thereof. The full-length nucleic acid sequence for this gene encoding an HydA, which is codon- and expression-optimized for *C. reinhardtii* is shown in SEQ ID NO:3. In a further embodiment, the present invention provides a nucleic acid molecule encoding an HydA, homologue proteins, or mutant proteins comprising: (i) a nucleotide sequence as shown in SEQ ID NO:3, or nucleotide sequences having an at least 50%, preferably at least 70-85%, more preferably at least 86-89%, yet more preferably at least 90-98% identity to the nucleotide sequence of SEQ ID NO: 3; (ii) nucleotide sequences encoding the HydA1 protein as defined above; or (iii) nucleotide sequences capable of hybridizing with a nucleotide sequence complement to the nucleotide sequence of SEQ ID NO: 3, under stringent conditions, wherein the nucleotide sequences (i), (ii) and (iii) code for proteins having an activity of increasing a level of $H_2$ production at least by two-fold when compared with wild types.

In another embodiment, the nucleic acid encodes a $H_2$-forming $H_2$ase operably linked to a constitutive promoter and an electron source, such as a ferredoxin, In one aspect, the nucleic acid comprises: (i) a nucleotide sequence as shown in SEQ ID NO:5, or 6, or nucleotide sequences having an at least 50%, preferably at least 70-85%, more preferably at least 86-89%, yet more preferably at least 90-98% identity to the nucleotide sequence of SEQ ID NO:5, or 6; (ii) nucleotide sequences encoding the HydA1 protein as defined above; or (iii) nucleotide sequences capable of hybridizing with a nucleotide sequence complement to the nucleotide sequence of SEQ ID NO:5, or 6, under stringent conditions, wherein the nucleotide sequences (i), (ii) and (iii) code for proteins having an activity of increasing a level of $H_2$ production at least by two-fold when compared with wild types.

The present invention also provides nucleotide sequence fragments comprising at least 50 contiguous nucleotides of the sequence of SEQ ID NO: 3. More preferably, the fragments of nucleic acid sequences contain at least 30, 40, 50 or even more contiguous nucleotides.

It is understood that the compositions and methods described herein are predictive of applicability more broadly to other $H_2$ases and maturation proteins, including any bacterial, cyanobacterial, and algal $H_2$ases and maturation proteins.

Maturation Proteins

According to one aspect of the present invention, maturation of pre-HydA is permitted under microanaerobic or anaerobic conditions, thereby preventing inhibition of the $O_2$-sensitive HydA catalytic cluster. *C. reinhardtii* expresses three maturation proteins, which are responsible for maturation of HydA1: HydE, HydF, and HydG maturations proteins (GenBank Accession No: AAS92601 and AAS92602).

In one embodiment of the invention, expression of at least one maturation protein is preferably permitted under microanaerobic or anaerobic conditions. In another embodiment, each maturation protein can be engineered by optimizing the nucleic acid molecule for expression under microanaerobic or anaerobic conditions. In a more preferred embodiment, the recombinant maturation protein gene or genes comprise nucleic acid molecules encoding maturation proteins *C. reinhardtii* HydE, HydF, HydG or their homologues including, but not limited to, as *C. pasteurianum* maturation proteins. (NCBI Accession No: YP_007941498, YP_007940932 and WP_003448099). In another embodiment, each nucleic acid sequence is optimized for expression in a selected microorganism. Examples of optimization include codon optimization, targeted mutagenesis to optimize expression under microanaerobic or anaerobic conditions, promoter swapping, replacing a signal peptide, and the like.

In a preferred embodiment, promoters for expression of maturation proteins are selected in order to provide for expression of the recombinant genes encoding maturation proteins at relatively low levels, thereby preventing cell toxicity. This is because recombinant HydE and/or HydF may be especially toxic to a host cell if expression is too high. In a more preferred embodiment, the selected promoter may provide tight regulation of the recombinant HydE and/or HydF expression to minimize cell toxicity. Examples of the inducible promoters include, but are not limited to, Cyc6 promoter, Lac promoter, Nit1 promoter, and the like. Cyc6 promoter is anaerobiosis- and Cu-inducible. In one embodiment of the invention, activity of Cyc6 promoter can be easily modulated to tune levels of expression in an algal host cell. A terminator may be linked to the 3'-end of the optimized DNA. Examples of the terminator include, but are not limited to, RbcS2 terminator, Cyc6 terminator, tubulin terminator, and the like.

In addition, the optimization of the recombinant genes preferably requires replacement or elimination of not only the leading signal sequence in the hydEF gene (GenBank Accession No: AY582739), but also the internal signal peptide sequence located at the N-terminus of the HydF encoding sequence. This step is necessary to co-localize both recombinant maturation proteins, HydE and HydF, with the recombinant HydA1.

The present invention provides isolated nucleic acid molecules for the recombinant hydE, hydF and hydG genes and variants thereof. In one embodiment, the full-length nucleic acid sequences for these genes encoding HydE, HydF, and HydG, which are codon- and expression-optimized for *C. reinhardtii*, are shown in SEQ ID NO:9, 10, and 11.

In a further embodiment, the present invention provides recombinant nucleic acid molecules encoding HydE, HydF, and HydG, homologue proteins, or mutant proteins comprising or consisting: (i) nucleotide sequences as shown in SEQ ID NO:9, 10, or 11 or nucleotide sequences having an at least 50%, preferably at least 70-85%, more preferably at least 86-89%, yet more preferably at least 90-98% identity to the nucleotide sequence of SEQ ID NO: 3, 5, or 6; (ii) nucleotide sequences encoding the HydE, HydF, and HydG proteins as defined above; or (iii) nucleotide sequences capable of hybridizing with a nucleotide sequence complement to the nucleotide sequences of SEQ ID NO: 9, 10, or 11 under stringent conditions, wherein the nucleotide sequences (i), (ii) and (iii) code for proteins having an activity of maturation proteins and increasing a level of $H_2$ production at least by two-fold when compared with wild types.

Electron Donors

The compositions and methods of the present invention encompassing expression of a recombinant HydA gene and maturation proteins may be utilized in conjunction with any compatible electron source to direct electron flux toward $H_2$ production. More specifically, the compositions and methods may be used with any electron donor system that is compatible with HydA enzymes, for example those possessed by *C. reinhardtii* and *C. pasteurianum*. Such an electron donor systems constitute a "compatible electron donor."

Compatible electron donors include, but are not limited to, any reduced ferredoxin that can mediate the transfer of electrons to HydA under microanaerobic or anaerobic conditions. Ferredoxin proteins of plant (spinach) and algae (*C. reinhardtii* and *S. obliquus*) were capable of reducing purified *S. obliquus* HydA as shown in U.S. Pat. No. 6,858,718 B1. A fusion of HydA and ferredoxin was shown to generate $H_2$ in vitro (U.S. Pat. No. 8,124,347 B2). However, was no in vivo demonstration before this invention. The ferredoxin can be reduced though a variety of pathways known to a person of skill in the art, including photosynthesis, fermentation, respiration, the citric acid cycle, anaerobic metabolism, and/or glycolysis. Therefore, the compositions and methods of the present invention are predicted to function in $H_2$ production in conjunction with these systems, and in organisms expressing them.

In one aspect of this invention, a recombinant $H_2$-forming $H_2$ase is targeted in a host cell to co-localize it with a compatible electron donor. Overexpression of the $H_2$-forming $H_2$ase facilitates redirection of electrons toward $H_2$ production. It is also understood that the recombinant $H_2$-forming $H_2$ase of the present invention can be directly fused with a compatible electron donor. The SEQ ID NO:5 provides an example of such a chimeric nucleic acid molecule which encodes the recombinant HydA1 with an N-terminal fusion of a *C. reinhardtii* ferredoxin PetF. Furthermore, two or more electron donors can be fused to the recombinant $H_2$-forming $H_2$ase where the compatible electron donor is directly fused to the $H_2$-forming $H_2$ase, and a second electron donor is fused directly to the compatible electron donor. Such a tandem electron donor construction is preferred when the compatible electron donor is not readily available in the reduced form under microanaerobic or anaerobic conditions in the selected host cell.

In another aspect of the invention, an enzyme which competes with the recombinant $H_2$-forming $H_2$ase for the compatible electron donor may be attenuated. The competing enzyme of choice is highly active in the host cell under microanaerobic or anaerobic conditions. In a preferred embodiment, the competing enzyme is attenuated to reduce its catalytic activity by at least 30% and no more than 70% because higher attenuation can trigger an alternative metabolic pathway and reduce electron supply to the recombinant $H_2$-forming $H_2$ase. Methods of enzyme attenuation are known among skilled in the art, including, but not limited to, generating mutations in the endogenous gene encoding the competing enzyme, thereby altering amino acids which interact with the employed electron donor.

Microorganisms

A variety of microorganisms are suitable for use in the present invention, and can be transformed to produce $H_2$. Microorganisms include prokaryotic (Archaea and Bacteria) and eukaryotic (algae, yeast, filamentous fungi, and protozoa) microbial species. Prokaryotic organisms suitable for use in the present invention include, but are not limited to, cyanobacteria. Eukaryotes especially suited to the present invention include algae, due to their ability to convert sunlight and waste $CO_2$ directly into $H_2$ and other useful products. Algae are among the fastest growing and most proficient $CO_2$-sequestering organisms, and can be grown on nonagricultural land and withstand extreme environmental conditions.

Archabacteria and bacteria include, but are not limited to, *Acetobacter, Bacillus, Chlorobium, Chromatium, Chloroflexus, Clostridium, Escherichia, Methanobacterium, Nitrobacter, Nitrococcus, Oscillochloris, Pseudomonas, Rhodobacter, Rhodospirillum, Rhodopseudomonas, Phodopila, Thiocyctis,* etc.

Cyanobacteria and algae include *Aulacoseira, Anabaena, Cedogoniales, Chaetoceros, Chaetopeltidale, Chaetophora, Chlamydomonas, Chlorococcum, Chrorella, Cyclotella, Cylindrocapsa, Dunaliella, Melosira, Microcystis, Microspora, Prorocentrum, Alexandrium, Navicula, Nostoc, Skeletonema, Spirogyra, Sphaeroplea, Synechocystis, Synechococcus, Pseudo-nitzschia, Thalassiosira, Thermosynechococcus, Volvox,* etc.

Examples of other suitable microorganisms include, but are not limited to, *Botriococcus braunii, Chlamydomonas reinhardtii, Chlorella fusca,* and *Dunaliela salina* (algae), *Synechococcus* sp., *Synechocystis* sp., *Thermosynechococcus elongates* (cyanobacteria), *Chlorobium tepidium, Rhodospirillum rubrum, Rhodobacter capsulatus* (bacteria), *Saccharomyces cerevisiae, Pichia pastoris, Schizosaccharomyces pombe* (yeast and fungi).

In a preferred embodiment, a suitable organism for engineering according to the invention is capable of surviving under microanaerobic or anaerobic conditions, in order to account for the $O_2$ sensitivity of mature HydA.

Transformation of Selected Microorganisms

The present invention also relates to a host cell transformed with a recombinant nucleic acid molecule of the present invention. Transformation of appropriate cell hosts is accomplished by well-known methods that typically depend on the cell. According to an aspect of the present invention, transformed microorganisms can be prepared by transforming the cells with a vector or vectors comprising nucleotide sequences encoding an $H_2$-forming $H_2$ase and maturation proteins, or homologues thereof. The transformed microorganism can be produced by a method comprising introducing a vector or vectors comprising the nucleotide sequences into cells of a microorganism to obtain transformed cells, and selecting a transformed cell expressing the DNA at the desired levels, from the obtained transformed cells.

For transformation of *C. reinhardtii* (algae), transformation can be performed by methods well known in the art such as electroporation, glass beads, particle gun, and the like. Briefly, when using the glass bead method (Kindle, 1990, Proc Natl Acad Sci USA, 87: 1228-1232) *C. reinhardtii* is grown in tris-acetate-phosphate (TAP) medium (Harris, 2009, The *Chlamydomonas* sourcebook: introduction to *Chlamydomonas* and its laboratory use, 2nd Ed. Access Online via Elsevier, Vol. 1, 444 p.) to a mid-log growth phase (10E6 cells/mL). Cells are concentrated, and approximately 10E8 cells are combined with a digested vector and glass beads. The mixture is vigorously vortexed, and cells are plated on agar TAP containing a selective agent. Selections are typically performed on 10 µg/mL hygromycin or paromomycin, or 75 µg/mL spectinomycin. Transformed colonies appear after one week of culturing under selective conditions. Examples of *Chlamydomonas* transformation vectors include pJR38 and/or pChlamy_1. Genetic transformation of algae is widely considered cumbersome due to inconsistent results and transgene instability, which depend on a particular recombinant nucleic acid molecule [61]. Each recombinant nucleic acid sequence has to be optimized for transgene stability in the host cell.

*Synechococcus* sp. (cyanobacteria) can be transformed using electroporation, chemically induced transformation, and the like. Briefly, when using chemical induction, *Synechococcus* sp. is grown in Medium A supplemented with 5 g/L NaNO3 to approximately 10E8 cells/mL. Cells are combined with 1-10 µg/mL of a transformation vector dissolved in 150 mM NaCl and 15 mM Na citrate at a 1:10 ratio and incubated at 30° C. for 3 h. The cells are diluted in 2.5 mL of Medium A with 0.6% agarose at 45 30° C. and plated on agar Medium A containing a selective agent. The later is typically 200 µg/mL kanamycin or 10 µg/mL spectinomycin.

According to another aspect of the invention, transformation of other types of cells, including bacterial cells and fungal cells, can be carried out according to methods well known in the art, including the use of viral vectors, plasmid vectors, electroporation, and the like. Numerous methods for bacterial transformation have been developed, including biological and physical, bacterial transformation protocols. See, for example, Sambrook et al., Molecular Cloning A Laboratory Manual, 1989, Cold Spring Harbor Laboratory Press, Ausubel et al., Current Protocols in Molecular Biology, 1994, John Wiley & Sons, etc.

Each recombinant sequence is optimized individually for expression in a specific microorganism. Examples of optimization include codon optimization, targeted mutagenesis of nucleic acid sequences to increase or limit expression, promoter swapping and tuning, adding or removing regulatory sequences including signal peptides, and the like. Additional modifications may include fusions between above described polypeptides and heterologous peptides/polypeptides I to improve purification and/or detection. Examples of such fusion polypeptides include $His_6$-tag, green fluorescence protein, and luciferase.

$H_2$ Detection

As is well known in the art, HydA activity can be measures using gas chromatography (GC) or mass spectrometry (MS). As an example, see Hemschemeier, A., A. Melis, and T. Happe, Analytical approaches to photobiological hydrogen production in unicellular green algae. Photosynthesis Research, 2009. 1-2: p. 523-540. Two main bioassays are employed, an in vitro $H_2$ase activity bioassay and an in vivo $H_2$ase activity bioassay. Briefly, the in vitro bioassay allows direct measurement of $H_2$ase activity independent of availability of an electron donor in microbial cells because activity is measured in whole-cell extracts in a buffer which contains an electron donor, reduced methyl viologen[29]. Cells are cultured to induce HydA maturation, transferred in a gas-tight container, and lysed under anaerobic conditions. The electron donor is added, and reaction mixture is incubated at 37° C. in the dark on mild shaking for 15 min. Overhead space is sampled using a gas-tight syringe and $H_2$ concentrations are measured by GC or MS.

The in vivo bioassay measures HydA activity in a host cell that is a function of levels of maturated HydA and electron supply. Cells are grown to accumulate energetic resources which can be used for $H_2$ production. HydA maturation is induced under anaerobic conditions. Next, cells are transferred to a gas-tight container and cultured under preferred $H_2$ production conditions such as S-deprivation. Overhead space is sampled using a gas-tight syringe and $H_2$ concentrations are measured by GC or MS.

H₂ Production

Current yields of $H_2$ in microorganisms are too low for commercial production (at 10.4 μmol per mg chlorophyll per hour for *C. reinhardtii*, as described in U.S. Pat. No. 7,501,270 B2). Currently, S-deprivation based methods employ algae *C. reinhardtii* starved on S and with depleted photosynthetic S-containing proteins as described in U.S. Patent Pub. No. 20010053543, which is incorporated herein in its entirety. When exposed to light, depleted cells use HydA as an electron sink.

In one aspect, the invention provides engineered microorganisms that produce $H_2$ in large quantities. In one embodiment, a continuous process for increased production of $H_2$ is achieved with engineered microorganisms via balancing growth and production phases, where the production phase is limited to microanaerobic or anaerobic conditions. In the preferred invention, cultures are cycled between growth and production phases. Conditions of the growth phase are optimized for fast growth and accumulation of energetic molecules which will be used for $H_2$ production. Conditions of the production phase are optimized to prevent inhibition of the maturated recombinant HydA1, and also to maximize supply of electrons to the HydA1. Condition optimizations can be completed by employing known culture and fermentation techniques. Specific optimization parameters for the growth phase may include cell density, dilution rates, mixing, temperature, concentrations of nutrients, etc. The production phase may require optimization of removal rates for $H_2$ and compounds/metabolic products which inhibit a specific metabolic pathway used for electron supply.

All references cited herein are incorporated herein by reference in their entirety. Examples are provided by way of exemplification and are not intended to limit the scope of the invention.

EXAMPLES

Example 1

Chimeric Gene Encoding HydA1 Under a Strong Constitutive Promoter

The inventor constructed a gene for constitutive expression of the synthetic $H_2$ase HydA1 in *C. reinhardtii* (FIG. 1A). Continuous expression was chosen because pre-HydA1 is stable under aerobic conditions for several hours [82]. The new HydA1 expression construct was designed to increase accumulation of pre-HydA1 in the presence of $O_2$, and the designed sequence was synthesized.

Because the wild-type hydA1 is tightly regulated, especially by $O_2$ [83, 84], the HydA1 encoding region was optimized to enable constitutive expression, in particular, the HydA1 cDNA region (hydA1) (SEQ ID NO:2) without the signal peptide (corresponding to amino acids 53-457 of hydAI, GenBank ID AF289201). The hydA1 mRNA sequence was analyzed to identify regulatory motifs and structures. Two software algorithms for secondary structure prediction of single-stranded RNA and DNA sequences, RNAfold and Mfold, identified complex secondary structures in the hydAI mRNA. Several putative regulatory motifs were identified within the mRNA sequence with the DNASIS MAX DNA motif database. These structures and motifs were thought to be involved in transcription/translation regulation and prevent constitutive expression of the chimeric gene. To enable constitutive expression, the hydAI mRNA sequence, in particular, the protein encoding region without the signal peptide, was optimized iteratively by removal of selected structures and putative regulatory motifs via silent nucleotide substitutions. Next, codon optimization was performed using proprietary software. The optimized hydA1m sequence was then used for subsequent aspects of the invention (SEQ ID NO:3).

Example 2

N-Terminal Fusion of an Electron Donor to Chimeric HydA1

Recent findings demonstrated that an N-terminal fusion of an electron donor ferredoxin to HydA1 redirected electrons toward the chimeric HydA1 in vitro in the presence of HydA1 competitors [81]. Almost no electrons were directed to HydA1 without ferredoxin fusion in that report. To facilitate redirection of electrons toward $H_2$ evolution in algal cells, the inventor designed a chimeric gene encoding a translational N-terminal fusion of an electron transfer protein PetF to HydA1. The *C. reinhardtii* petF gene is nuclear encoded similar to hydA1 and contains a 29-residue-long signal peptide (NCBI Accession No: XM_001692756.1). The signal peptide is predicted by the ChloroP 1.1 program for plastid targeting signal peptides. The coding sequences for the two proteins were linked by a 20-residue-long linker, the petF stop codon was removed, and the 3' RbcS2 terminator was added after the hydA1m stop codon. Specific restriction sites were added on the ends of the construct for subcloning into a transformation vector. Then SP-petF-hydA1m-3'RbcS2 gene cassette synthesis was performed by Life Technologies Co. (Carlsbad, Calif.) (FIG. 1A). The synthetic cassette was subcloned into pChlamy_1 (Life Technologies Co.: Carlsbad, Calif.) in a transcriptional/translational frame with a Hsp70/RbcS2 promoter resulting a transformational vector pCh-HydA using standard molecular biology methods (SEQ ID NO: 6).

Example 3

Chimeric Genes Encoding HydA1 Maturation Proteins

Figure 1B:
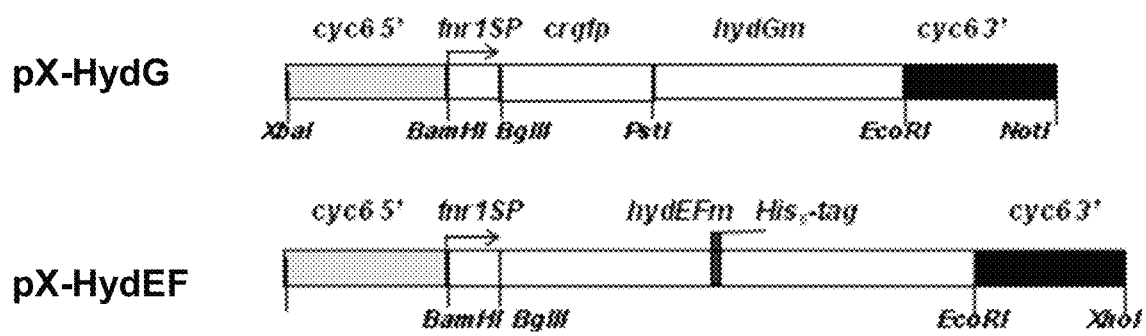

The genes for the maturation proteins, hydEF and hydG, are also nuclear encoded and tightly regulated [85] (Genbank Accession No: AY582739 and AY582740; cDNA: SEQ ID NO: 7, 8). The chimeric genes hydEFm and hydGm were designed following the above scheme. The mRNA analysis revealed numerous putative regulatory motifs and secondary structures in both mRNA sequences. Each protein encoding nucleic acid sequence was modified to remove selected regulatory motifs and structures via silent nucleotide substitutions. A putative signal peptide was identified at the N-terminus of the HydF encoding sequence. The later was removed as well. The produced synthetic sequences for hydEm, hydFm, and hydGm are shown in SEQ ID NO: 9, 10, and 11, correspondingly. The native signal peptides were identified and replaced with the signal peptide of a HydA1 competing enzyme, ferredoxin:NADP+-oxidoreductase (FNR1) [81]. The wild-type signal peptides were replaced because their sequences contain a number of putative regulatory motifs. Replacement with a signal peptide of a constitutively expressed gene would prevent repression of the transgenes. The fnr1 gene contains a 25-residue-long signal peptide with one intron. Because of an important role of a first intron, the unmodified genomic DNA sequence encoding the FNR1 signal peptide was added at the N-terminus of HydG and HydEF encoding regions to replace the native signal peptides. The Chlamydomonas codon optimized GFP encoding sequence [86] was added to the modified hydG after the signal peptide in the translational frame. A His$_6$-tag was added to hydEFm after the first signal peptide also. An anaerobiosis-inducible promoter and terminator of an intronless gene c6 (Cyc6) flanked both the hydGm and hydEFm encoding regions [87]. The Cyc6 promoter is rapidly induced by anaerobiosis and produces moderate levels of protein expression in Chlamydomonas [88]. The designed maturation protein encoding sequences were synthesized and subcloned into intermediate plasmids (FIG. 1B) (SEQ ID NO: 12-13).

Example 4

Transfer Gene Cassettes in C. reinhardtii Transformation Vectors

Synthesized gene cassettes were inserted into transformation vectors for Chlamydomonas transformation pJR38 [24] and pChlamy_1 [86]. The vector pChlamy_1, offers a hygromycin resistance selectable marker, while pJR38 carries a paromomycin resistance marker. Introduction of the chimeric genes into algae using transformation vectors with different antibiotic resistance would facilitate selection of a production strain expressing all synthetic genes. The chimeric genes were combined into sets of two transformation vectors enabling selection on two different antibiotics and visual detection of transgene expression via fluorescent protein markers (FIG. 2). The chimeric hydGm gene was subcloned into pCh-HydA at the 3' terminus of the hydAm cassette, in the opposite orientation, to generate pCh-HydA-HydG. The hydEFm gene cassette was inserted in pJR38 to replace a GFP cassette generating pJR38-HydEF. The intermediate plasmids and vectors were transformed into E. coli Top 10 strain and verified by restriction analysis. After the expected restriction digest analysis confirmed the expected restriction maps, the synthesized sequences and their orientation in the vectors were verified by sequencing.

Example 5

Intermediate Strains Transformed with the Chimeric HydA1 and HydG Genes

To introduce the engineered genes, nuclear transformation of Chlamydomonas strain UVM11 was performed by the glass bead method [89]. Two independent transformation experiments were performed for pCh-HydA and pCh-HydA-HydG, with pChlamy_2 used as a control transformation vector. Algal cells after transformation were incubated for four hours in liquid TAP medium[90] without antibiotic and plated on TAP containing 10 and 30 µg mL$^{-1}$ hygromycin.

Numerous colonies were obtained for all three vectors (Table 2). Several colonies maintained a relatively high growth rate on liquid TAP with 30 µg mL$^{-1}$ hygromycin that indicated strong levels of transgene expression. Transformants which showed slow growth rates on liquid TAP with 30 µg mL$^{-1}$ hygromycin were considered to express transgenes at moderate levels. Cells in a liquid culture are exposed to higher doses of antibiotic as compared to plates where local environment is created in a cell's surrounding on a solid medium. Therefore, higher levels of antibiotic expression are required to support growth in a liquid medium as compared to plates. Several strains transformed with the control vector pChlamy_2 showed fast growth on the liquid TAP with 30 µg mL$^{-1}$ of hygromycin.

PCR analysis using gene specific primer sets confirmed the presence of the entire chimeric genes in ten (pCh-HydA, strains petFhydA) and six transformed strains (pCh-HydA-HydG, strains petFhydAG). Two intermediate strains for both pCh-HydA and pCh-HydA-HydG were selected, the petFhydA and the petFhydAG strains, respectively. The petFhydA-15-2 and the petFhydA-17-1 strains showed a strong and a moderate level of PetF-HydA1 fusion protein expression, respectively. The petFhydAG-4-1 and petFhydAG-7-2 strains were selected with relatively high expression levels of PetF-HydA1 and moderate levels of CrGFP-HydG.

TABLE 2

Transformation efficiency of the created vectors in UVM11.

| | No. antibiotic resistant colonies | | | No. PCR positive |
| --- | --- | --- | --- | --- |
| Vector | Agar TAP medium | | Liquid TAP medium/ colonies tested [a] | colonies/No. colonies tested [b] |
| | 10 µm Hg [c] | 30 µm Hg | 30 µm Hg | |
| pChlamy_2 | 304 | 79 | 2/2 | 2/2 |
| pCh-HydA | 500 | 33 | 28/40 | 10/22 |
| pCh-HydA-HydG | 300 | 54 | 27/40 | 6/19 |
| | 10 µm Pr [c] | 30 µm Pr | 10 µm Pr | |
| pJR38 | ~1000 | 250 | 2/2 | 2/2 |
| pJR-HydEF | 350 | 85 | 5/60 | 2/11 |
| | 30 µm Pr/30 µm Hg | 30 µm Pr/30 µm Hg | 30 µm Hg | |
| pCh-HydA + pJR-HydEF | 138 | 71 | 22/56 | 8/32 [d] |
| pCh-HydA-HydG + pJR-HydEF | 154 | 34 | 15/56 | 6/24 [d] |

[a] Number of antibiotic resistant colonies which were tested on liquid TAP.
[b] Number of colonies determined/tested by PCR for the presence of the full-length synthetic cassettes in the genome.
[c] Hg, hygromycin, Pr, paromomycin, µm, µg mL$^{-1}$.
[d] Results of co-transformation experiments.

Expression of the fusion protein was analyzed by a confocal microscope to visualize CrGFP (488 nm excitation/ 490-510 nm filter). Fluorescence was observed in two transgenic strains transformed with pCh-HydA-HydG, petFhydAG-4-1 and petFhydAG-7-2, after 48 h of anaerobic induction of the Cyc6 promoter. These two strains exhibited fast growth on liquid medium. The fluorescent signals were considerably weaker as compared to the strains transformed with the control vector pJR38 containing a gene encoding for CrGFP. This difference in levels of fluorescence was expected because pJR38 carries a CrGFP encoding gene under a strong constitutive PsaD promoter.

Six PCR positive petFhydAG strains were analyzed by Western blotting. The analysis was performed using a living colors monoclonal antibody and anti-mouse IgG-peroxidase secondary antibody with an ECL Advance Western blotting detection kit for chemiluminescence detection. Total protein was extracted using Laemmli buffer. Approximately 5 µg of total protein was loaded per well in 8% SDS-PAGE gels. The expected size bands of 87 kDa were detected for the petFhydAG-4-1 and petFhydAG-7-2 strains while no corresponding bands were observed in protein extracts of other four strains or UVM11. The bands were detected only in cultures which were anaerobically induced. Transgene expression levels in the other strains were below the detection limits. The petFhydAG-4-1 and the petFhydAG-7-2 strains were selected for further analysis.

Two intermediate strains for both pCh-HydA and pCh-HydA-HydG were successfully selected, the petFhydA and the petFhydAG strains, respectively. The petFhydA-15-2 and the petFhydA-17-1 strains showed a strong and a moderate level of PetF-HydA1 fusion protein expression, respectively. The petFhydAG-4-1 and petFhydAG-7-2 strains were selected with relatively high expression levels of PetF-HydA1 and moderate levels of CrGFP-HydG.

Example 6

Intermediate Strains for hydEF Encoding Maturation Proteins

Nuclear transformation of UVM11 with pJR38-HydEF was performed using the glass bead method with pJR38 as a control transformation vector. Numerous antibiotic resistant colonies were obtained on plates with 10 and 30 µg mL$^{-1}$ paromomycin (Table 2). However, only a few colonies could maintain growth on a liquid medium with 10 µg mL$^{-1}$ paromomycin and none with 30 µg mL$^{-1}$ unlike colonies transformed with pJR38. PCR analysis with the specific primer sets developed for pJR-HydEF. (Table 2) showed that the transgenic strains which could grow in a liquid culture with antibiotic carried a recombined chimeric hydEFm gene cassette. The full-length chimeric gene was detected in the transgenic strains which could not grow on liquid medium in the presence of paromomycin. Western blotting using a monoclonal anti-His6-tag primary antibody and same secondary antibody and chemiluminescence detection method as above did not detect the bands of expected size of 53 and 60 kDa in the total protein extracts after anaerobic induction of cultures.

These results point to toxicity of the transgene that is consistent with a radical-generating function of HydE and HydF [81]. Levels of antibiotic expression are linked to levels of hydEFm expression via relations between promoter strengths of these genes. The strength of the Cyc6 promoter can be lowered by a deletion that will fine tune HydE and HydF expression to a desirable level. Two intermediate strains for pJR-HydEF, the hydEF-9-2 and the hydEF-17-2 strains, which contained the full-length transgene sequence and were able to grow on plates with 30 µg mL$^{-1}$ paromomycin, were selected.

Example 7

Combination of Chimeric Genes in Production Strains

The above process produced two strains expressing the PetF-HydA1 fusion protein (petFhydA-17-1 and petFhydA-15-2), two strains with PetF-HydA1 and CrGFP-HydG (petFhydAG-4-1 and petFhydAG-7-2), and two strains expressing the chimeric hydEFm gene encoding HydE and HydF (hydEF-9-2 and hydEF-17-2). The intermediate strains were subjected to mating and co-transformation procedures to combine these genes together. Two production strains were selected, the pr-hydAEF-15-9 strain which derived from the intermediate strains petFhydA-15-2 and hydEF-9-2, and the pr-hydAGEF-7-17 strain, which was obtained using the intermediate strains petFhydAG-7-2 and hydEF-17-2. In addition, a new high throughput protocol for screening transformants by direct measurements of $H_2$ production rates was developed.

Different antibiotic resistance selectable markers in the transformation vectors pChlamy_1 and pJR38 enabled combining all genes to generate productions strains using both mating and co-transformation. Mating was performed as previously described (ref?) using generated intermediate strains to combine all chemeric genes. Co-transformation was performed using the glass bead method to combine pCh-HydA or pCh-HydA-HydG with pJR-HydEF. Transgenic strains were selected on plates supplemented with 10 or 30 µg mL$^{-1}$ of both paromomycin and hygromycin. Numerous colonies were obtained on plates with 30 µg mL$^{-1}$ of both paromomycin and hygromycin by mating for each combination of two strains completing the full set of transgenes. Testing in liquid TAP showed that levels of antibiotic resistance corresponded to that of the parental strains. Results of co-transformation experiments are presented in Table 2. Several strains grew in liquid TAP with 30 µg mL$^{-1}$ hygromycin, but not in the presence of paromomycin as in the case of mating.

The above experiments created numerous colonies. To increase throughput of selecting transformants with increased $H_2$ production, a screening method based on direct measurements of $H_2$ evolution was employed. The method measured $H_2$ release by algae in a liquid medium upon shading. Briefly, cultures were diluted to $2*10^6$ cells/mL, and incubated in a gas-tight bottle for 20 h under a bright light followed by 4 h of shading (80 and 30 µmol photons. s$^{-1}$·m$^{-2}$, respectively $H_2$ concentrations were measured by withdrawing gas samples from the overhead space using a gas-tight syringe and injecting in a Mass Spectrometer.

Results of the testing produced transgenic colonies, the parental, and several intermediate strains are shown in FIG. 3. The intermediate strains transformed with pCh-HydA (petFhydA-17-1 and petFhydA-15-2) and pCh-HydA-HydG (petFhydAG-4-1 and petFhydAG-7-2), but not pJR-HydEF (hydEF-9-2 and hydEF-17-2) showed increases in $H_2$ production up to two-fold as compared to the untransformed UVM11 strain. The later averaged at partial pressure of $4.1*10^{-9}$ Torr. Full-length genes were identified by PCR in the genomic DNA of these strains.

Figure 3A:
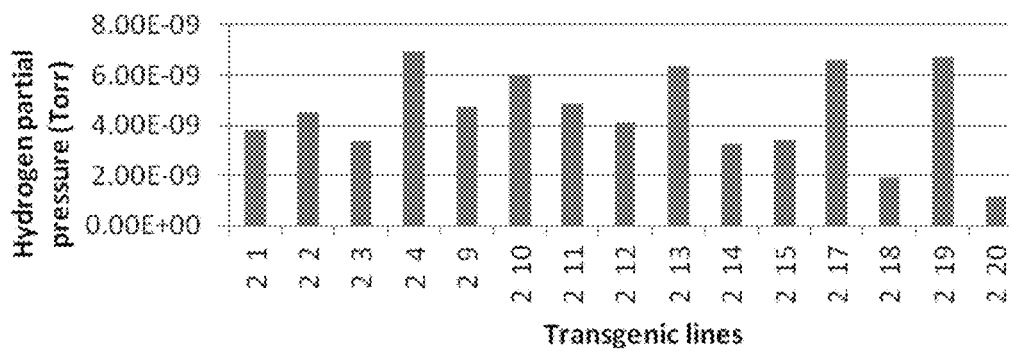
FIG. 3 (a-d) shows screening of transformed strains for colonies with increased $H_2$ production rate, performed using the established screening protocol. $H_2$ concentrations were measured using the Mass Spectrometer. Labeling of transgenic lines: 2 (1-4, 9-15, 17-20)-pCh-HydA; 3 (1, 3, 4, 6-8, 13-17)-pCh-HydA-HydG; 4 (5, 8, 9, 13, 17)-pJR-HydEF; 5 (1, 4-6, 10, 11, 24)-pCh-HydA+pJR-HydEF; 6 (1, 3, 9, 15)-pCh-HydA-HydG+pJR-HydEF.
Figure 3B:
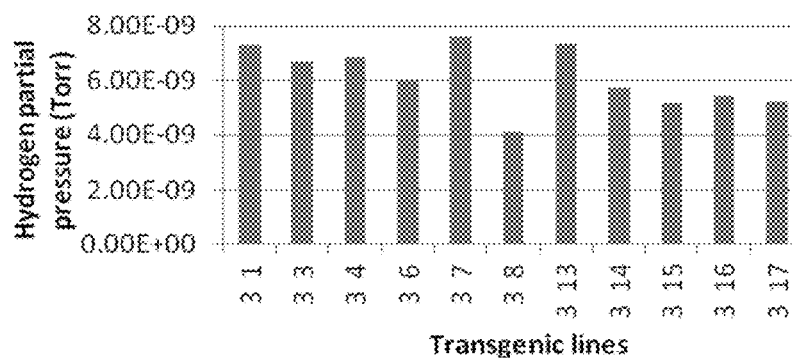
Figure 3C:
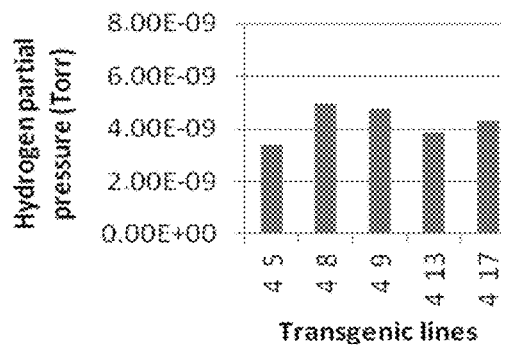
Figure 3D:
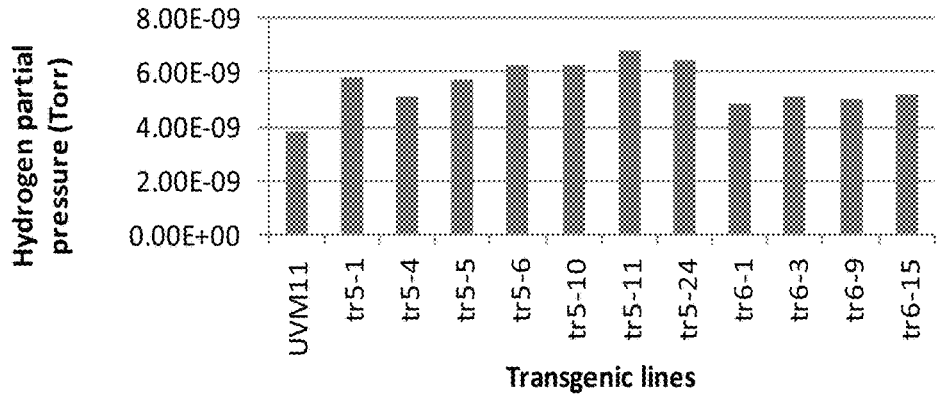

The production strains obtained were named pr-hydAEF lines. When petFhydAG-4-1 or petFhydAG-7-2 was combined with hydEF-9-2 or hydEF-17-2, transgenes were named pr-hydAGEF. Mainly, the production strains obtained by mating showed $H_2$ production rates very similar to that of the parental strains carrying petF-hydA1 with no detectable effect from the hydEF parental strain (FIG. 3c). Thirty seven colonies, which were obtained by co-transformation on plates supplemented with 30 µg $mL^{-1}$ of both paromomycin and hygromycin and grown in liquid TAP with 30 µg $mL^{-1}$ of hygromycin, were screened as well (FIG. 3d). $H_2$ accumulation rates were within the range observed for petFhydA strains.

PCR analysis showed that the full-length transgenes remained intact in the majority of tested colonies produced by mating. PCR analysis of colonies obtained by co-transformation and showing elevated $H_2$ accumulation, confirmed the full-length hydA1m and hydA1m-hydGm gene cassettes, as well as the hydEFm cassette in several strains (Table 3).

The production strains were chosen among colonies obtained by mating. The production strain pr-hydAEF-15-9 was derived from the intermediate strains petFhydA-15-2 and hydEF-9-2. The second production strain pr-hydAGEF-7-17 was selected using the intermediate strains petFhydAhydG-7-2 and hydEF-17-2 as parents.

Figure 4A:
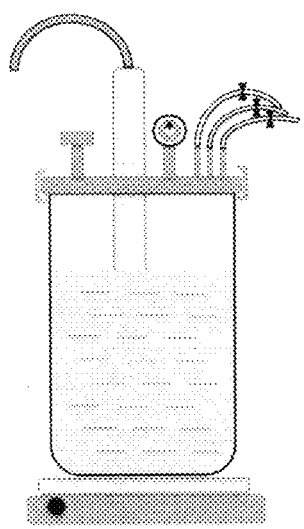
FIG. 4 (A-C) shows the system for analysis of $H_2$, $O_2$ and $CO_2$ concentrations.

A sealed photobioreactor was constructed for bench testing of engineered *Chlamydomonas* strains (FIG. 4A). A spinner 3000 mL vessel contained one large central and two small side ports. The vessel accepted the following accessories: a 3-port tube assembly for purging the head space with $N_2$ and bubbling $CO_2$, liners for gas-tight closure, and a pressure gauge. A custom-made cap for the central port was designed to enable insertion of sensors and gas sampling for analysis under gas-tight setup.

A sonde containing sensors was inserted through the custom-made cap for monitoring algal cultures. A multi-probe sonde housed a temperature, pH, salinity, and dissolved $O_2$ sensors which were positioned at 10 cm below the cell culture surface (Hach Hydromet: Loveland, Colo.). A lighting setup was built for culturing *Chlamydomonas* under cool white fluorescent bulbs. The setup allowed varying of PAR between 12 and 150 µmol photons·$s^{-1}$·$m^{-2}$.

Example 8

In Vitro $H_2$Ase Activity Bioassay

Figure 4B:
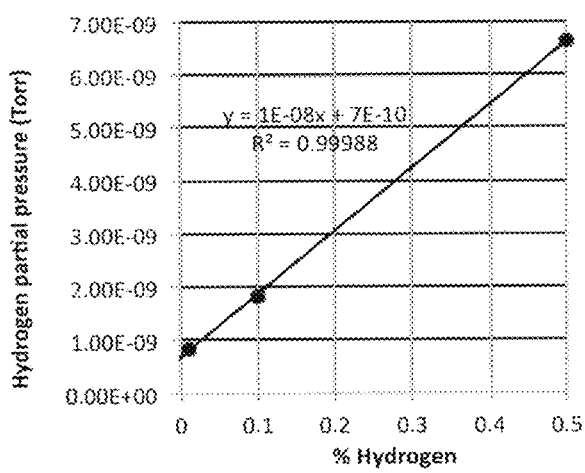
Figure 4C:
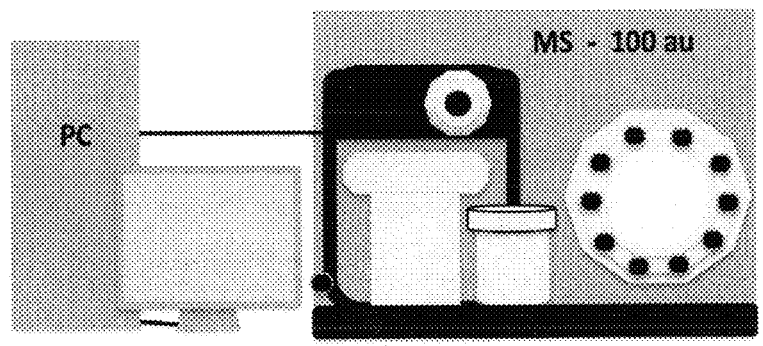

A Dycor Dymaxion Mass Spectrometer was used for continuous, accurate analysis of $H_2$, $O_2$ and $CO_2$ concentrations (FIG. 4B). A gas-tight micro sampling system was created to use the MS for in vitro and in vivo $H_2$ase activity assays. FIG. 4C shows results of the MS calibration which was performed using the pre-manufactured standards of 0.01, 0.1, and 0.5% $H_2$ in $N_2$ (Matheson TriGas, Twinsburg, Ohio). The MS reached a high precision of $H_2$ detection with $R^2$ value of 0.9999. According to the produced standard curve:

% $H_2$=(MS value(Torr)−7*$10^{-10}$)/1*$10^{-8}$ and $H_2$(µmoles/L of culture)=(% $H_2$*overhead space (mL)*1000 (mL)*101.325 (KPa))/8.314 (L*KPA)*310.15 (K)

The above described bioreactor was used to demonstrate increased levels of $H_2$ production. Cultures were grown to the density of 5 to 6*$10^6$ cells/mL in TAP medium at about 22° C., 110 rpm, and 50 µmol photons·$s^{-1}$·$m^{-2}$. Next, cultures were resuspended to the density of 2 to 3*$10^7$ cells/mL in fresh medium that corresponded to nearly 20 µmol chlorophyll/mL of culture. The algal cultures were bubbled with $N_2$ for 2 hr in a dark, and 200 µl aliquots were withdrawn and used in a in vitro $H_2$ase bioassay at 0, 30, 60, 120, and 180 min. The protocol for the in vivo bioassay is described elsewhere [1]. $H_2$ levels were measured using the MS.

This bioassay allows direct measurement of $H_2$ase activity independent of availability of an electron donor in algal cells [86]. An increase of in vitro activity would demonstrate that the synthetic hydA1 gene is functional. A certain increase was anticipated from petFhydA1 overexpression alone, which would normally be limited by availability of wild-type maturation proteins. Transgenic expression of maturation genes would further increase in vitro activity due to more efficient maturation of pre-HydA1.

Several transgenic strains were compared with UVM11 (FIG. 5) using a standard in vitro activity bioassay [94]. Five strains which were transformed displayed an increased in vitro activity of nearly three-fold. The best strain displayed nearly five-fold increase in $H_2$ase activity. The obtained in vitro $H_2$ase activity for the best strain was at 0.118% (v/v) or 100 µM $H_2$ $L^{-1}$ $h^{-1}$ as compared to 0.0193% (v/v) or 19 µM $H_2$ mg $L^{-1}$ $h^{-1}$ for the control. This increase was achieved just by introducing the recombinant HydA1 gene.

Example 9

$H_2$ Production in Engineered *Chlamydomonas* Strains

The in vitro $H_2$ase bioassay above demonstrated that the synthesized hydA1 gene is functional. Because electron donor availability is critical for $H_2$ production by algae, a standard in vivo bioassay under S-deprivation conditions was performed next to test for electron availability under anaerobic condition in the presence of light [87].

Cultures were grown to the density of 5 to 6*$10^6$ cells/mL in TAP medium as described in the above example, washed twice and resuspended in S-free TAP medium to the same cell density and cultured in a gas-tight vessel. The protocol for the in vivo bioassay is described elsewhere [1]. The overhead space of culture bottles was bubbled with $N_2$ during withdrawal of aliquots of cultures for $H_2$ measurements. $H_2$ levels were measured using the MS.

Figure 5A:
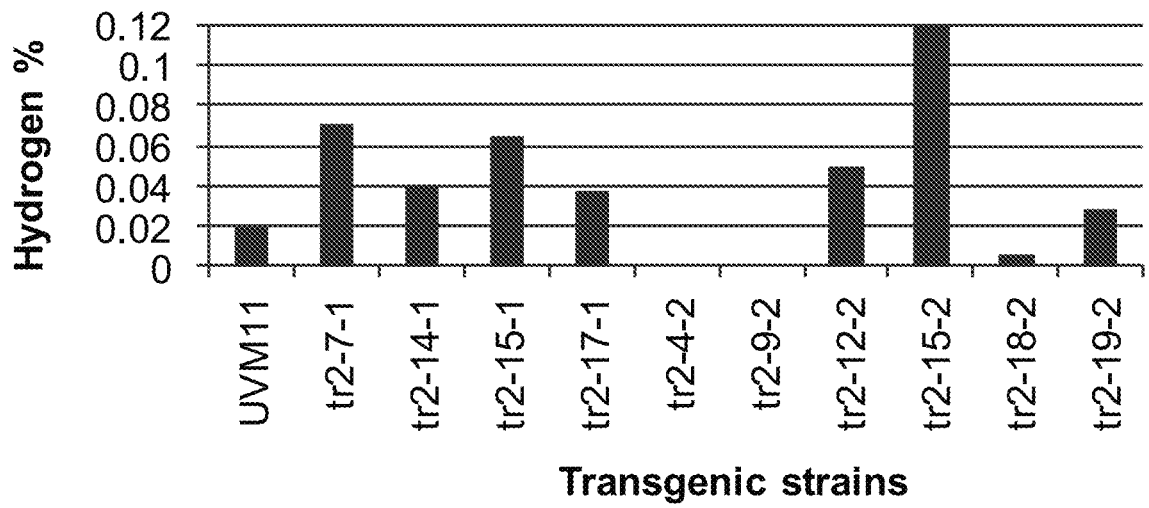
FIG. 5 (a-b) shows in vitro $H_2$ase activity of selected transgenic strains from two independent transformation experiments. Measurements are shown for cultures subjected to anaerobic induction for 180 min. Transgenic strains: tr2, petFhydA; tr3, petFhydAG; tr4, hydEF; tr5, petFhydAEF; tr6, petFhydAGEF. UVM11, untransformed parental strain.
Figure 5B:
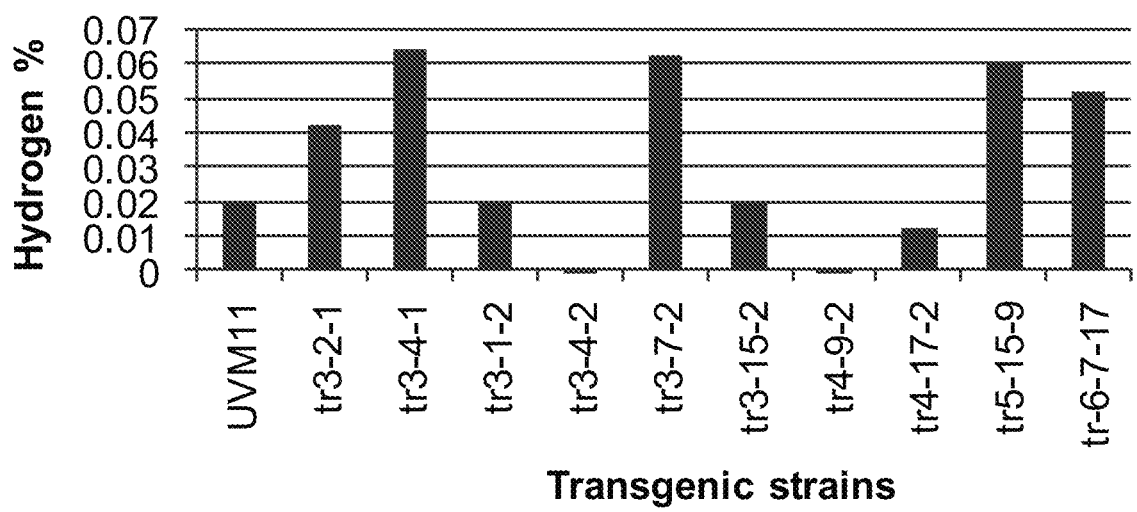
Figure 6A:
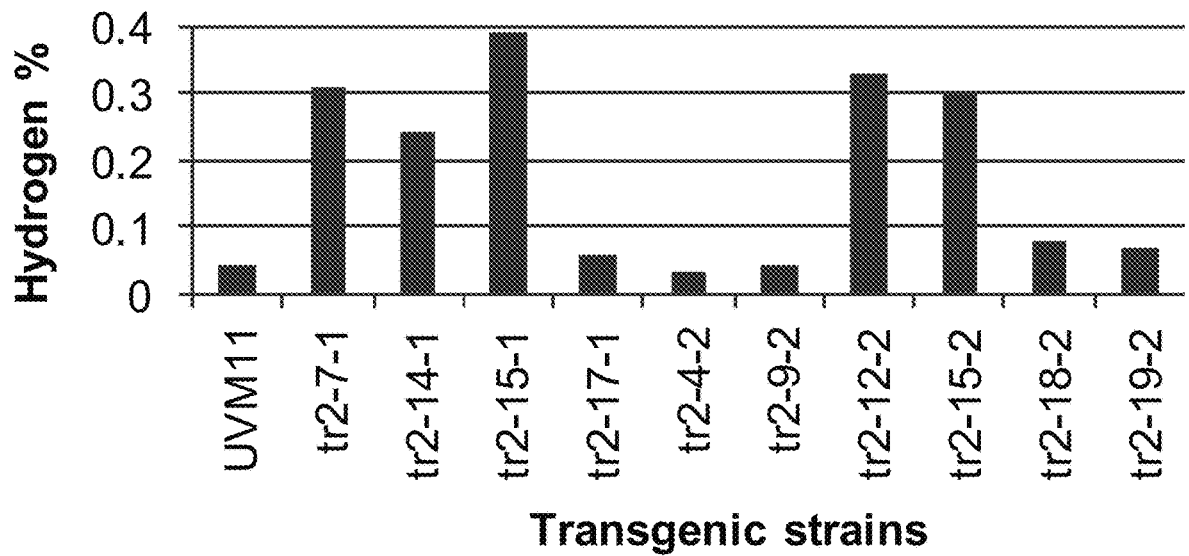
FIG. 6 (a-b) shows in vivo $H_2$ase activity bioassay of selected transformed strains. Transgenic strains labeled the same as in FIG. 5.
Figure 6B:
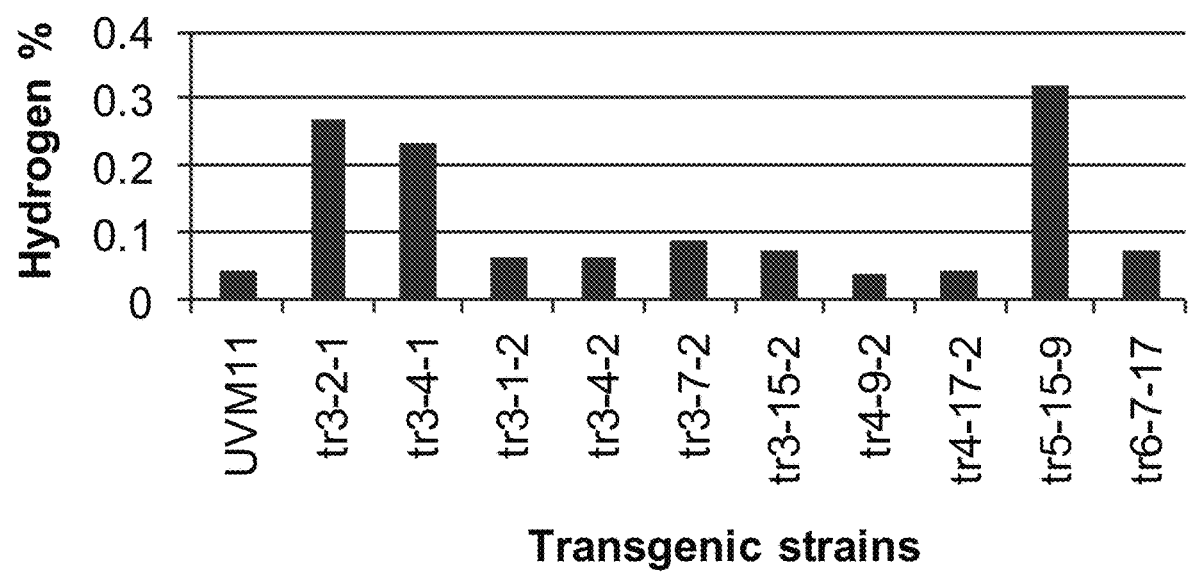

An increase of in vivo $H_2$ase activity was observed in several transgenic strains while the strain petFhydA-15-1 showed the best $H_2$ production rates (FIG. 6b). The best strain as determined by the in vitro bioassay showed nearly ten-fold increase for the in vivo activity (FIG. 5).

Example 10

Sequences

HydA1 (genomic)                                                                                (SEQ ID NO: 1)

TCTTACATGAACACACAAACACTCTCGCAGGCACTAGCCTCAAACCCTCGAAA

CCTTTTTCCAACAGTTTACACCCCAATTCGGACGCCGCTCCAAGCTCGCTCCG

-continued

```
TTGCTCCTTCATCGCACCACCTATTATTTCTAATATCGTAGACGCGACAAGAT

GTCGGCGCTCGTGCTGAAGCCCTGCGCGGCCGTGTCTATTCGCGGCAGCTCCT

GCAGGGCGCGGCAGGTCGCCCCCCGCGCTCCGCTCGCAGCCAGCACCGTGCGT

GTAGCCCTTGCAACACTTGAGGCGCCCGCACGCCGCCTAGGTGAGGGCGACGC

AGTGAACGCAGTTTCGATGGGTCACTTTGTCGCTTTTGCGGAAGCCTCCGAAA

CGTCCCGCGAGGTTCAAACGGCCCGAATGACCACACCCATATGGCCACTGGA

AATAATAACGCAGGCAACGTCGCTTGCGCGGCTGCCGCACCCGCTGCGGAGGC

GCCTTTGAGTCATGTCCAGCAGGCGCTCGCCGAGCTTGGTGAGCGAACGGCCG

AGCGAGCGCGCACGCATTGTTGTGGTCAAGTCTCTCCACTCAGTCCGACCCCC

CACACGGCGTAGGGGTCTGAAGTCCACCAACTCCTCACACACCCCAAGGAAGG

GACGTAAGCCCCCTGGCTACGCTTTACCCAGCAGCCACAGCGACAGAGCGCC

CCAACATAGGCTCGAGATAGAACGCACCTGAACTGTGACACTTACAATGGAAA

GGAACTGCGGATGGCCTTAAAGTCAAGCATTTTGTGACGAGTCGGCTCGGAAT

CCCCATCGGCGCCCGTCCGTTCGTCTTCATCACCGCCTGAAACGGCGCACGCG

CAATAGTGCGCACTTGATGCCTTTCGGTCCAACGCCTCTGTCAGCTAACACTT

TCCAGGGCCAGCGCGGACTCGAGAACCCTCTTTCCTGGCAACCTTGGTTTGGC

TGGCACCTGGCAACCTTGGTTTGGCTGGCACCAACCTTGACCCACATAAATCT

CTCCCCCCCCCCCCTTATGCCCACAGCCAAGCCCAAGGACGACCCCACGCGCAA

GCACGTCTGCGTGCAGGTGGCTCCGGCCGTTCGTGTCGCTATTGCCGAGACCC

TGGGCCTGGCGCCGGGCGCCACCACCCCCAAGCAGCTGGCCGAGGGCCTCCGC

CGCCTCGGCTTTGACGAGGTAGGTGCGCTCGCTGCTGCAGTGCCCAACACGCA

TCTTCCAGCTCACCGCCTACCAGTCAGCACCTTGGCATGCATGCTTGGCGCAT

CTGCCGCCTCATTGCCGCCTCGCGGCCTCGCCGCTGCCTGCATCAAGCCTGCC

GTGCCTGCCTCCCGCCCTCACGCCCAGGTGTTTGACACGCTGTTTGGCGCCGA

CCTGACCATCATGGAGGAGGGCAGCGAGCTGCTGCACCGCCTCACCGAGCACC

ACCCGCACTCCGACGAGCCGCTGCCCATGTTCACCAGCTGCTGCCCCGGCTGG

TGGAGGCCCATCGGTGAGCAGCGCGGCGTGCTTGCTTAGGGCCCCATAACCTG

TCTTGGGCCCCCGCGTCCGCCTCTCCACCTACCTGCAACATGTACGTGCCTA

CGGTATTGTCGCATGTCTCTTGACGATTTGGGTCGACCTTACCTTTGCCTTGT

GTCCTTTCTCCACCCCCACCCGCCTCTTTCCTCGCCGGCCCCCCTCGCGCAGC

TATGCTGGAGAAATCTTACCCGGACCTGATCCCCTACGTGAGCAGCTGCAAGA

GCCCCCAGATGATGCTGGCGGCCATGGTCAAGTCCTACCTAGCGGAAAAGAAG

GGCATCGCGCCAAAGGACATGGTCATGGTGTCCATCATGCCCTGGTGAGAGCC

CCGGGGGGAGGCGGGGATTGCGGGGGGCAGGGGGTGCGGGGGGCAGGGTTTG

CCGGCGTGGTGGAAGGCTGCCCCAGGATGGTCGAGGAGGCCCGCCGTGGGGGT

CTGCCGGCGTAAAATTTGGTATGTGGGTCGAATGGTTCAGCCGCGGAGCCATG

GCGCCGCCCCTGCACCAGCATTCAAGCTGCCTGTGCTGACCCAACCCACCTGC

TTCACCGCCCTGCACACACCGGTGCGCAGCACGCGCAAGCAGTCGGAGGCTGA

CCGCGACTGGTTCTGTGTGGACGCCGACCCCACCCTGCGCCAGCTGGACCACG

TCATCACCACCGTGGAGCTGGGCAACATCTTCAAGGTGGCCGGGGGCGGGG

GGCGGGCGCGCGGGGCGTTATGATTCGGGCCTTAAGGGTTGTTCGCATCATCA
```

-continued

```
TCAGAAAGCCCACCCAGCGCGGAAATGCGAGTCGAACGCGAGTAGGAGTAGTA
GTACTCCTCGCTCTCTGGCACTGCTGTAAGCGCACACGCGCACCCACACGCAC
ACGCACACGCACACGCAACCGCACACGTGCACCAACGTCACATCCACACGCAG
GAGCGCGGCATCAACCTGGCCGAGCTGCCCGAGGGCGAGTGGGACAATCCAAT
GGGCGTGGGCTCGGGCGCCGGCGTGCTGTTCGGCACCACCGGCGGTGTCATGG
AGGCGGCGCTGCGCACGGTGGGTCTGTGAGAGCCGGTTGATTGGCCCGGCAGA
ACGCATACACTTGCTGAACCTTTGATGCGGGATAAGCAAGGCTACCGATCCGC
GTCTTTTTACACCTGTTTATCACGTCGCTGAGCAAGCTCGTGACACCTGCAGG
CCTATGAGCTGTTCACGGGCACGCCGCTGCCGCGCCTGAGCCTGAGCGAGGTG
CGCGGCATGGACGGCATCAAGGAGACCAACATCACCATGGTGCCCGCGCCCGG
GTCCAAGTTTGAGGAGCTGCTGAAGCACCGCGCCGCCGCGCGCGCCGAGGCCG
CCGCGCACGGCACCCCCGGGCCGCTGGCCTGGGACGGCGGCGCGGGCTTCACC
AGCGAGGACGGCAGGGGCGGCATCACACTGCGCGTGGCCGTGGCCAACGGGCT
GGGCAACGCCAAGAAGCTGATCACCAAGATGCAGGCCGGCGAGGCCAAGTACG
ACTTTGTGGAGATCATGGCCTGCCCCGCGGGCTGTGTGGGCGGCGGCGGCCAG
CCCCGCTCCACCGACAAGGCCATCACGCAGAAGCGGCAGGCGGCGCTGTACAA
CCTGGACGAGAAGTGAGCGGGCGGCGCTGCTGGGATTGGGCAGGGGAGGGAAG
GGACTGCGGGCAGGGTGCGGCGGGAAACGGAAATGGGCAAGGCTCGAGGTGG
AGGGCGGGGTGGGTTGGGGTTACTTGCTACAGGTTGGCGGGCAGGATGTGATG
GAAGCAGTGTGGAGGAGGTGTGCGTAGGGTCCCGACGACGGTATTCGCACGAG
CAAAGAGGGTCGGCACTTCCTGACACAATGTGCGCCTGCACGTGCGCTCCTGT
TGCTGCCCCAGGTCCACGCTGCGCCGCAGCCACGAGAACCCGTCCATCCGCGA
GCTGTACGACACGTACCTCGGAGAGCCGCTGGGCCACAAGGTGGGGGGGGGTT
GTAACTACCAGCCCAAATGACGGGGCTGGTCGGGGCGTTGGAGAGGCGGGCC
GGGAGGGAGGCGGGCTGGGTGTGGGGCAACAGCAGGTGAAGGGACGGGGGGGC
ACACTGGGCAGGGCGGTACATGCCTTGTCCTGATAGCTACCCACACGCGACTG
TTGCTACATGGATGCATGACGTGTGCCGTGTGCTTGACCCCTGCAGGCGCACG
AGCTGCTGCACACCCACTACGTGGCCGGCGGCGTGGAGGAGAAGGACGAGAAG
AAGTGAGGAGCGCCAGAGGCTCTTTGGGCGGAGACAGCTTCAAAGCGAGGGGG
CGTATTAGCAGTACCGTAAATATGCACTGATGGGTGATGCGGGTGTCCTCCTT
TATATTGAATGGGGTCAAAATAGGCGGCGGGTCAAATGTTTCCTTTTTGAGTG
GTGTCACAGCATGGGGCACGTGTGCGGAGGCCAGTTGCCCTCCAGTGCACGCG
CTCCCGGTGTGTGGCCGCACTGGCCTTGGATAATGCACCGGTGGAGGATTATG
GAAGAGGGGACTCAGAAGGCTCATTATTGGACAATGCCTGGTCTCTTCCACA
TTGGTGTGAGCGCGGCTCCGCATAGGCTGTTCACTGCACGCTGGCATTAGGCG
TAGGTACTGGCATGAGGGAGCGCGGCTTGCTAACCGAATGGCGTATCCCTCCA
GGGCACGTCGGAATGGCGCGTGCCCATCAACGCAAATTCTTGGCCTTCATCGC
TTCTGGATATTGAAGCTGCACAAACCTGCATTCTATTTGCTTGTTTACACGTG
CCCCAATCTTGGTTGGAAGCTAAACATGTTTGGGAACAATTCATCTTACTAAA
GCGTGTGGGGGTTGAGGATGCGCACGTTGTGCGCTGGTGGGTGGGCGGGAACG
TGGGTAGCATTTAGGCTAGCTGGCATACGACAACGGGGCCCGTGAGGATTGAG
```

-continued
```
CACTTGACTCGCGAACTTATGAACGTAGCGCTTTATACCCACCGTATGCGATT

GACGTTGGTGTAGGCAACCAGGCGGTAGGAAGGCGGAGAGATGCATTGCAAAC

GCCTGTAAAAGAACGGCATAGCTACTAGACACTCTGATGTGGACCCTTGGCGC

AGCCACGACAGGAGAGGTGTGCATCAGCCGCTTGTAAGCACGCACTTCTGAG
```

HydA1 (cDNA)-wild type
(SEQ ID NO: 2)
```
ATGTCGGCGCTCGTGCTGAAGCCCTGCGCGGCCGTGTCTATTCGCGGCAGCTC

CTGCAGGGCGCGGCAGGTCGCCCCCCGCGCTCCGCTCGCAGCCAGCACCGTGC

GTGTAGCCCTTGCAACACTTGAGGCGCCCGCACGCCGCCTAGGCAACGTCGCT

TGCGCGGCTGCCGCACCCGCTGCGGAGGCGCCTTTGAGTCATGTCCAGCAGGC

GCTCGCCGAGCTTGCCAAGCCCAAGGACGACCCCACGCGCAAGCACGTCTGCG

TGCAGGTGGCTCCGGCCGTTCGTGTCGCTATTGCCGAGACCCTGGGCCTGGCG

CCGGGCGCCACCACCCCCAAGCAGCTGGCCGAGGGCCTCCGCCGCCTCGGCTT

TGACGAGGTGTTTGACACGCTGTTTGGCGCCGACCTGACCATCATGGAGGAGG

GCAGCGAGCTGCTGCACCGCCTCACCGAGCACCTGGAGGCCCACCCGCACTCC

GACGAGCCGCTGCCCATGTTCACCAGCTGCTGCCCCGGCTGGATCGCTATGCT

GGAGAAATCTTACCCGGACCTGATCCCCTACGTGAGCAGCTGCAAGAGCCCCC

AGATGATGCTGGCGGCCATGGTCAAGTCCTACCTAGCGGAAAAGAAGGGCATC

GCGCCAAAGGACATGGTCATGGTGTCCATCATGCCCTGCACGCGCAAGCAGTC

GGAGGCTGACCGCGACTGGTTCTGTGTGGACGCCGACCCCACCCTGCGCCAGC

TGGACCACGTCATCACCACCGTGGAGCTGGGCAACATCTTCAAGGAGCGCGGC

ATCAACCTGGCCGAGCTGCCCGAGGGCGAGTGGGACAATCCAATGGGCGTGGG

CTCGGGCGCCGGCGTGCTGTTCGGCACCACCGGCGGTGTCATGGAGGCGGCGC

TGCGCACGGCCTATGAGCTGTTCACGGGCACGCCGCTGCCGCGCCTGAGCCTG

AGCGAGGTGCGCGGCATGGACGGCATCAAGGAGACCAACATCACCATGGTGCC

CGCGCCCGGGTCCAAGTTTGAGGAGCTGCTGAAGCACCGCGCCGCCGCGCGCG

CCGAGGCCGCCGCGCACGGCACCCCCGGGCCGCTGGCCTGGGACGGCGGCGCG

GGCTTCACCAGCGAGGACGGCAGGGGCGGCATCACACTGCGCGTGGCCGTGGC

CAACGGGCTGGGCAACGCCAAGAAGCTGATCACCAAGATGCAGGCCGGCGAGG

CCAAGTACGACTTTGTGGAGATCATGGCCTGCCCCGCGGGCTGTGTGGGCGGC

GGCGGCCAGCCCCGCTCCACCGACAAGGCCATCACGCAGAAGCGGCAGGCGGC

GCTGTACAACCTGGACGAGAAGTCCACGCTGCGCCGCAGCCACGAGAACCCGT

CCATCCGCGAGCTGTACGACACGTACCTCGGAGAGCCGCTGGGCCACAAGGCG

CACGAGCTGCTGCACACCCACTACGTGGCCGGCGGCGTGGAGGAGAAGGACGA

GAAGAAGTGA
```

HydA1 (cDNA)-optimized; removal of selected structures and putative regulatory motifs via silent nucleotide substitutions and codon optimization
(SEQ ID NO: 3)
```
GCTAGCGCCGCTCCTGCTGCTGAGGCTCCTCTGAGCCACGTGCAGCAGGCCCT

GGCTGAGCTGGCCAAGCCCAAGGACGACCCCACCCGCAAGCACGTGTGCGTCC

AGGTCGCCCCTGCTGTGCGCGTGGCCATTGCTGAGACTCTGGGCCTGGCTCCC

GGCGCTACCACCCCTAAGCAGCTGGCTGAGGGCCTGCGCCGCCTGGGCTTTGA

TGAGGTGTTCGACACCCTGTTCGGCGCCGACCTGACCATCATGGAGGAGGGCT
```

-continued

```
CTGAGCTGCTGCACCGCCTGACCGAGCACCTGGAGGCTCACCCTCACAGCGAC
GAGCCCCTGCCCATGTTCACCAGCTGCTGCCCCGGCTGGATCGCCATGCTGGA
GAAGTCCTACCCCGACCTGATCCCCTACGTGTCCAGCTGCAAGAGCCCCCAGA
TGATGCTGGCCGCTATGGTCAAGAGCTACCTGGCCGAGAAGAAGGGCATTGCC
CCCAAGGACATGGTCATGGTGTCCATCATGCCCTGCACGCGCAAGCAGAGCGA
GGCCGACCGCGACTGGTTCTGCGTCGACGCAGACCCTACCCTGCGCCAGCTGG
ACCACGTGATCACCACCGTCGAGCTGGGCAACATCTTCAAGGAGCGCGGCATC
AACCTGGCGGAGCTGCCTGAGGGCGAGTGGGACAACCCTATGGGCGTGGGTTC
TGGCGCTGGCGTGCTGTTCGGCACCACTGGCGGTGTCATGGAGGCCGCCCTGC
GCACCGCTTACGAGCTGTTCACCGGCACCCCTCTGCCCCGCCTGTCTCTGTCT
GAGGTCCGCGGCATGGACGGCATCAAGGAGACTAACATCACGATGGTGCCCGC
TCCCGGCAGCAAGTTCGAGGAGCTCCTGAAGCACCGCGCTGCCGCTCGCGCTG
AGGCTGCTGCTCACGGTACTCCCGGTCCTCTGGCTTGGGACGGCGGTGCTGGC
TTCACTAGCGAGGACGGTCGCGGCGGTATTACCCTGCGCGTGGCAGTGGCTAA
CGGCCTGGGCAACGCCAAGAAGCTGATCACCAAGATGCAGGCCGGCGAGGCGA
AGTACGACTTCGTCGAGATCATGGCCTGCCCCGCTGGCTGCGTCGGTGGTGGT
GGCCAGCCTCGCAGCACCGACAAGGCCATCACCCAGAAGCGCCAGGCCGCGCT
GTACAACCTGGACGAGAAGTCCACCCTGCGCCGCAGCCACGAGAACCCCAGCA
TCCGCGAGCTGTACGACACCTACCTGGGCGAGCCCCTGGGCCACAAGGCTCAC
GAGCTGCTCCACACCCACTACGTGGCAGGCGGCGTCGAGGAGAAGGACGAGAA
GAAGTAG
```

HydA1 (amino acid)
(SEQ ID NO: 4)

```
MSALVLKPCAAVSIRGSSCRARQVAPRAPLAASTVRVALATLEAPARRLGNVA
CAAAAPAAEAPLSHVQQALAELAKPKDDPTRKHVCVQVAPAVRVAIAETLGLA
PGATTPKQLAEGLRRLGFDEVFDTLFGADLTIMEEGSELLHRLTEHLEAHPHS
DEPLPMFTSCCPGWIAMLEKSYPDLIPYVSSCKSPQMMLAAMVKSYLAEKKGI
APKDMVMVSIMPCTRKQSEADRDWFCVDADPTLRQLDHVITTVELGNIFKERG
INLAELPEGEWDNPMGVGSGAGVLFGTTGGVMEAALRTAYELFTGTPLPRLSL
SEVRGMDGIKETNITMVPAPGSKFEELLKHRAAARAEAAAHGTPGPLAWDGGA
GFTSEDGRGGITLRVAVANGLGNAKKLITKMQAGEAKYDFVEIMACPAGCVGG
GGQPRSTDKAITQKRQAALYNLDEKSTLRRSHENPSIRELYDTYLGEPLGHKA
HELLHTHYVAGGVEEKDEKK*
```

Chimeric gene encoding a translational N-terminal fusion of an electron transfer protein PetF to HydA1
(SEQ ID NO: 5)

```
CTCCACCTTCGCCGCCCGCGTTGGCGCTAAGCCCGCTGTACGCGGTGCTCGCC
CCGCCAGCCGCATGAGCTGCATGGCCTACAAGGTCACCCTGAAGACCCCTTCG
GGCGACAAGACCATTGAGTGCCCCGCTGACACCTACATCCTGGACGCTGCTGA
GGAGGCCGGCCTGGACCTGCCCTACTCTTGCCGCGCTGGTGCTTGCTCCAGCT
GCGCCGGCAAGGTCGCTGCCGGCACCGTGGACCAGTCGGACCAGTCCTTCCTG
GACGATGCCCAGATGGGCAACGGCTTCGTGCTGACCTGCGTGGCCTACCCCAC
CTCGGACTGCACCATCCAGACCCACCAGGAGGAGGCCCTGTACACCGGTGGTG
```

```
GTGCATCTTGGAGCCACCCGCAGTTCGAGAAGAGCGGCGGTGGTGCTAGCGCC

GCTCCTGCTGCTGAGGCTCCTCTGAGCCACGTGCAGCAGGCCCTGGCTGAGCT

GGCCAAGCCCAAGGACGACCCCACCCGCAAGCACGTGTGCGTCCAGGTCGCCC

CTGCTGTGCGCGTGGCCATTGCTGAGACTCTGGGCCTGGCTCCCGGCGCTACC

ACCCCTAAGCAGCTGGCTGAGGGCCTGCGCCGCCTGGGCTTTGATGAGGTGTT

CGACACCCTGTTCGGCGCCGACCTGACCATCATGGAGGAGGGCTCTGAGCTGC

TGCACCGCCTGACCGAGCACCTGGAGGCTCACCCTCACAGCGACGAGCCCCTG

CCCATGTTCACCAGCTGCTGCCCCGGCTGGATCGCCATGCTGGAGAAGTCCTA

CCCCGACCTGATCCCCTACGTGTCCAGCTGCAAGAGCCCCCAGATGATGCTGG

CCGCTATGGTCAAGAGCTACCTGGCCGAGAAGAAGGGCATTGCCCCCAAGGAC

ATGGTCATGGTGTCCATCATGCCCTGCACGCGCAAGCAGAGCGAGGCCGACCG

CGACTGGTTCTGCGTCGACGCAGACCCTACCCTGCGCCAGCTGGACCACGTGA

TCACCACCGTCGAGCTGGGCAACATCTTCAAGGAGCGCGGCATCAACCTGGCG

GAGCTGCCTGAGGGCGAGTGGGACAACCCTATGGGCGTGGGTTCTGGCGCTGG

CGTGCTGTTCGGCACCACTGGCGGTGTCATGGAGGCCGCCCTGCGCACCGCTT

ACGAGCTGTTCACCGGCACCCCTCTGCCCCGCCTGTCTCTGTCTGAGGTCCGC

GGCATGGACGGCATCAAGGAGACTAACATCACGATGGTGCCCGCTCCCGGCAG

CAAGTTCGAGGAGCTCCTGAAGCACCGCGCTGCCGCTCGCGCTGAGGCTGCTG

CTCACGGTACTCCCGGTCCTCTGGCTTGGGACGGCGGTGCTGGCTTCACTAGC

GAGGACGGTCGCGGCGGTATTACCCTGCGCGTGGCAGTGGCTAACGGCCTGGG

CAACGCCAAGAAGCTGATCACCAAGATGCAGGCCGGCGAGGCGAAGTACGACT

TCGTCGAGATCATGGCCTGCCCCGCTGGCTGCGTCGGTGGTGGTGGCCAGCCT

CGCAGCACCGACAAGGCCATCACCCAGAAGCGCCAGGCCGCGCTGTACAACCT

GGACGAGAAGTCCACCCTGCGCCGCAGCCACGAGAACCCCAGCATCCGCGAGC

TGTACGACACCTACCTGGGCGAGCCCCTGGGCCACAAGGCTCACGAGCTGCTC

CACACCCACTACGTGGCAGGCGGCGTCGAGGAGAAGGACGAGAAGAAGTAG pX-HydA-gene for constitutive expression of the H₂ase
HydA1 in C. reinhardtii
                                                      (SEQ ID NO: 6)
TCGGGTTTCGCCACCTCTGACTTGAGCGTCGATTTTTGTGATGCTCGTCAGGGG

GGCGGAGCCTATGGAAAAACGCCAGCAACGCGGCCTTTTTACGGTTCCTGGCCT

TTTGCTGGCCTTTTGCTCACATGTTCTTTCCTGCGTTATCCCCTGATTCTGTGG

ATAACCGTATTACCGCCTTTGAGTGAGCTGATACCGCTCGCCGCAGCCGAACGA

CCGAGCGCAGCGAGTCAGTGAGCGAGGAAGCGGTCGCTGAGGCTTGACATGATT

GGTGCGTATGTTTGTATGAAGCTACAGGACTGATTTGGCGGGCTATGAGGGCGG

GGGAAGCTCTGGAAGGGCCGCGATGGGGCGCGCGGCGTCCAGAAGGCGCCATAC

GGCCCGCTGGCGGCACCCATCCGGTATAAAAGCCCGCGACCCCGAACGGTGACC

TCCACTTTCAGCGACAAACGAGCACTTATACATACGCGACTATTCTGCCGCTAT

ACATAACCACTCAGCTAGCTTAAGATCCCATCAAGCTTGCATGCCGGGCGCGCC

AGAAGGAGCGCAGCCAAACCAGGATGATGTTTGATGGGTATTTGAGCACTTGC

AACCCTTATCCGGAAGCCCCCTGGCCCACAAAGGCTAGGCGCCAATGCAAGCAG

TTCGCATGCAGCCCCTGGAGCGGTGCCCTCCTGATAAACCGGCCAGGGGCCTA
```

```
                        -continued
TGTTCTTTACTTTTTTACAAGAGAAGTCACTCAACATCTTAAAATGGCCAGGTG

AGTCGACGAGCAAGCCCGGCGGATCAGGCAGCGTGCTTGCAGATTTGACTTGCA

ACGCCCGCATTGTGTCGACGAAGGCTTTTGGCTCCTCTGTCGCTGTCTCAAGCA

GCATCTAACCCTGCGTCGCCGTTTCCATTTGCAGGAGATTCGAGGTACCATACT

CCACCTTCGCCGCCCGCGTTGGCGCTAAGCCCGCTGTACGCGGTGCTCGCCCCG

CCAGCCGCATGAGCTGCATGGCCTACAAGGTCACCCTGAAGACCCCTTCGGGCG

ACAAGACCATTGAGTGCCCCGCTGACACCTACATCCTGGACGCTGCTGAGGAGG

CCGGCCTGGACCTGCCCTACTCTTGCCGCGCTGGTGCTTGCTCCAGCTGCGCCG

GCAAGGTCGCTGCCGGCACCGTGGACCAGTCGGACCAGTCCTTCCTGGACGATG

CCCAGATGGGCAACGGCTTCGTGCTGACCTGCGTGGCCTACCCCACCTCGGACT

GCACCATCCAGACCCACCAGGAGGAGGCCCTGTACACCGGTGGTGGTGCATCTT

GGAGCCACCCGCAGTTCGAGAAGAGCGGCGGTGGTGCTAGCGCCGCTCCTGCTG

CTGAGGCTCCTCTGAGCCACGTGCAGCAGGCCCTGGCTGAGCTGGCCAAGCCCA

AGGACGACCCCACCCGCAAGCACGTGTGCGTCCAGGTCGCCCCTGCTGTGCGCG

TGGCCATTGCTGAGACTCTGGGCCTGGCTCCCGGCGCTACCACCCCTAAGCAGC

TGGCTGAGGGCCTGCGCCGCCTGGGCTTTGATGAGGTGTTCGACACCCTGTTCG

GCGCCGACCTGACCATCATGGAGGAGGGCTCTGAGCTGCTGCACCGCCTGACCG

AGCACCTGGAGGCTCACCCTCACAGCGACGAGCCCCTGCCCATGTTCACCAGCT

GCTGCCCCGGCTGGATCGCCATGCTGGAGAAGTCCTACCCCGACCTGATCCCCT

ACGTGTCCAGCTGCAAGAGCCCCCAGATGATGCTGGCCGCTATGGTCAAGAGCT

ACCTGGCCGAGAAGAAGGGCATTGCCCCCAAGGACATGGTCATGGTGTCCATCA

TGCCCTGCACGCGCAAGCAGAGCGAGGCCGACCGCGACTGGTTCTGCGTCGACG

CAGACCCTACCCTGCGCCAGCTGGACCACGTGATCACCACCGTCGAGCTGGGCA

ACATCTTCAAGGAGCGCGGCATCAACCTGGCGGAGCTGCCTGAGGGCGAGTGGG

ACAACCCTATGGGCGTGGGTTCTGGCGCTGGCGTGCTGTTCGGCACCACTGGCG

GTGTCATGGAGGCCGCCCTGCGCACCGCTTACGAGCTGTTCACCGGCACCCCTC

TGCCCCGCCTGTCTCTGTCTGAGGTCCGCGGCATGGACGGCATCAAGGAGACTA

ACATCACGATGGTGCCCGCTCCCGGCAGCAAGTTCGAGGAGCTCCTGAAGCACC

GCGCTGCCGCTCGCGCTGAGGCTGCTGCTCACGGTACTCCCGGTCCTCTGGCTT

GGGACGGCGGTGCTGGCTTCACTAGCGAGGACGGTCGCGGCGGTATTACCCTGC

GCGTGGCAGTGGCTAACGGCCTGGGCAACGCCAAGAAGCTGATCACCAAGATGC

AGGCCGGCGAGGCGAAGTACGACTTCGTCGAGATCATGGCCTGCCCCGCTGGCT

GCGTCGGTGGTGGTGGCCAGCCTCGCAGCACCGACAAGGCCATCACCCAGAAGC

GCCAGGCCGCGCTGTACAACCTGGACGAGAAGTCCACCCTGCGCCGCAGCCACG

AGAACCCCAGCATCCGCGAGCTGTACGACACCTACCTGGGCGAGCCCCTGGGCC

ACAAGGCTCACGAGCTGCTCCACACCCACTACGTGGCAGGCGGCGTCGAGGAGA

AGGACGAGAAGAAGTAGGAATTCCCGCTCCGTGTAAATGGAGGCGCTCGTTGAT

CTGAGCCTTGCCCCCTGACGAACGGCGGTGGATGGAAGATACTGCTCTCAAGTG

AGCGGTAGCTTAGCTCCCCGTTTCGTGCTGATCAGTCTTTTTCAACACGTAAAA

CTGAAGCGGAGGAGTTTTGCAATTTTGTTGGTTGTAACGATCCTCCGTTGATTT

TGGCCTCTTTCTCCATTGGCGGGCTGGGCGTATTTGAAGCGAGATCT
```

HydEF (cDNA)-wild type
(SEQ ID NO: 7)

ATGGCGCACAGCCTCAGCGCACACAGCCGTCAGGCTGGTGACAGAAAGCTTGG

CGCGGGCGCGGCCTCGTCGCGCCCGAGCTGTCCCTCGCGCCGCATTGTGCGCG

TCGCCGCGCATGCGAGCGCCTCCAAGGCCACGCCCGACGTCCCGGTCGATGAC

CTGCCTCCCGCTCATGCCCGCGCTGCCGTCGCGGCCGCCAACCGCCGCGCTCG

TGCCATGGCTTCGGCTGAGGCCGCCGCGGAGACCCTGGGTGACTTCCTGGGGC

TCGGCAAGGGCGGGCTTTCGCCCGGGGCCACCGCCAACCTGGACAGGGAACAG

GTACTGGGTGTGCTGGAGGCGGTGTGGCGCCGCGGCGACCTCAACCTGGAGCG

CGCGCTGTACAGCCACGCCAACGCCGTCACCAACAAGTACTGCGGCGGCGGTG

TGTATTACCGCGGCCTGGTGGAGTTCTCCAACATCTGCCAGAACGACTGCAGC

TACTGCGGCATCCGCAACAACCAGAAGGAGGTGTGGCGCTACACCATGCCGGT

GGAGGAGGTGGTGGAGGTGGCCAAGTGGGCGCTGGAGAACGGCATCCGCAACA

TCATGCTGCAGGGCGGCGAGCTCAAAACGGAGCAGCGCCTGGCGTATCTGGAG

GCGTGCGTGCGCGCCATCCGCGAGGAGACCACCCAGCTGGACCTGGAGATGCG

CGCGCGCGCCGCCTCCACCACCACAGCTGAGGCCGCCGCCTCCGCGCAGGCGG

ACGCAGAGGCCAAGAGGGGCGAGCCGGAGCTAGGCGTGGTGGTGTCGCTGAGT

GTGGGCGAGCTGCCCATGGAGCAGTACGAGCGGCTGTTCAGGGCTGGCGCGCG

GCGCTACCTGATCCGCATCGAGACCTCCAACCCCGACCTGTACGCTGCGCTGC

ACCCCGAGCCCATGAGCTGGCACGCGCGCGTGGAGTGCCTGCGCAACCTCAAG

AAGGCCGGCTACATGCTGGGCACTGGCGTGATGGTGGGGCTGCCGGGCCAGAC

GCTGCACGACCTGGCGGGCGACGTCATGTTCTTCCGCGACATCAAGGCCGACA

TGATCGGCATGGGCCCCTTCATCACGCAGCCGGGCACGCCCGCCACCGACAAG

TGGACGCGCTATACCCCAACGCCAACAAGAACAGCCACATGAAGTCCATGTT

CGACCTCACAACCGCCATGAACGCGCTGGTGCGAATCACCATGGGCAACGTCA

ACATCAGCGCCACCACCGCGCTGCAGGCCATCATCCCCACCGGCCGCGAGATT

GCGCTGGAGCGCGGCGCCAATGTGGTGATGCCCATCCTCACGCCCACCCAGTA

CCGCGAGTCCTACCAGCTGTACGAGGGCAAGCCCTGCATCACCGACACCGCCG

TGCAGTGCCGGCGCTGCCTGGACATGCGCCTGCACAGCGTGGGCAAGACCTCC

GCCGCGGGCGTGTGGGGCGACCCCGCCTCCTTCCTGCACCCCATCGTGGGCGT

GCCCGTGCCGCACGACCTGTCCAGCCCCGCGCTGGCCGCCGCCGCCTCCGCCG

ACTTCCACGAGGTGGGAGCCGGCCCCTGGAACCCCATCCGACTGGAGCGATTG

GTGGAGGTGCCGGACCGCTACCCCGACCCCGATAACCATGGCCGCAAGAAGGC

CGGGGCCGGCAAGGGCGGCAAGGCCCACGACTCCCACGACGACGGCGACCACG

ACGACCACCACCACCACCACGGCGCCGCGCCCGCGGGCGCCGCGGCTGGCAAG

GGCACCGGTGCCGCCGCGATCGGTGGCGGCGCCGGCGCTTCGCGCCAGCGCGT

GGCAGGCGCTGCGGCGGCCTCTGCGCGGCTGTGTGCGGGCGCGCGCCGCGCTG

GGCGCGTGGTGGCGTCGCCGCTGCGGCCGGCGGCGGCGTGCCGCGGCGTGGCA

GTGAAGGCGGCGGCGGCGGCGGCTGGCGAGGATGCGGGCGCGGGCACCAGTGG

CGTGGGCAGCAACATTGTGACCAGCCCCGGCATCGCCAGCACCACCGCTCACG

GTGTGCCGCGAATCAACATCGGCGTGTTCGGAGTCATGAATGCGGGCAAGTCG

ACGCTGGTGAACGCTCTGGCGCAGCAGGAGGCGTGCATCGTGGACTCCACGCC

-continued

```
CGGCACCACCGCCGACGTCAAGACGGTGCTTCTAGAGTTGCACGCGCTGGGCC

CGGCCAAGCTGCTGGACACTGCGGGGCTGGACGAGGTGGGCGGGCTGGGCGAC

AAGAAGCGGCGCAAGGCGCTCAACACCCTCAAGGAGTGCGACGTGGCGGTGCT

GGTCGTGGACACGGACACGGCGGCGGCGGCCATCAAGTCCGGCCGCCTGGCGG

AGGCGCTGGAGTGGGAGTCCAAGGTGATGGAGCAGGCGCACAAGTACAACGTC

AGCCCAGTGCTGCTGCTCAACGTCAAGAGCCGGGGGCTACCGGAGGCGCAGGC

AGCGTCCATGCTGGAGGCGGTGGCAGGCATGCTGGACCCAAGCAAGCAGATTC

CCCGCATGTCGCTGGACCTGGCCAGCACGCCGCTGCACGAGCGCTCCACCATC

ACCTCGGCCTTCGTCAAGGAGGGCGCCGTGCGCTCCAGCCGCTACGGCGCGCC

GCTGCCAGGCTGCCTGCCGCGCTGGAGCCTGGGCCGCAACGCCAGGCTGCTCA

TGGTCATCCCCATGGACGCCGAGACCCCCGGCGGCCGCCTGCTGCGCCCACAG

GCGCAGGTCATGGAGGAGGCCATCCGGCACTGGGCCACGGTACTGAGCGTGCG

CCTGGACCTGGACGCGGCGCGCGGCAAGCTAGGACCCGAGGCGTGCGAGATGG

AGCGCCAGCGCTTTGACGGCGTCATCGCAATGATGGAGAGGAACGACGGCCCC

ACGCTGGTGGTCACCGACTCGCAGGCTATCGACGTGGTGCACCCCTGGACTCT

GGACCGCTCCTCCGGGCGGCCGCTGGTGCCCATCACCACCTTCTCCATCGCCA

TGGCCTACCAGCAGAACGGCGGCGGCTGGACCCCTTTGTGGAGGGGCTGGAG

GCGCTAGAGACGCTGCAGGACGGCGACCGCGTGCTGATCTCGGAGGCGTGCAA

CCACAACCGCATCACCTCCGCCTGCAACGACATCGGCATGGTGCAGATCCCCA

ACAAGCTGGAGGCGGCGCTGGGCGGCAAGAAGCTGCAGATCGAGCACGCCTTC

GGCCGCGAGTTCCCGGAGCTTGAGTCGGGCGGTATGGACGGTCTGAAGCTGGC

CATTCACTGCGGCGGCTGCATGATTGACGCCCAGAAGATGCAGCAGCGCATGA

AGGACCTGCACGAGGCAGGCGTGCCCGTCACCAACTACGGCGTGTTCTTCTCT

TGGGCCGCCTGGCCCGACGCCCTGCGCCGCGCGCTGGAGCCCTGGGGTGTCGA

GCCGCCCGTAGGCACTCCCGCCACGCCCGCCGCCGCGCCGGCTACCGCAGCCA

GCGGCGTGTAA
```

HydG (cDNA)-wild type (SEQ ID NO: 8)
```
ATGTCGGTACCTCTGCAGTGCAATGCGGGGCGCCTGCTCGCGGGCCAGCGGCC

CTGCGGCGTCCGCGCCCGGCTGAATCGTCGCGTTTGTGTCCCAGTCACCGCGC

ACGGCAAGGCCTCTGCGACCCGCGAATATGCTGGTGACTTCCTTCCCGGCACT

ACCATTTCACACGCGTGGAGTGTCGAGCGTGAGACGCACCACAGGTACCGCAA

CCCCGCCGAGTGGATCAACGAGGCCGCTATTCACAAGGCGCTGGAGACCTCCA

AGGCGGACGCCCAGGACGCCGGACGGGTGCGCGAGATCCTGGCCAAGGCCAAG

GAAAAGGCCTTCGTCACCGAGCATGCGCCCGTCAACGCCGAGTCCAAGTCCGA

GTTCGTGCAAGGCCTGACGCTGGAGGAGTGCGCTACGCTCATCAACGTGGACT

CGAACAACGTCGAGCTGATGAATGAGATCTTCGACACGGCCCTGGCCATCAAG

GAGCGCATCTACGGGAACCGTGTGGTGCTCTTCGCGCCGCTTTACATCGCCAA

TCACTGCATGAACACCTGCACCTACTGCGCCTTCCGCTCCGCCAACAAGGGCA

TGGAGCGCTCCATCCTCACCGACGACGACCTACGCGAGGAGGTAGCGGCGCTG

CAGCGCCAGGGCCACCGCCGCATCCTGGCGCTCACCGGCGAGCACCCCAAGTA

CACCTTTGACAACTTCCTGCACGCCGTGAACGTGATCGCATCTGTCAAGACGG
```

-continued

```
AGCCGGAGGGCAGCATCCGCCGCATCAATGTGGAGATTCCGCCCCTATCGGTG

TCGGACATGCGCCGCCTGAAGAACACGGACAGCGTGGGCACGTTCGTGCTGTT

CCAGGAGACCTACCACCGCGACACCTTCAAGGTCATGCACCCCTCCGGCCCAA

AGTCCGACTTCGACTTCCGCGTGCTGACGCAGGACCGGGCCATGCGCGCCGGC

CTTGACGACGTGGGCATCGGCGCCCTGTTCGGACTGTACGACTACCGCTACGA

GGTGTGCGCGATGTTGATGCACAGCGAGCACCTGGAGCGCGAGTACAACGCCG

GCCCGCACACCATCAGCGTGCCTCGCATGCGCCCTGCCGACGGCTCCGAGCTG

TCCATTGCGCCGCCGTACCCGGTCAATGACGCTGACTTCATGAAACTGGTGGC

GGTGCTGCGCATCGCGGTGCCGTACACCGGCATGATCCTGTCCACCAGGGAGT

CGCCCGAGATGCGCTCTGCGCTGCTCAAGTGCGGCATGAGCCAGATGAGCGCG

GGCAGCCGCACGGACGTGGGCGCCTACCACAAGGACCACACGCTGTCAACCGA

GGCCAACCTGTCCAAGCTGGCGGGTCAGTTCACGCTGCAGGACGAGCGCCCCA

CCAACGAGATCGTCAAGTGGCTGATGGAGGAGGGCTACGTGCCCAGCTGGTGC

ACGGCCTGCTACCGCCAGGGCCGCACCGGCGAGGACTTCATGAACATCTGCAA

GGCCGGCGACATCCACGACTTCTGCCACCCCAACTCGCTGCTCACGCTCCAGG

AGTACCTGATGGACTACGCCGACCCCGACCTGCGCAAGAAGGGCGAGCAGGTG

ATTGCGCGCGAGATGGGCCCCGACGCCTCGGAGCCGCTGTCGGCGCAGAGCCG

CAAGCGACTGGAGCGCAAGATGAAGCAGGTGCTGGAGGGCGAGCACGACGTGT

ACCTGTAA
```

HydE (cDNA)-optimized; removal of selected structures
and putative regulatory motifs via silent nucleotide
substitutions and codon optimization
(SEQ ID NO: 9)

```
GTCGCTGCTCACGCCAGCGCCAGCAAGGCTACTCCTGATGTGCCCGTGGACGA

CCTGCCTCCTGCTCACGCGCGTGCTGCCGTGGCTGCTGCTAACCGCCGCGCTC

GCGCTATGGCTTCCGCTGAGGCTGCTGCCGAGACTCTGGGCGACTTCCTGGGC

CTGGGCAAGGGTGGCCTGTCTCCCGGCGCTACTGCTAACCTGGACCGCGAGCA

GGTCCTGGGCGTGCTGGAGGCTGTGTGGCGCCGGGGCGACCTGAACCTGGAGC

GCGCTCTGTACAGCCACGCCAACGCCGTGACCAACAAGTATTGCGGCGGTGGC

GTGTACTACCGGGGCCTGGTCGAGTTCAGCAACATCTGCCAGAACGACTGCTC

CTACTGCGGCATCCGCAACAACCAGAAGGAGGTCTGGCGCTACACCATGCCGG

TCGAGGAGGTGGTCGAGGTCGCCAAGTGGGCCCTGGAGAACGGCATCCGGAAC

ATCATGCTCCAGGGCGGCGAGCTCAAGACCGAGCAGCGCCTGGCTTACCTGGA

GGCCTGCGTCCGCGCCATCCGCGAGGAGACTACTCAGCTGGACCTGGAGATGC

GCGCACGCGCTGCTTCGACCACCACTGCTGAGGCCGCTGCTTCCGCCCAGGCC

GACGCTGAGGCTAAGCGCGGCGAGCCTGAGCTGGGTGTCGTGGTGTCTCTGAG

CGTCGGCGAGCTGCCGATGGAGCAGTACGAGCGCCTGTTTCGCGCTGGCGCTC

GCCGCTACCTGATCCGCATCGAGACTAGCAACCCCGACCTGTACGCCGCCCTG

CACCCCGAGCCTATGTCTTGGCATGCTCGCGTCGAGTGCCTGCGCAACCTGAA

GAAGGCCGGCTACATGCTGGGCACCGGCGTGATGGTCGGCCTGCCTGGCCAGA

CTCTGCACGACCTGGCCGGCGACGTGATGTTCTTCCGCGACATCAAGGCCGAC

ATGATCGGCATGGGCCCCTTCATCACCCAGCCCGGCACCCCCGCTACCGACAA

GTGGACCGCTCTGTACCCCAACGCGAACAAGAACAGCCACATGAAGTCCATGT
```

-continued

```
TCGACCTGACCACCGCCATGAACGCCCTCGTGCGCATCACGATGGGCAACGTG

AACATCAGCGCCACCACCGCCCTCCAGGCCATCATTCCCACTGGCCGCGAGAT

CGCTCTGGAGCGCGGTGCCAACGTGGTCATGCCCATCCTGACCCCCACCCAGT

ACCGCGAGAGCTACCAGCTGTACGAGGGCAAGCCCTGCATCACCGACACCGCT

GTGCAGTGCCGCCGCTGCCTGGACATGCGCCTGCACTCTGTGGGCAAGACCAG

CGCCGCGGGCGTGTGGGGCGACCCTGCTTCCTTCCTGCACCCCATTGTGGGCG

TGCCCGTGCCCCACGACCTGAGCAGCCCTGCT
```

HydF (cDNA)-optimized; removal of selected structures and putative regulatory motifs via silent nucleotide substitutions and codon optimization (SEQ ID NO: 10)
```
GTGAAGGCTGCTGCTGCGGCTGCTGGCGAGGACGCAGGCGCTGGTACTTCTGG

CGTGGGCAGCAACATCGTGACCAGCCCCGGCATTGCCAGCACCACTGCTCACG

GCGTGCCCCGCATCAACATCGGCGTGTTCGGCGTGATGAACGCCGGCAAGTCG

ACCCTGGTCAACGCCCTGGCTCAGCAGGAGGCCTGCATCGTCGATAGCACCCC

TGGCACCACCGCCGATGTCAAGACCGTGCTGCTGGAGCTGCACGCCCTGGGCC

CTGCCAAGCTGCTGGACACTGCTGGCCTGGACGAGGTCGGCGGCCTGGGCGAC

AAGAAGCGCCGCAAGGCCCTGAACACCCTGAAGGAGTGCGACGTCGCCGTCCT

GGTGGTGGACACCGACACCGCCGCTGCCGCCATTAAGTCTGGCCGCCTGGCTG

AGGCCCTGGAGTGGGAGAGCAAGGTCATGGAGCAGGCCCACAAGTACAACGTG

TCCCCGGTCCTGCTGCTGAACGTGAAGTCTCGCGGCCTGCCCGAGGCCCAGGC

TGCTTCTATGCTGGAGGCCGTGGCTGGCATGCTGGACCCCAGCAAGCAGATCC

CCCGCATGAGCCTGGACCTGGCCAGCACTCCTCTGCACGAGCGCAGCACCATC

ACCAGCGCCTTCGTGAAGGAGGGCGCTGTCCGCTCTAGCCGCTACGGCGCTCC

TCTGCCTGGTTGCCTGCCTCGCTGGTCCCTGGGTCGCAACGCTCGCCTGCTGA

TGGTCATCCCGATGGACGCCGAGACTCCCGGTGGTCGCCTGCTGCGGCCTCAG

GCTCAGGTCATGGAGGAGGCTATCCGCCACTGGGCCACCGTGCTGTCTGTGCG

GCTGGACCTGGACGCTGCTCGCGGCAAGCTGGGTCCCGAGGCTTGCGAGATGG

AGCGCCAGCGCTTCGACGGCGTGATCGCCATGATGGAGCGCAACGACGGCCCC

ACCCTGGTCGTGACCGACAGCCAGGCCATTGATGTGGTGCACCCCTGGACCCT

GGACCGCTCTTCTGGGCGGCCGCTGGTGCCCATCACCACCTTCTCGATCGCTA

TGGCCTACCAGCAGAACGGCGGTCGCCTGGACCCTTTCGTCGAGGGCCTGGAG

GCGCTGGAGACTCTCCAGGACGGCGACCGCGTGCTGATCAGCGAGGCCTGCAA

CCACAACCGCATCACCTCCGCCTGCAACGACATCGGCATGGTGCAGATCCCCA

ACAAGCTGGAGGCTGCCCTCGGCGGCAAGAAGCTCCAGATCGAGCACGCCTTC

GGCCGCGAGTTCCCTGAGCTGGAGTCTGGCGGCATGGACGGCCTGAAGCTGGC

CATTCACTGCGGCGGCTGCATGATCGACGCCCAGAAGATGCAGCAGCGCATGA

AGGACCTGCACGAGGCCGGCGTGCCCGTGACCAACTACGGCGTGTTCTTCAGC

TGGGCCGCGTGGCCTGATGCTCTGCGCCGCGCTCTGGAGCCTTGGGGTGTCGA

GCCTCCTGTGGGCACCCCTGCTACTCCAGCCGCTGCTCCTGCTACCGCCGCCA

GCGGTGTCTAA
```

-continued

HydG (cDNA)-optimized; removal of selected structures
and putative regulatory motifs via silent nucleotide
substitutions and codon optimization (SEQ ID NO: 11)

ACCGCTCACGGCAAGGCTTCCGCAACTCGCGAGTACGCCGGCGACTTCCTGCC

CGGCACCACCATCTCTCATGCTTGGAGCGTCGAGCGCGAGACTCACCACCGCT

ACCGCAACCCCGCCGAGTGGATCAACGAGGCCGCCATCCACAAGGCCCTGGAG

ACTAGCAAGGCCGACGCTCAGGACGCTGGCCGCGTGCGCGAGATCCTGGCCAA

GGCCAAGGAGAAGGCCTTTGTCACCGAGCACGCCCCCGTGAACGCCGAGAGCA

AGAGCGAGTTCGTGCAGGGCCTGACCCTGGAGGAGTGCGCCACCCTGATCAAC

GTCGACAGCAACAACGTCGAGCTGATGAACGAGATTTTCGACACCGCCCTGGC

CATCAAGGAGCGCATCTACGGCAACCGCGTGGTGCTGTTCGCCCCCCTGTACA

TTGCCAACCACTGCATGAACACGTGCACCTACTGCGCCTTCCGCAGCGCCAAC

AAGGGCATGGAGCGCAGCATCCTGACCGACGACGACCTGCGCGAGGAGGTGGC

AGCTCTCCAGCGCCAGGGTCACCGCCGCATTCTGGCTCTGACCGGCGAGCACC

CCAAGTACACCTTCGACAACTTTCTGCACGCCGTGAACGTGATCGCCTCTGTC

AAGACCGAGCCCGAGGGCAGCATCCGCCGCATCAACGTCGAGATCCCCCCCCT

GTCCGTGTCCGACATGCGCCGCCTGAAGAACACCGACTCCGTGGGCACCTTCG

TGCTGTTTCAGGAGACTTACCACCGGGACACCTTCAAGGTCATGCACCCCAGC

GGCCCCAAGAGCGACTTCGACTTCCGCGTGCTGACCCAGGACCGCGCTATGCG

CGCTGGCCTGGACGACGTGGGCATTGGCGCTCTGTTCGGCCTGTACGACTACC

GCTACGAGGTCTGCGCCATGCTGATGCACAGCGAGCACCTGGAGCGCGAGTAC

AACGCTGGCCCCCACACCATCTCTGTGCCCCGCATGCGCCCTGCTGATGGCAG

CGAGCTGAGCATTGCTCCCCCCTACCCTGTTAACGACGCCGACTTCATGAAGC

TGGTGGCCGTGCTGCGCATTGCCGTGCCCTACACCGGCATGATCCTGAGCACC

CGCGAGAGCCCCGAGATGCGCAGCGCTCTGCTGAAGTGCGGCATGAGCCAGAT

GAGCGCCGGCTCTCGCACCGACGTGGGCGCCTACCACAAGGACCACACCCTGA

GCACCGAGGCCAACCTGAGCAAGCTAGCGGGCCAGTTTACGCTCCAGGACGAG

CGCCCCACCAACGAGATCGTGAAGTGGCTGATGGAGGAGGGTTATGTCCCCAG

CTGGTGCACCGCATGCTACCGCCAGGGTCGCACCGGCGAGGACTTTATGAACA

TCTGCAAGGCCGGCGACATCCACGACTTTTGCCACCCCAACAGCCTGCTGACT

CTCCAGGAGTACCTGATGGACTACGCCGACCCCGACCTGCGCAAGAAGGGCGA

GCAGGTCATCGCTCGCGAGATGGGCCCTGATGCTTCCGAGCCTCTGAGCGCAC

AGAGCCGCAAGCGCCTGGAGCGCAAGATGAAGCAGGTCCTGGAGGGCGAGCAC

GACGTGTACCTGTAG pX-HydG (chimeric gene hydGm)

(SEQ ID NO: 12)

GCAGAGGTTGGGAATCGCTTTGAAAATCCAGCAATCGGGTCTCAGCTGTCTCA

GGCCGCACGCGCCTTGGACAAGGCACTTCAGTAACGTACTCCAAGCCCTCTAT

CTGCATGCCCACAAAGCGCAGGAATGCCGACCATCGTGCCAGACTGTGCCGCG

CCCGAACCGAAATCCGTCACTCCCCTTGGTTCACATGGTGGCATGGTCCCCCC

TGTTCGCCCAAAGCCTGGTTCAGCGCCCAGTGGCAAACGGCTTTGGCTCAGCT

CCTTGGTATTGCTGGTTTCTAGCAATCTCGTCCGTTCCTCTGTTGCCAATGTA

GCAGGTGCAAACAGTCGAATACGGTTTTACTCAGGGGCAATCTCAACTAACAG

-continued
```
AGGCCCTGGGCCTGTTGCCTGGAACCTATGAAGACGATAATGCCACGGCGACT
TTCGAGCCTGAGGGAAGTTTGCACCTGTACCGCATTGTGCAAGGTTACGGTAC
ATGATAGGGGAGTGCGACGCGGTAAGGCTTGGCGCAGCTTGGCGCGTCTGCC
TTGCATGCATGTCCGAAACACGCCACGTCGCGCCACGAAAAGCGGTAAAAGGA
CCTGACATGGTCCTCCAGGGTGTTACCACTTCCATTTCGCTCAGCTGGGATGG
TGCTCGTAGGTGCACCAGCGTTGATTATTTCAGGCAGGAAGCGGCTGCGAAGC
CCGCCTTTCACTGAAGACTGGGATGAGCGCACCTGTACCTGCCAGTATCGTAC
CGGCGCGCTACCGATGCGTGTAGTAGAGCTTGCTGCCATACAGTAACTCTGGT
ACTCCCAGCCACCGGGCGTAGCGAGCAGACTCAATAAGTATGATGGGTTCTTA
TTGCAGCCGCTGTTACAGTTTACAGCGCAAGGGAACACGCCCCTCATTCACAG
AACTAACTCAACCTACTCCATCCATATGCAGGCAAGTAATAGTCCAACCAGTC
TTGCAGCGGCGCTAGGCCGTCTCGCGCTTTCGACCCATCTGACCTTATCGCGT
TTGCCAGCTCCCTCTCGTTCTGGGTGCAGACCGTGCGTGCTCCCGCCGCCT
CCGGCGCCCGCGTGGCTGGCCGCCGCATGTGCCGCCCCGTGGCGGCCCTGCAG
gcACCGGCGGTGGCACCGCTCACGGCAAGGCTTCCGCAACTCGCGAGTACGCC
GGCGACTTCCTGCCCGGCACCACCATCTCTCATGCTTGGAGCGTCGAGCGCGA
GACTCACCACCGCTACCGCAACCCCGCCGAGTGGATCAACGAGGCCGCCATCC
ACAAGGCCCTGGAGACTAGCAAGGCCGACGCTCAGGACGCTGGCCGCGTGCGC
GAGATCCTGGCCAAGGCCAAGGAGAAGGCCTTTGTCACCGAGCACGCCCCCGT
GAACGCCGAGAGCAAGAGCGAGTTCGTGCAGGGCCTGACCCTGGAGGAGTGCG
CCACCCTGATCAACGTCGACAGCAACAACGTCGAGCTGATGAACGAGATTTTC
GACACCGCCCTGGCCATCAAGGAGCGCATCTACGGCAACCGCGTGGTGCTGTT
CGCCCCCCTGTACATTGCCAACCACTGCATGAACACGTGCACCTACTGCGCCT
TCCGCAGCGCCAACAAGGGCATGGAGCGCAGCATCCTGACCGACGACGACCTG
CGCGAGGAGGTGGCAGCTCTCCAGCGCCAGGGTCACCGCCGCATTCTGGCTCT
GACCGGCGAGCACCCCAAGTACACCTTCGACAACTTTCTGCACGCCGTGAACG
TGATCGCCTCTGTCAAGACCGAGCCCGAGGGCAGCATCCGCCGCATCAACGTC
GAGATCCCCCCCCTGTCCGTGTCCGACATGCGCCGCCTGAAGAACACCGACTC
CGTGGGCACCTTCGTGCTGTTTCAGGAGACTTACCACCGGGACACCTTCAAGG
TCATGCACCCCAGCGGCCCCAAGAGCGACTTCGACTTCCGCGTGCTGACCCAG
GACCGCGCTATGCGCGCTGGCCTGGACGACGTGGGCATTGGCGCTCTGTTCGG
GACCCTGTACTACCGCTACGAGGTCTGCGCCATGCTGATGCACAGCGAGCACC
TGGAGCGCGAGTACAACGCTGGCCCCCACACCATCTCTGTGCCCCGCATGCGC
CCTGCTGATGGCAGCGAGCTGAGCATTGCTCCCCCCTACCCTGTTAACGACGC
CGACTTCATGAAGCTGGTGGCCGTGCTGCGCATTGCCGTGCCCTACACCGGCA
TGATCCTGAGCACCCGCGAGAGCCCCGAGATGCGCAGCGCTCTGCTGAAGTGC
GGCATGAGCCAGATGAGCGCCGGCTCTCGCACCGACGTGGGCGCCTACCACAA
GGACCACACCCTGAGCACCGAGGCCAACCTGAGCAAGCTAGCGGGCCAGTTTA
CGCTCCAGGACGAGCGCCCCACCAACGAGATCGTGAAGTGGCTGATGGAGGAG
GGTTATGTCCCCAGCTGGTGCACCGCATGCTACCGCCAGGGTCGCACCGGCGA
GGACTTTATGAACATCTGCAAGGCCGGCGACATCCACGACTTTTGCCACCCCA
```

-continued

ACAGCCTGCTGACTCTCCAGGAGTACCTGATGGACTACGCCGACCCCGACCTG

CGCAAGAAGGGCGAGCAGGTCATCGCTCGCGAGATGGGCCCTGATGCTTCCGA

GCCTCTGAGCGCACAGAGCCGCAAGCGCCTGGAGCGCAAGATGAAGCAGGTCC

TGGAGGGCGAGCACGACGTGTACCTGTAGGAATTCTGGAAGTACGTTGATGTT

GTTATTTCAACTGGGTCACCGTAGCTTGCTCGTGCCCCAGTTGTGGATGCGAG

TTATACGTCATTGCGTAACATGTTCATGATAGACTGCATTAGGTAGGCGTCGT

GTGTGAGCACATACAGAAGTCATCACGCAAATGGACACGTTCCGGCGAACCCG

AGGGGAAAGGCTTGGGCCAGTACATTATTTCAACACTAAAATATGTAACATAA

TGGAACTTGAGCACGGTCCGGGAGCGCAGGCTGGGCTTGGGGGTCGCGGCTCG

AAGGAGAGGGGCGACGTTGGGGCAGGTCGGGGCTTCAACCGGGTT pX-HydEF (chimeric gene hydEFm)

(SEQ ID NO: 13)

ACTAGAGCAGAGGTTGGGAATCGCTTTGAAAATCCAGCAATCGGGTCTCAGCT

GTCTCAGGCCGCACGCGCCTTGGACAAGGCACTTCAGTAACGTACTCCAAGCC

CTCTATCTGCATGCCCACAAAGCGCAGGAATGCCGACCATCGTGCCAGACTGT

GCCGCGCCCGAACCGAAATCCGTCACTCCCCTTGGTTCACATGGTGGCATGGT

CCCCCCTGTTCGCCCAAAGCCTGGTTCAGCGCCCAGTGGCAAACGGCTTTGGC

TCAGCTCCTTGGTATTGCTGGTTTCTAGCAATCTCGTCCGTTCCTCTGTTGCC

AATGTAGCAGGTGCAAACAGTCGAATACGGTTTTACTCAGGGGCAATCTCAAC

TAACAGAGGCCCTGGGCCTGTTGCCTGGAACCTATGAAGACGATAATGCCACG

GCGACTTTCGAGCCTGAGGGAAGTTTGCACCTGTACCGCATTGTGCAAGGTTA

CGGTACATGATAGGGGAGTGCGACGCGGTAAGGCTTGGCGCAGCTTGGCGCG

TCTGCCTTGCATGCATGTCCGAAACACGCCACGTCGCGCCACGAAAAGCGGTA

AAAGGACCTGACATGGTCCTCCAGGGTGTTACCACTTCCATTTCGCTCAGCTG

GGATGGTGCTCGTAGGTGCACCAGCGTTGATTATTTCAGGCAGGAAGCGGCTG

CGAAGCCCGCCTTTCACTGAAGACTGGGATGAGCGCACCTGTACCTGCCAGTA

TCGTACCGGCGCGCTACCGATGCGTGTAGTAGAGCTTGCTGCCATACAGTAAC

TCTGGTACTCCCAGCCACCGGGCGTAGCGAGCAGACTCAATAAGTATGATGGG

TTCTTATTGCAGCCGCTGTTACAGTTTACAGCGCAAGGGAACACGCCCCTCAT

TCACAGAACTAACTCAACCTACTCCATCCATATGCAGGCAAGTAATAGTCCAA

CCAGTCTTGCAGCGGCGCTAGGCCGTCTCGCGCTTTCGACCCATCTGACCTTA

TCGCGTGCTCCCTCTCTCGTTCTGGGTGCAGACCGTGCGTGCTCCCGCCGCCT

CCGGCGTTGCCACCCGCGTGGCTGGCCGCCGCATGTGCCGCCCCGTGGCGGCC

CTGCAGGGTGGTACTCACCACCACCACCACCACGGCTCTGGCGGCGGTTCTGG

TGGTGGTTCTGGCGGTGTCGCTGCTCACGCCAGCGCCAGCAAGGCTACTCCTG

ATGTGCCCGTGGACGACCTGCCTCCTGCTCACGCGCGTGCTGCCGTGGCTGCT

GCTAACCGCCGCGCTCGCGCTATGGCTTCCGCTGAGGCTGCTGCCGAGACTCT

GGGCGACTTCCTGGGCCTGGGCAAGGGTGGCCTGTCTCCCGGCGCTACTGCTA

ACCTGGACCGCGAGCAGGTCCTGGGCGTGCTGGAGGCTGTGTGGCGCCGGGGC

GACCTGAACCTGGAGCGCGCTCTGTACAGCCACGCCAACGCCGTGACCAACAA

GTATTGCGGCGGTGGCGTGTACTACCGGGGCCTGGTCGAGTTCAGCAACATCT

GCCAGAACGACTGCTCCTACTGCGGCATCCGCAACAACCAGAAGGAGGTCTGG

-continued
```
CGCTACACCATGCCGGTCGAGGAGGTGGTCGAGGTCGCCAAGTGGGCCCTGGA
GAACGGCATCCGGAACATCATGCTCCAGGGCGGCGAGCTCAAGACCGAGCAGC
GCCTGGCTTACCTGGAGGCCTGCGTCCGCGCCATCCGCGAGGAGACTACTCAG
CTGGACCTGGAGATGCGCGCACGCGCTGCTTCGACCACCACTGCTGAGGCCGC
TGCTTCCGCCCAGGCCGACGCTGAGGCTAAGCGCGGCGAGCCTGAGCTGGGTG
TCGTGGTGTCTCTGAGCGTCGGCGAGCTGCCGATGGAGCAGTACGAGCGCCTG
TTTCGCGCTGGCGCTCGCCGCTACCTGATCCGCATCGAGACTAGCAACCCCGA
CCTGTACGCCGCCCTGCACCCCGAGCCTATGTCTTGGCATGCTCGCGTCGAGT
GCCTGCGCAACCTGAAGAAGGCCGGCTACATGCTGGGCACCGGCGTGATGGTC
GGCCTGCCTGGCCAGACTCTGCACGACCTGGCCGGCGACGTGATGTTCTTCCG
CGACATCAAGGCCGACATGATCGGCATGGGCCCCTTCATCACCCAGCCCGGCA
CCCCCGCTACCGACAAGTGGACCGCTCTGTACCCCAACGCGAACAAGAACAGC
CACATGAAGTCCATGTTCGACCTGACCACCGCCATGAACGCCCTCGTGCGCAT
CACGATGGGCAACGTGAACATCAGCGCCACCACCGCCCTCCAGGCCATCATTC
CCACTGGCCGCGAGATCGCTCTGGAGCGCGGTGCCAACGTGGTCATGCCCATC
CTGACCCCCACCCAGTACCGCGAGAGCTACCAGCTGTACGAGGGCAAGCCCTG
CATCACCGACACCGCTGTGCAGTGCCGCCGCTGCCTGGACATGCGCCTGCACT
CTGTGGGCAAGACCAGCGCCGCGGGCGTGTGGGGCGACCCTGCTTCCTTCCTG
CACCCCATTGTGGGCGTGCCCGTGCCCCACGACCTGAGCAGCCCTGCTCTCGC
TGCTGCTGCCAGCGCCGACTTTCACGAGGTCGGCGCTGGTCCCTGGAACCCCA
TTCGCCTGGAGCGGCTGGTCGAGGTGCCCGACCGCTACCCTGACCCTGACAAC
CATGGCCGCAAGAAGGCTGGCGCTGGCAAGGGCGGCAAGGCCCACGACTCTCA
CGACGACGGCGACCACGACGACCACCACCACCACGGTGCTGCTCCCGCTG
GTGCTGCTGCCGGCAAGGGTACTGGCGCTGCTGCTATTGGCGGCGGTGCTGGT
GCTTCTCGCCAGCGCGTGGCAGGCGCAGCTGCTGCTTCTGCTCGCCTGTGCGC
TGGTGCTCGCCGCGCTGGTCGCGTGGTGGCTTCTCCTCTGCGCCCTGCTGCTG
CTTGCCAGGGCGTGGCCGTGAAGGCTGCTGCTGCGGCTGCTGGCGAGGACGCA
GGCGCTGGTACTTCTGGCGTGGGCAGCAACATCGTGACCAGCCCCGGCATTGC
CAGCACCACTGCTCACGGCGTGCCCCGCATCAACATCGGCGTGTTCGGCGTGA
TGAACGCCGGCAAGTCGACCCTGGTCAACGCCCTGGCTCAGCAGGAGGCCTGC
ATCGTCGATAGCACCCCTGGCACCACCGCCGATGTCAAGACCGTGCTGCTGGA
GCTGCACGCCCTGGGCCCTGCCAAGCTGCTGGACACTGCTGGCCTGGACGAGG
TCGGCGGCCTGGGCGACAAGAAGCGCCGCAAGGCCCTGAACACCCTGAAGGAG
TGCGACGTCGCCGTCCTGGTGGTGGACACCGACACCGCCGCTGCCGCCATTAA
GTCTGGCCGCCTGGCTGAGGCCCTGGAGTGGGAGAGCAAGGTCATGGAGCAGG
CCCACAAGTACAACGTGTCCCCGGTCCTGCTGCTGAACGTGAAGTCTCGCGGC
CTGCCCGAGGCCCAGGCTGCTTCTATGCTGGAGGCCGTGGCTGGCATGCTGGA
CCCCAGCAAGCAGATCCCCGCATGAGCCTGGACCTGGCCAGCACTCCTCTGC
ACGAGCGCAGCACCATCACCAGCGCCTTCGTGAAGGAGGGCGCTGTCCGCTCT
AGCCGCTACGGCGCTCCTCTGCCTGGTTGCCTGCCTCGCTGGTCCCTGGGTCG
CAACGCTCGCCTGCTGATGGTCATCCCGATGGACGCCGAGACTCCCGGTGGTC
```

-continued

```
GCCTGCTGCGGCCTCAGGCTCAGGTCATGGAGGAGGCTATCCGCCACTGGGCC

ACCGTGCTGTCTGTGCGGCTGGACCTGGACGCTGCTCGCGGCAAGCTGGGTCC

CGAGGCTTGCGAGATGGAGCGCCAGCGCTTCGACGGCGTGATCGCCATGATGG

AGCGCAACGACGGCCCCACCCTGGTCGTGACCGACAGCCAGGCCATTGATGTG

GTGCACCCCTGGACCCTGGACCGCTCTTCTGGGCGGCCGCTGGTGCCCATCAC

CACCTTCTCGATCGCTATGGCCTACCAGCAGAACGGCGGTCGCCTGGACCCTT

TCGTCGAGGGCCTGGAGGCGCTGGAGACTCTCCAGGACGGCGACCGCGTGCTG

ATCAGCGAGGCCTGCAACCACAACCGCATCACCTCCGCCTGCAACGACATCGG

CATGGTGCAGATCCCCAACAAGCTGGAGGCTGCCCTCGGCGGCAAGAAGCTCC

AGATCGAGCACGCCTTCGGCCGCGAGTTCCCTGAGCTGGAGTCTGGCGGCATG

GACGGCCTGAAGCTGGCCATTCACTGCGGCGGCTGCATGATCGACGCCCAGAA

GATGCAGCAGCGCATGAAGGACCTGCACGAGGCCGGCGTGCCCGTGACCAACT

ACGGCGTGTTCTTCAGCTGGGCCGCGTGGCCTGATGCTCTGCGCCGCGCTCTG

GAGCCTTGGGGTGTCGAGCCTCCTGTGGGCACCCCTGCTACTCCAGCCGCTGC

TCCTGCTACCGCCGCCAGCGGTGTCTAAGAATTCTGGAAGTACGTTGATGTTG

TTATTTCAACTGGGTCACCGTAGCTTGCTCGTGCCCCAGTTGTGGATGCGAGT

TATACGTCATTGCGTAACATGTTCATGATAGACTGCATTAGGTAGGCGTCGTG

TGTGAGCACATACAGAAGTCATCACGCAAATGGACACGTTCCGGCGAACCCGA

GGGGAAAGGCTTGGGCCAGTACATTATTTCAACACTAAAATATGTAACATAAT

GGAACTTGAGCACGGTCCGGGAGCGCAGGCTGGGCTTGGGGGTCGCGGCTCGA

AGGAGAGGGGCGACGTTGGGGCAGGTCGGGCTTCAACCGGGTTTCACTAGA
```

HydE (amino acid) optimized
(SEQ ID NO: 14)
```
VAAHAS AS KATPDVPVDDLPPAHARAAVAAANRRARAMASAEAAAETLGDFL

GLGKGGLSPGATANLDREQVLGVLEAVWRRGDLNLERALYSHANAVTNKYCGGG

VYYRGLVEFSNICQNDCSYCGIRNNQKEVWRYTMPVEEVVEVAKWALENGIRNI

MLQGGELKTEQRLAYLEACVRAIREETTQLDLEMRARAASTTTAEAAASAQADA

EAKRGEPELGVVVSLSVGELPMEQYERLFRAGARRYLIRIETSNPDLYAALHPE

PMSWHARVECLRNLKKAGYMLGTGVMVGLPGQTLHDLAGDVMFFRDIKADMIGM

GPFITQPGTPATDKWTALYPNANKNSHMKSMFDLTTAMNALVRITMGNVNISAT

TALQAIIPTGREIALERGANVVMPILTPTQYRESYQLYEGKPCITDTAVQCRRC

LDMRLHSVGKTSAAGVWGDPASFLHPIVGVPVPHDLSSPA
```

HydF (amino acid) optimized
(SEQ ID NO: 15)
```
VKAAAAAAGEDAGAGTSGVGSNIVTSPGIASTTAHGVPRINIGVFGVMNAGKST

LVNALAQQEACIVDSTPGTTADVKTVLLELHALGPAKLLDTAGLDEVGGLGDKK

RRKALNTLKECDVAVLVVDTDTAAAAIKSGRLAEALEWESKVMEQAHKYNVSPV

LLLNVKSRGLPEAQAASMLEAVAGMLDPSKQIPRMSLDLASTPLHERSTITSAF

VKEGAVRSSRYGAPLPGCLPRWSLGRNARLLMVIPMDAETPGGRLLRPQAQVME

EAIRHWATVLSVRLDLDAARGKLGPEACEMERQRFDGVIAMMERNDGPTLVVTD

SQAIDVVHPWTLDRSSGRPLVPITTFSIAMAYQQNGGRLDPFVEGLEALETLQD

GDRVLISEACNHNRITSACNDIGMVQIPNKLEAALGGKKLQIEHAFGREFPELE
```

-continued

```
SGGMDGLKLAIHCGGCMIDAQKMQQRMKDLHEAGVPVTNYGVFFSWAAWPDALR

RALEPWGVEPPVGTPATPAAAPATAASGV
```

HydG (amino acid) optimized (SEQ ID NO: 16)
```
TAHGKASATREYAGDFLPGTTISHAWSVERETHHRYRNPAEWINEAAIHKALETS

KADAQDAGRVREILAKAKEKAFVTEHAPVNAESKSEFVQGLTLEECATLINVDSN

NVELMNEIFDTALAIKERIYGNRVVLFAPLYIANHCMNTCTYCAFRSANKGMERS

ILTDDDLREEVAALQRQGHRRILALTGEHPKYTFDNFLHAVNVIASVKTEPEGSI

RRINVEIPPLSVSDMRRLKNTDSVGTFVLFQETYHRDTFKVMHPSGPKSDFDFRV

LTQDRAMRAGLDDVGIGALFGLYDYRYEVCAMLMHSEHLEREYNAGPHTISVPRM

RPADGSELSIAPPYPVNDADFMKLVAVLRIAVPYTGMILSTRESPEMRSALLKCG

MSQMSAGSRTDVGAYHKDHTLSTEANLSKLAGQFTLQDERPTNEIVKWLMEEGYV

PSWCTACYRQGRTGEDFMNICKAGDIHDFCHPNSLLTLQEYLMDYADPDLRKKGE

QVIAREMGPDASEPLSAQSRKRLERKMKQVLEGEHDVYL
```

REFERENCES

[1] U.S.D.o. Energy, Roadmap on Manufacturing R&D for the Hydrogen Economy http://www.hydrogen.energy.gov/pdfs/roadmap_manufacturing_hydrogen_economy.pdf, vol. p. ES-1 2007.

[2] U.S. Department of Energy, "President's Hydrogen Fuel Initiative: A Secure Energy Future".

[3] The Energy Information Administration (2008) The Impact of Increased Use of Hydrogen on Petroleum Consumption and Carbon Dioxide Emissions.

[4] J. Meyer, J. Gagnon, Primary structure of hydrogenase I from Clostridium pasteurianum, Biochemistry 30 (1991) 9697-9704.

[5] G. Kubas, Fundamentals of $H_2$ binding and reactivity on transition metals underlying hydrogenase function and $H_2$ production and storage, Chem. Rev. 107 (2007) 4152-4205.

[6] G. Bromaghim, K. Gibeault, J. Serfass, P. Serfass, E. Wagner, Hydrogen and Fuel Cells: The U.S. Market Report, The National Hydrogen Association, http://www.hydrogenassociation.org/marketreport, 2010.

[7] Hydrogen as a Chemical Constituent and as an Energy Source 2011, p. 207.

[8] T. Lipman, An overview of hydrogen production and storage systems with renewable hydrogen case study, vol. cleanenergystates.org, Clean Energy States Alliance, 2010.

[9] S. Fouchard, J. Pruvost, B. Degrenne, M. Titica, J. Legrand, Kinetic modeling of light limitation and sulfur deprivation effects in the induction of hydrogen production with Chlamydomonas reinhardtii: Part I. Model development and parameter identification, Biotechnol. Bioeng. 102 (2008) 232-245.

[10] W. Park, I. Moon, A discrete multi states model for the biological production of hydrogen by phototrophic microalga, Biochem. Eng. J. 36 (2007) 19-27.

[11] M. Frey, Hydrogenases: hydrogen-activating enzymes, Chembiochem 3 (2002) 153-160.

[12] A. Melis, Photosynthetic $H_2$ metabolism in Chlamydomonas reinhardtii (unicellular green algae). Planta 226 (2007) 1075-1086.

[13] S. Kosourov, M. Seibert, Hydrogen photoproduction by nutrient-deprived Chlamydomonas reinhardtii cells immobilized within thin alginate films under aerobic and anaerobic conditions, Biotechnol. Bioeng. 102. (2008) 50-58.

[14] Y.-K. Oh, S. M. Raj, G. Y. Jung, S. Park, Current status of the metabolic engineering of microorganisms for biohydrogen production, Bioresour. Technol. 102 (2011) 8357-8367.

[15] K. Vincent, A. Parkin, O. Lenz, S. Albracht, J. Fontecilla-Camps, R. Cammack, B. Friedrich, F. Armstrong, Electrochemical definitions of $O_2$ sensitivity and oxidative inactivation in hydrogenases, Journal of American Chemical Society 127 (2005) 18179-18189.

[16] M. Ghirardi, R. Togasaki, M. Seibert, Oxygen sensitivity of algal $H_2$-production, Appl. Biochem. Biotechnol. 63-65 (1997) 141-151.

[17] A. Melis, L. Zhang, M. Forestier, M. Ghirardi, M. Seibert, Sustained photobiological hydrogen gas production upon reversible inactivation of oxygen evolution in the green alga Chlamydomonas reinhardtii, Plant Physiology 122 (2000) 127-136.

[18] R. Burch, Gold catalysts for pure hydrogen production in the water-gas shift reaction: activity, structure and reaction mechanism, PCCP 8 (2006) 5483-5500.

[19] T. Meyer, Catalysis: the art of splitting water, Nature 451 (2008) 778-779.

[20] M. Ghirardi, M. Posewitz, P. Maness, A. Dubini, J. Yu, M. Seibert, Hydrogenases and hydrogen photoproduction in oxygenic photosynthetic organisms, Annual Review of Plant Biology 58 (2007) 71-91.

[21] J. Rosenberg, G. Oyler, L. Wilkinson, M. Betenbaugh, A green light for engineered algae: redirecting metabolism to fuel a biotechnology revolution, Curr. Opin. Biotechnol. (2008) Epub ahead of print.

[22] R. León-Bañares, D. González-Ballester, A. Galván, E. Fernandez, Transgenic microalgae as green cell-factories, Trends Biotechnol 22 (2004) 45-52.

[23] K. Shimogawara, S. Fujiwara, A. Grossman, H. Usuda, High-efficiency transformation of Chlamydomonas reinhardtii by electroporation, Genetics 148 (1998) 1821-1828.

[24] J. Neupert, D. Karcher, R. Bock, Generation of *Chlamydomonas* strains that efficiently express nuclear transgenes, Plant Journal 57 (2009) 1140-1150.

[25] K. L. Kindle, High-frequency nuclear transformation of *Chlamydomonas reinhardtii*, Proc Natl Acad Sci USA 87 (1990) 1228-1232.

[26] Y. Nicolet, B. Lemon, J. Fontecilla-Camps, J. Peters, A novel FeS cluster in Fe-only hydrogenases, Trends Biochem Sci 25 (2000) 138-143.

[27] Y. Nicolet, A. de Lacey, X. Vernède, V. Fernandez, E. Hatchikian, J. Fontecilla-Camps, Crystallographic and FTIR spectroscopic evidence of changes in Fe coordination upon reduction of the active site of the Fe-only hydrogenase from Desulfovibrio desulfuricans, J Am Chem Soc 123 (2001) 1596-1601.

[28] J. Peters, W. Lanzilotta, B. Lemon, L. Seefeldt, X-ray crystal structure of the Fe-only hydrogenase (CpI) from *Clostridium* pasteurianum to 1.8 angstrom resolution, Science 282 (1998) 1853-1858.

[29] P. King, M. Posewitz, M. Ghirardi, S. M, Functional studies of [FeFe] hydrogenase maturation in an *Escherichia coli* biosynthetic system, J Bacteriol 188 (2006) 2163-2172.

[30] R. Lill, Function and biogenesis of iron-sulfur proteins, Nature 460 (2009) 831-838.

[31] E. Pilet, Y. Nicolet, C. Mathevon, T. Douki, J. Fontecilla-Camps, M. Fontecave, The role of the maturase HydG in [FeFe]-hydrogenase active site synthesis and assembly, FEBS Lett. 583 (2009) 506-511.

[32] D. Mulder, D. Ortillo, D. Gardenghi, A. Naumov, S. Ruebush, R. Szilagyi, B. Huynh, J. Broderick, J. Peters, Activation of HydA(DeltaEFG) requires a preformed [4Fe-4S] cluster, Biochemistry 48 (2009) 6240-6248.

[33] T. Happe, A. Kaminski, Differential regulation of the Fe-hydrogenase during anaerobic adaptation in the green alga *Chlamydomonas reinhardtii*, Eur. J. Biochem. 269 (2002) 1022-1032.

[34] A. Hemschemeier, S. Fouchard, L. Cournac, G. Peltier, T. Happe, Hydrogen production by *Chlamydomonas reinhardtii*: an elaborate interplay of electron sources and sinks, Planta 227 (2008) 397-407.

[35] V. Chochois, D. Dauvillée, A. Beyly, D. Tolleter, S. Cuiné, H. Timpano, S. Ball, L. Cournac, G. Peltier, Hydrogen production in *Chlamydomonas*: Photosystem II-dependent and -independent pathways differ in their requirement for starch metabolism, Plant Physiology 151 (2009) 631-640.

[36] N. Nelson, C. Yocum, Structure and function of photosystems I and II, Annu Rev Plant Biol 57 (2006) 521-565.

[37] A. Terauchi, S. Lu, M. Zaffagnini, S. Tappa, M. Hirasawa, J. Tripathy, D. Knaff, P. Farmer, S. Lemaire, T. Hase, S. Merchant, Pattern of expression and substrate specificity of chloroplast ferredoxins from *Chlamydomonas reinhardtii*, J Biol Chem 284 (2009) 25867-25878.

[38] I. Yacoby, S. Pochekailov, H. Toporik, M. Ghirardi, P. King, S. Zhang, Photosynthetic electron partitioning between [FeFe]-hydrogenase and ferredoxin:NADP+-oxidoreductase (FNR) enzymes in vitro, Proc Natl Acad Sci USA 108 (2011) 9396-9401.

[39] D. Tolleter, B. Ghysels, J. Alric, D. Petroutsos, I. Tolstygina, D. Krawietz, T. Happe, P. Auroy, J. Adriano, A. Beyly, S. Cuiné, J. Plet, I. Reiter, B. Genty, L. Cournac, M. Hippler, G. Peltier, Control of hydrogen photoproduction by the proton gradient generated by cyclic electron flow in *Chlamydomonas reinhardtii*, Plant Cell Epub ahead of print (2011).

[40] O. Kruse, J. Rupprecht, K. Bader, S. Thomas-Hall, P. M. Schenk, G. Finazzi, B. Hankamer, Improved photobiological $H_2$ production in engineered green algal cells, J Biol Chem 280 (2005) 34170-34177.

[41] T. Antal, A. Volgusheva, G. Kukarskih, T. Krendeleva, A. Rubin, Relationships between $H_2$ photoproduction and different electron transport pathways in sulfur-deprived *Chlamydomonas reinhardtii*, Int. J. Hydrogen Energy 34 (2009) 9087-9094.

[42] Y. Munekage, M. Hojo, J. Meurer, T. Endo, M. Tasaka, T. Shikanai, PGR5 is involved in cyclic electron flow around photosystem I and is essential for photoprotection in *Arabidopsis*, Cell 110 (2002) 361-371.

[43] G. DalCorso, P. Pesaresi, S. Masiero, E. Aseeva, D. Schünemann, G. Finazzi, P. Joliot, R. Barbato, D. Leister, A complex containing PGRL1 and PGR5 is involved in the switch between linear and cyclic electron flow in *Arabidopsis*, Cell 132 (2008) 273-285.

[44] M. Adams, The structure and mechanism of iron-hydrogenases, Biochim. Biophys. Acta 1020 (1990) 115-145.

[45] C. D. Baffert, M, L. Cournac, B. Burlat, B. Guigliarelli, P. Bertrand, L. Girbal, C. Léger, Hydrogen-activating enzymes: activity does not correlate with oxygen sensitivity, Angew Chem Int Ed Engl 47 (2008) 2052-2054.

[46] P. E. M. Siegbahn, J. W. Tye, M. B. Hall, Computational studies of [NiFe] and [FeFe] hydrogenases, Chemical Reviews 107 (2007) 4414-4435.

[47] J. Fontecilla-Camps, A. Volbeda, C. Cavazza, Y. Nicolet, Structure/function relationships of [NiFe]- and [FeFe]-hydrogenases, Chem. Rev. 107 (2007) 4273-4303.

[48] Y. Montet, P. Amara, A. Volbeda, X. Vernede, E. Hatchikian, M. Field, M. Frey, J. Fontecilla-Camps, Gas access to the active site of Ni—Fe hydrogenases probed by X-ray crystallography and molecular dynamics, Nature Structural Biology 4 (1997) 523-526.

[49] V. Teixeira, A. Baptista, C. Soares, Pathways of $H_2$ toward the active site of [NiFe]-hydrogenase, Biophys. J. 91 (2006) 2035-2045.

[50] M. Rousset, Y. Montet, B. Guigliarelli, N. Forget, M. Asso, P. Bertrand, J. Fontecilla-Camps, E. Hatchikian, [3Fe-4S] to [4Fe-4S] cluster conversion in Desulfovibrio fructosovorans [NiFe] hydrogenase by site-directed mutagenesis, Proc Natl Acad Sci USA 95 (1998) 11625-11630.

[51] F. Leroux, S. Dementin, B. Burlat, L. Cournac, A. Volbeda, S. Champ, L. Martin, B. Guigliarelli, P. Bertrand, J. Fontecilla-Camps, M. Rousset, C. Léger, Experimental approaches to kinetics of gas diffusion in hydrogenase, Proc Natl Acad Sci USA 105 (2008) 11188-11193.

[52] O. Duché, S. Elsen, L. Cournac, A. Colbeau, Enlarging the gas access channel to the active site renders the regulatory hydrogenase HupUV of *Rhodobacter capsulatus* $O_2$ sensitive without affecting its transductory activity, The FEBS Journal 272 (2005) 3899-3908.

[53] A. Volbeda, Y. Montet, X. Vernede, E. Hatchikian, J. Fontecilla-Camps, High-resolution crystallographic analysis of Desulfovibrio fructosovorans, Int. J. Hydrogen Energy 27 (2002).

[54] R. Surzycki, L. Cournac, G. Peltier, J. Rochaix, Potential for hydrogen production with inducible chloroplast gene expression in *Chlamydomonas*, Proc Natl Acad Sci USA 104 (2007) 17548-17553.

[55] M. Seibert, T. Flynn, M. Ghirardi, Strategies for improving oxygen tolerance of algal hydrogen production, in: J. Miyake, T. Matsunaga, A. S. Pietro (Eds.), Biohydrogen II, Elsevier Science, 2001, pp. 65-76.

[56] S. Dementin, F. Leroux, L. Cournac, A. de Lacey, A. Volbeda, C. Léger, B. Burlat, N. Martinez, S. Champ, L. Martin, O. Sanganas, M. Haumann, V. Fernandez, B. Guigliarelli, J. Fontecilla-Camps, M. Rousset, Introduction of methionines in the gas channel makes [NiFe] hydrogenase aero-tolerant, J Am Chem Soc 131 (2009) 10156-10164.

[57] A. Melis, Green alga hydrogen production: progress, challenges and prospects, Int. J. Hydrogen Energy 27 (2002) 1217-1228.

[58] B. Esper, A. Badura, M. Rögner, Photosynthesis as a power supply for (bio-) hydrogen production, Trends in Plant Science 11 (2006) 543-549.

[59] D. Mulder, E. Boyd, R. Sarma, R. Lange, J. Endrizzi, J. Broderick, J. Peters, Stepwise [FeFe]-hydrogenase H-cluster assembly revealed in the structure of HydA (DeltaEFG), Nature 465 (2010) 248-251.

[60] S. McGlynn, S. Ruebush, A. Naumov, L. Nagy, A. Dubini, P. King, J. Broderick, M. Posewitz, J. Peters, In vitro activation of [FeFe] hydrogenase: new insights into hydrogenase maturation, J Biol Inorg Chem 12 (2007) 443-447.

[61] A. Coraglitti, M. Belingi, S. Franklin, S. Mayfield, Molecular factors affecting the accumulation of recombinant proteins in the *Chlamydomonas reinhardtii* chloroplast, Molecular Biotechnology 48 (2011) 60-75.

[62] J. Quinn, P. Barraco, M. Eriksson, S. Merchant, Coordinate copper- and oxygen-responsive Cyc6 and Cpx1 expression in *Chlamydomonas* is mediated by the same element, J Biol Chem 275 (2000) 6080-6089.

[63] K. Sybirna, T. Antoine, P. Lindberg, V. Fourmond, M. Rousset, V. Méjean, H. Bottin, *Shewanella oneidensis*: a new and efficient system for expression and maturation of heterologous [Fe—Fe] hydrogenase from *Chlamydomonas reinhardtii*, BMC Biotechnology 8 (2008) Open Access.

[64] S. Oard, Deciphering a mechanism of membrane permeabilization by α-hordothionin peptide Biochimica et Biophysica Acta—Biomembranes Article in Press (2011).

[65] S. Oard, F. Enright, Expression of the antimicrobial peptides in plants to control phytopathogenic bacteria and fungi Plant Cell Reports 25 (2006) 561-572.

[66] S. Oard, F. Enright, B. Li, Structural changes induced in thionins by chloride anions as determined by molecular dynamics simulations, Biophys. Chem. 147 (2010) 42-52.

[67] S. Oard, B. Karki, F. Enright, Is there a difference in metal ion-based inhibition between members of thionin family: molecular dynamics simulation study, Biophys. Chem. 130 (2007) 65-75.

[68] D. Liu, S. Oard, J. Oard, High transgene expression levels in sugarcane (*Saccharum officinarum* L.) driven by the rice ubiquitin promoter RUBQ2 Plant Science 165 (2003) 743-750.

[69] S. Oard, Hydrogen and biofuels, Louisiana Agriculture Fall (2009) 2.

[70] S. Oard, Plant defensive peptides. International Patent Application, USA, 2011, p. 68.

[71] S. Oard, J. Ham, M. A. Cohn, Thionins—nature's weapons of mass protection, Small Wonders: Peptides for Disease Control, vol. in press, ACS Books, p. 39 pps.

[72] N. Fischer, J.-D. Rochaix, The flanking regions of PsaD drive efficient gene expression in the nucleus of the green alga *Chlamydomonas reinhardtii*, Molecular Genetics and Genomics 265 (2001).

[73] M. Posewitz, P. King, S. Smolinski, L. Zhang, M. Seibert, M. Ghirardi, Discovery of two novel radical S-adenosylmethionine proteins required for the assembly of an active [Fe] hydrogenase, J Biol Chem 279 (2004) 25711-25720.

[74] P. Ferrante, C. Catalanotti, G. Bonente, G. Giuliano, An Optimized, Chemically Regulated Gene Expression System for *Chlamydomonas*, PLoS ONE 3 (2008) 3200.

[75] Y. Shyu, H. Liu, X. Deng, C. Hu, Identification of new fluorescent protein fragments for bimolecular fluorescence complementation analysis under physiological conditions, Biotechniques 40 (2006) 61-66.

[76] P. Campbell, T. Beer, D. Batten, Greenhouse gas sequestration by algae-energy and greenhouse gas life cycle studies. http://www.csiro.au/org/EnergyTransformedFlagship.html, CSIRO, 2009.

[77] A. Alabi, M. Tampier, E. Bibeau, Microalgae technologies and processes for biofuels/bioenergy production in British Columbia. Current Technology, Suitability, & Barriers to Implementation, Seed & Science Ltd, 2009.

[78] R. Craggs, S. Heubeck, T. Lundquist, J. Benemann, Algal biofuels from wastewater treatment high rate algal ponds, Water Sci Technol 63 (2011) 660-665.

[79] The Energy Information Administration (2011) Electricity. http://205.254.135.24/electricity/data.cfm#electriccosts

[80] IBISWorld, Report, August 2011.

[81] Yacoby, I., et al., Photosynthetic electron partitioning between [FeFe]-hydrogenase and ferredoxin:NADP+-oxidoreductase (FNR) enzymes in vitro. Proc Natl Acad Sci USA, 2011. 108: p. 9396-9401.

[82] McGlynn, S., et al., In vitro activation of [FeFe] hydrogenase: new insights into hydrogenase maturation. Journal of Biological Inorganic Chemistry, 2007. 12: p. 443-7.

[83] Ghirardi, M., R. Togasaki, and M. Seibert, Oxygen sensitivity of algal $H_2$-production. Applied biochemistry and biotechnology, 1997. 63-65: p. 141-151.

[84] Ghirardi, M., et al., Hydrogenases and hydrogen photoproduction in oxygenic photosynthetic organisms. Annual Review of Plant Biology, 2007. 58: p. 71-91.

[85] Posewitz, M., et al., Discovery of two novel radical S-adenosylmethionine proteins required for the assembly of an active [Fe] hydrogenase. J. Biol. Chem., 2004. 279: p. 25711-20.

[86] Neupert, J., D. Karcher, and R. Bock, Generation of *Chlamydomonas* strains that efficiently express nuclear transgenes. The Plant Journal, 2009. 57(6): p. 1140-50.

[87] Quinn, J., et al., Coordinate copper- and oxygen-responsive Cyc6 and Cpx1 expression in *Chlamydomonas* is mediated by the same element. Journal of Biological Chemistry, 2000. 275: p. 6080-9.

[88] Ferrante, P., et al., An Optimized, Chemically Regulated Gene Expression System for *Chlamydomonas*. PLoS ONE, 2008. 3: p. 3200.

[89] Shimogawara, K., et al., High-efficiency transformation of *Chlamydomonas reinhardtii* by electroporation. Genetics, 1998. 148: p. 1821-1828.

[90] Harris, E. H., The *Chlamydomonas* sourcebook: introduction to *Chlamydomonas* and its laboratory use. Vol. 1. 2009: Access Online via Elsevier.

[91] Peters, J. W., et al., A radical solution for the biosynthesis of the H-cluster of hydrogenase. FEBS letters, 2006. 580(2): p. 363-367.

[92] Ma, W., et al., Treatment with $NaHSO_3$ greatly enhances photobiological $H_2$ production in the green alga*Chlamydomonas* *reinhardtii*. Bioresource technology, 2011. 102(18): p. 8635-8638.
[93] Sodeinde, O. A. and K. L. Kindle, Homologous recombination in the nuclear genome of *Chlamydomonas reinhardtii*. Proceedings of the National Academy of Sciences, 1993. 90(19): p. 9199-9203.
[94] Melis, A., Photosynthetic $H_2$ metabolism in *Chlamydomonas reinhardtii* (unicellular green algae). Planta, 2007. 226(5): p. 1075-1086.
[95] Hemschemeier, A., A. Melis, and T. Happe, Analytical approaches to photobiological hydrogen production in unicellular green algae. Photosynthesis Research, 2009. 1-2: p. 523-540.

What is claimed is:

1. A microorganism, comprising a modified gene encoding a $H_2$-forming $H_2$ase and one or more genes encoding maturation proteins that mediate the maturation of said $H_2$ase; wherein a nucleic acid molecule encoding said $H_2$ase is genetically engineered for high expression at more than 2% $O_2$ by silent substitutions of nucleotides, wherein said $H_2$ase gene is expressed at an $O_2$ concentration of about 0% to more than 2%; wherein at least one of said genes encoding a maturation protein is expressed under less than 0.1% $O_2$; wherein said microorganism is selected from the group consisting of algae, bacteria, and cyanobacteria; exhibiting an increased level of $H_2$ production when compared to an otherwise identical microorganism, but lacking said $H_2$ase gene and the engineered genes encoding maturation proteins.

2. The microorganism of claim 1 wherein said microorganism is an alga.

3. The microorganism of claim 1 wherein said microorganism is a bacterium.

4. The microorganism of claim 1 wherein said microorganism is a cyanobacterium.

5. The microorganism of claim 2 wherein said microorganism is *Chlamydomonas reinhardtii*.

6. The microorganism of claim 1, wherein said $H_2$ase has at least about 85% sequence identity to the $H_2$-forming $H_2$ase selected from the group consisting of $H_2$-forming $H_2$ases from *Clostridium pasteurianum* and *Clostridium acetobutylicum*.

7. The microorganism of claim 1, wherein said $H_2$ase has at least about 85% sequence identity to the *Desulfovibrio vulgaris* $H_2$-forming $H_2$ase.

8. The microorganism of claim 1, wherein said modified $H_2$ase gene comprises a nucleotide sequence selected from the group consisting of the sequences set forth in SEQ ID NO: 3, 5, or 6.

9. The microorganism of claim 1, wherein said modified $H_2$ase gene comprises a nucleotide sequence having at least 85% sequence identity to the sequence set forth in SEQ ID NO: 3, wherein said nucleotide sequence encodes a $H_2$ase having at least 85% sequence identity to SEQ ID NO:4.

* * * * *

SEQUENCE LISTING

<160> NUMBER OF SEQ ID NOS: 16

<210> SEQ ID NO 1
<211> LENGTH: 4663
<212> TYPE: DNA
<213> ORGANISM: Chlamydomonas reinhardtii

<400> SEQUENCE: 1

```
tcttacatga acacacaaac actctcgcag gcactagcct caaaccctcg aaaccttttt      60
ccaacagttt acaccccaat tcggacgccg ctccaagctc gctccgttgc tccttcatcg     120
caccacctat tatttctaat atcgtagacg cgacaagatg tcggcgctcg tgctgaagcc     180
ctgcgcggcc gtgtctattc gcggcagctc ctgcagggcg cggcaggtcg ccccccgcgc     240
tccgctcgca gccagcaccg tgcgtgtagc ccttgcaaca cttgaggcgc ccgcacgccg     300
cctaggtgag ggcgacgcag tgaacgcagt ttcgatgggt cactttgtcg cttttgcgga     360
agcctccgaa acgtcccgcg aggttcaaac ggccccgaat gaccacaccc atatggccac     420
tggaaataat aacgcaggca acgtcgcttg cgcggctgcc gcacccgctg cggaggcgcc     480
tttgagtcat gtccagcagg cgctcgccga gcttggtgag cgaacggccg agcgagcgcg     540
cacgcattgt tgtggtcaag tctctccact cagtccgacc ccccacacgg cgtagggtc      600
tgaagtccac caactcctca cacacccaa ggaagggacg taagccccc tggctacgct       660
ttacccagca gccacagcga cagagcgccc caacataggc tcgagataga acgcacctga     720
actgtgacac ttacaatgga aaggaactgc ggatggcctt aaagtcaagc attttgtgac     780
gagtcggctc ggaatcccca tcggcgcccg tccgttcgtc ttcatcaccg cctgaaacgg     840
cgcacgcgca atagtgcgca cttgatgcct ttcggtccaa cgcctctgtc agctaacact     900
ttccagggcc agcgcggact cgagaaccct ctttcctggc aaccttggtt tggctggcac     960
ctggcaacct tggtttggct ggcaccaacc ttgacccaca taaatctctc ccccccccc    1020
ttatgccac agccaagccc aaggacgacc ccacgcgcaa gcacgtctgc gtgcaggtgg    1080
ctccggccgt tcgtgtcgct attgccgaga ccctgggcct ggcgccgggc gccaccaccc    1140
ccaagcagct ggccgagggc ctccgccgcc tcggctttga cgaggtaggt gcgctcgctg    1200
ctgcagtgcc caacacgcat cttccagctc accgcctacc agtcagcacc ttggcatgca    1260
tgcttggcgc atctgccgcc tcattgccgc ctcgcggcct cgccgctgcc tgcatcaagc    1320
ctgcctgcct gcctgcccgc cctcacgccc aggtgtttga cacgctgttt ggcgccgacc    1380
tgaccatcat ggaggagggc agcgagctgc tgcaccgcct caccgagcac ctggaggccc    1440
acccgcactc cgacgagccg ctgccatgt tcaccagctg ctgccccggc tggatcggtg     1500
agcagcgcgg cgtgcttgct tagggcccca taacctgtct tgggccccc gcgtccgcct    1560
ctccacctac ctgcaacatg tacgtgccta cggtattgtc gcatgtctct tgacgatttg    1620
ggtcgacctt acctttgcct tgtgtccttt ctccacccc acccgcctct ttcctcgccg    1680
gccccctcg cgcagctatg ctgagaaat cttacccgga cctgatcccc tacgtgagca    1740
gctgcaagag cccccagatg atgctggcgg ccatggtcaa gtcctaccta gcggaaaaga    1800
```

```
agggcatcgc gccaaaggac atggtcatgg tgtccatcat gccctggtga gagccccggg    1860
ggggaggcgg ggattgcggg gggcaggggg tgcggggggc agggtttgcc ggcgtggtgg    1920
aaggctgccc caggatggtc gaggaggccc gccgtggggg tctgccggcg taaaatttgg    1980
tatgtgggtc gaatggttca gccgcggagc catggcgccg cccctgcacc agcattcaag    2040
ctgcctgtgc tgacccaacc cacctgcttc accgccctgc acaccggt gcgcagcacg      2100 cgcaagcagt cggaggctga ccgcgactgg ttctgtgtgg acgccgaccc caccctgcgc    2160
cagctggacc acgtcatcac caccgtggag ctgggcaaca tcttcaaggt gggccggggg    2220 gcgggggggcg ggcgcgcggg gcgttatgat tcgggcctta aggggttgttc gcatcatcat  2280 cagaaagccc acccagcgcg gaaatgcgag tcgaacgcga gtaggagtag tagtactcct    2340
cgctctctgg cactgctgta agcgcacacg cgcacccaca cgcacacgca cacgcacacg    2400
caaccgcaca cgtgcaccaa cgtcacatcc acacgcagga gcgcggcatc aacctggccg    2460
agctgcccga gggcgagtgg gacaatccaa tgggcgtggg ctcggcgcc ggcgtgctgt     2520 tcggcaccac cggcggtgtc atggaggcgg cgctgcgcac ggtgggtctg tgagagccgg    2580
ttgattggcc cggcagaacg catacacttg ctgaacctttt gatgcgggat aagcaaggct   2640
accgatccgc gtcttttttac acctgtttat cacgtcgctg agcaagctcg tgacacctgc   2700
aggcctatga gctgttcacg ggcacgccgc tgccgcgcct gagcctgagc gaggtgcgcg    2760
gcatggacgc catcaaggag accaacatca ccatggtgcc cgcgcccggg tccaagtttg    2820
aggagctgct gaagcaccgc gccgccgcgc gcgccgaggc cgccgcgcac ggcaccccccg   2880 ggccgctggc ctgggacggc ggcgcgggct tcaccagcga ggacggcagg ggcggcatca    2940
cactgcgcgt ggccgtggcc aacgggctgg gcaacgccaa gaagctgatc accaagatgc    3000
aggccggcga ggccaagtac gactttgtgg agatcatggc ctgccccgcg ggctgtgtgg    3060
gcggcggcgg ccagcccgc tccaccgaca aggccatcac gcagaagcgg caggcggcgc     3120
tgtacaacct ggacgagaag tgagcggcg gcgctgctgg gattgggcag gggagggaag     3180
ggactgcggg gcagggtgcg gcgggaaacg gaaatgggca aggctcgagg tggagggcgg    3240
ggtgggttgg ggttacttgc tacaggttgg cgggcaggat gtgatggaag cagtgtggag    3300
gaggtgtgcg tagggtcccg acgacggtat tcgcacgagc aaagagggtc ggcacttcct    3360
gacacaatgt gcgcctgcac gtgcgctcct gttgctgccc caggtccacg ctgcgccgca    3420
gccacgagaa cccgtccatc cgcgagctgt acgacacgta cctcggagag ccgctgggcc    3480
acaaggtggg gggggttgt aactaccagc ccaaatgacg gggctggtcg ggggcgttgg     3540
agaggcgggc cggagggag gcgggctggg tgtggggcaa cagcaggtga agggacgggg     3600
gggcacactg ggcagggcgg tacatgcctt gtcctgatag ctaccacac gcgactgttg     3660 ctacatggat gcatgacgtg tgccgtgtgc ttgacccctg caggcgcacg agctgctgca    3720
cacccactac gtggccggcg gcgtggagga gaaggacgag aagaagtgag gagcgccaga    3780 ggctcttttgg gcggagacag cttcaaagcg agggggcgta ttagcagtac cgtaaatatg    3840
cactgatggg tgatgcgggt gtcctccttt atattgaatg gggtcaaaat aggcggcggg    3900
tcaaatgttt cctttttgag tggtgtcaca gcatggggca cgtgtgcgga ggccagttgc    3960
cctccagtgc acgcgctccc ggtgtgtggc cgcactggcc ttggataatg caccggtgga    4020
ggattatgga agaggggac tcagaaggct cattattgga caatgcctgg tctcttccac     4080
attggtgtga gcgcggctcc gcataggctg ttcactgcac gctggcatta ggcgtaggta    4140
ctggcatgag ggagcgcggc ttgctaaccg aatggcgtat ccctccaggg cacgtcggaa    4200
```

| | |
|---|---|
| tggcgcgtgc ccatcaacgc aaattcttgg ccttcatcgc ttctggatat tgaagctgca | 4260 |
| caaacctgca ttctatttgc ttgtttacac gtgccccaat cttggttgga agctaaacat | 4320 |
| gtttgggaac aattcatctt actaaagcgt gtgggggttg aggatgcgca cgttgtgcgc | 4380 |
| tggtgggtgg gcgggaacgt gggtagcatt taggctagct ggcatacgac aacggggccc | 4440 |
| gtgaggattg agcacttgac tcgcgaactt atgaacgtag cgctttatac ccaccgtatg | 4500 |
| cgattgacgt tggtgtaggc aaccaggcgg taggaaggcg agagatgca ttgcaaacgc | 4560 |
| ctgtaaaaga acggcatagc tactagacac tctgatgtgg acccttggcg cagccacgac | 4620 |
| aggagaggtg tgcatcagcc gcttgtaagc acgcacttct gag | 4663 |

<210> SEQ ID NO 2
<211> LENGTH: 1494
<212> TYPE: DNA
<213> ORGANISM: Chlamydomonas reinhardtii

<400> SEQUENCE: 2

| | |
|---|---|
| atgtcggcgc tcgtgctgaa gccctgcgcg gccgtgtcta ttcgcggcag ctcctgcagg | 60 |
| gcgcggcagg tcgcccccg cgctccgctc gcagccagca ccgtgcgtgt agcccttgca | 120 |
| acacttgagg cgcccgcacg ccgcctaggc aacgtcgctt gcgcggctgc cgcacccgct | 180 |
| gcggaggcgc ctttgagtca tgtccagcag gcgctcgccg agcttgccaa gcccaaggac | 240 |
| gaccccacgc gcaagcacgt ctgcgtgcag gtggctccgg ccgttcgtgt cgctattgcc | 300 |
| gagaccctgg gcctggcgcc gggcgccacc accccaagc agctggccga gggcctccgc | 360 |
| cgcctcggct ttgacgaggt gtttgacacg ctgtttggcg ccgacctgac catcatggag | 420 |
| gagggcagcg agctgctgca ccgcctcacc gagcacctgg aggcccaccc gcactccgac | 480 |
| gagccgctgc ccatgttcac cagctgctgc cccggctgga tcgctatgct ggagaaatct | 540 |
| tacccggacc tgatccccta cgtgagcagc tgcaagagcc cccagatgat gctggcggcc | 600 |
| atggtcaagt cctacctagc ggaaaagaag ggcatcgcgc caaaggacat ggtcatggtg | 660 |
| tccatcatgc cctgcacgcg caagcagtcg gaggctgacc gcgactggtt ctgtgtggac | 720 |
| gccgacccca ccctgcgcca gctggaccac gtcatcacca ccgtggagct gggcaacatc | 780 |
| ttcaaggagc gcggcatcaa cctggccgag ctgcccgagg gcgagtggga caatccaatg | 840 |
| ggcgtgggct cgggcgccgg cgtgctgttc ggcaccaccg gcggtgtcat ggaggcggcg | 900 |
| ctgcgcacgg cctatgagct gttcacgggc acgccgctgc cgcgcctgag cctgagcgag | 960 |
| gtgcgcggca tggacggcat caaggagacc aacatcacca tggtgcccgc gcccgggtcc | 1020 |
| aagtttgagg agctgctgaa gcaccgcgcc gccgcgcgcg ccgaggccgc cgcgcacggc | 1080 |
| accccgggc gctggcctg gacggcggc gcgggcttca ccagcgagga cggcaggggc | 1140 |
| ggcatcacac tgcgcgtggc cgtggccaac gggctgggca cgccaagaa gctgatcacc | 1200 |
| aagatgcagg ccggcgaggc caagtacgac tttgtggaga tcatggcctg ccccgcgggc | 1260 |
| tgtgtgggcg gcggcggcca gccccgctcc accgacaagg ccatcacgca gaagcggcag | 1320 |
| gcggcgctgt acaacctgga cgagaagtcc acgctgcgcc gcagccacga gaacccgtcc | 1380 |
| atccgcgagc tgtacgacac gtacctcgga gagccgctgg ccacaaggc gcacgagctg | 1440 |
| ctgcacaccc actacgtggc cggcggcgtg gaggagaagg acgagaagaa gtga | 1494 |

<210> SEQ ID NO 3
<211> LENGTH: 1332
<212> TYPE: DNA
<213> ORGANISM: Chlamydomonas reinhardtii

<400> SEQUENCE: 3

```
gctagcgccg ctcctgctgc tgaggctcct ctgagccacg tgcagcaggc cctggctgag      60
ctggccaagc caaggacgac ccccacccgc aagcacgtgt gcgtccaggt cgcccctgct     120
gtgcgcgtgg ccattgctga gactctgggc ctggctcccg gcgctaccac ccctaagcag     180
ctggctgagg gcctgcgccg cctgggcttt gatgaggtgt tcgacaccct gttcggcgcc     240
gacctgacca tcatggagga gggctctgag ctgctgcacc gcctgaccga gcacctggag     300
gctcacccte acagcgacga gccectgccc atgttcacca gctgctgccc cggctggatc     360
gccatgctgg agaagtccta ccccgacctg atccectacg tgtccagctg caagagcccc     420
cagatgatgc tggccgctat ggtcaagagc tacctggccg agaagaaggg cattgcccc      480
aaggacatgg tcatggtgtc catcatgccc tgcacgcgca agcagagcga ggccgaccgc     540
gactggttct gcgtcgacgc agaccctacc ctgcgccagc tggaccacgt gatcaccacc     600
gtcgagctgg gcaacatctt caaggagcgc ggcatcaacc tggcggagct gcctgagggc     660
gagtgggaca accctatggg cgtgggttct ggcgctggcg tgctgttcgg caccactggc     720
ggtgtcatgg aggccgccct gcgcaccgct tacgagctgt tcaccggcac ccctctgccc     780
cgcctgtctc tgtctgaggt ccgcggcatg acggcatca aggagactaa catcacgatg      840
gtgcccgctc ccggcagcaa gttcgaggag ctcctgaagc accgcgctgc cgctcgcgct     900
gaggctgctg ctcacggtac tcccggtcct ctggcttggg acggcggtgc tggcttcact     960
agcgaggacg tcgcggcgg tattaccctg cgcgtggcag tggctaacgg cctgggcaac    1020
gccaagaagc tgatcaccaa gatgcaggcc ggcgaggcga gtacgacttc gtcgagatc    1080
atggcctgcc ccgctggctg cgtcggtggt ggtggccagc ctcgcagcac cgacaaggcc    1140
atcacccaga agcgccaggc cgcgctgtac aacctggacg agaagtccac cctgcgccgc    1200
agccacgaga accccagcat ccgcgagctg tacgacacct acctgggcga gcccctgggc    1260
cacaaggctc acgagctgct ccacacccac tacgtggcag gcggcgtcga ggagaaggac    1320
gagaagaagt ag                                                         1332
```

<210> SEQ ID NO 4
<211> LENGTH: 497
<212> TYPE: PRT
<213> ORGANISM: Chlamydomonas reinhardtii

<400> SEQUENCE: 4

```
Met Ser Ala Leu Val Leu Lys Pro Cys Ala Ala Val Ser Ile Arg Gly
1               5                   10                  15

Ser Ser Cys Arg Ala Arg Gln Val Ala Pro Arg Ala Pro Leu Ala Ala
            20                  25                  30

Ser Thr Val Arg Val Ala Leu Ala Thr Leu Glu Ala Pro Ala Arg Arg
        35                  40                  45

Leu Gly Asn Val Ala Cys Ala Ala Ala Pro Ala Ala Glu Ala Pro
    50                  55                  60

Leu Ser His Val Gln Gln Ala Leu Ala Glu Leu Ala Lys Pro Lys Asp
65                  70                  75                  80

Asp Pro Thr Arg Lys His Val Cys Val Gln Val Ala Pro Ala Val Arg
                85                  90                  95

Val Ala Ile Ala Glu Thr Leu Gly Leu Ala Pro Gly Ala Thr Thr Pro
            100                 105                 110

Lys Gln Leu Ala Glu Gly Leu Arg Arg Leu Gly Phe Asp Glu Val Phe
        115                 120                 125
```

```
Asp Thr Leu Phe Gly Ala Asp Leu Thr Ile Met Glu Glu Gly Ser Glu
    130                 135                 140
Leu Leu His Arg Leu Thr Glu His Leu Glu Ala His Pro His Ser Asp
145                 150                 155                 160
Glu Pro Leu Pro Met Phe Thr Ser Cys Cys Pro Gly Trp Ile Ala Met
                165                 170                 175
Leu Glu Lys Ser Tyr Pro Asp Leu Ile Pro Tyr Val Ser Ser Cys Lys
            180                 185                 190
Ser Pro Gln Met Met Leu Ala Ala Met Val Lys Ser Tyr Leu Ala Glu
        195                 200                 205
Lys Lys Gly Ile Ala Pro Lys Asp Met Val Met Val Ser Ile Met Pro
210                 215                 220
Cys Thr Arg Lys Gln Ser Glu Ala Asp Arg Asp Trp Phe Cys Val Asp
225                 230                 235                 240
Ala Asp Pro Thr Leu Arg Gln Leu Asp His Val Ile Thr Thr Val Glu
                245                 250                 255
Leu Gly Asn Ile Phe Lys Glu Arg Gly Ile Asn Leu Ala Glu Leu Pro
            260                 265                 270
Glu Gly Glu Trp Asp Asn Pro Met Gly Val Gly Ser Gly Ala Gly Val
        275                 280                 285
Leu Phe Gly Thr Thr Gly Gly Val Met Glu Ala Ala Leu Arg Thr Ala
290                 295                 300
Tyr Glu Leu Phe Thr Gly Thr Pro Leu Pro Arg Leu Ser Leu Ser Glu
305                 310                 315                 320
Val Arg Gly Met Asp Gly Ile Lys Glu Thr Asn Ile Thr Met Val Pro
                325                 330                 335
Ala Pro Gly Ser Lys Phe Glu Glu Leu Leu Lys His Arg Ala Ala Ala
            340                 345                 350
Arg Ala Glu Ala Ala His Gly Thr Pro Gly Pro Leu Ala Trp Asp
        355                 360                 365
Gly Gly Ala Gly Phe Thr Ser Glu Asp Gly Arg Gly Ile Thr Leu
370                 375                 380
Arg Val Ala Val Ala Asn Gly Leu Gly Asn Ala Lys Lys Leu Ile Thr
385                 390                 395                 400
Lys Met Gln Ala Gly Glu Ala Lys Tyr Asp Phe Val Glu Ile Met Ala
                405                 410                 415
Cys Pro Ala Gly Cys Val Gly Gly Gly Gln Pro Arg Ser Thr Asp
            420                 425                 430
Lys Ala Ile Thr Gln Lys Arg Gln Ala Ala Leu Tyr Asn Leu Asp Glu
        435                 440                 445
Lys Ser Thr Leu Arg Arg Ser His Glu Asn Pro Ser Ile Arg Glu Leu
450                 455                 460
Tyr Asp Thr Tyr Leu Gly Glu Pro Leu Gly His Lys Ala His Glu Leu
465                 470                 475                 480
Leu His Thr His Tyr Val Ala Gly Gly Val Glu Glu Lys Asp Glu Lys
                485                 490                 495
Lys

<210> SEQ ID NO 5
<211> LENGTH: 1747
<212> TYPE: DNA
<213> ORGANISM: Chlamydomonas reinhardtii
```

```
<400> SEQUENCE: 5
ctccaccttc gccgcccgcg ttggcgctaa gcccgctgta cgcggtgctc gccccgccag        60
ccgcatgagc tgcatggcct acaaggtcac cctgaagacc ccttcgggcg acaagaccat       120
tgagtgcccc gctgacacct acatcctgga cgctgctgag gaggccggcc tggacctgcc       180
ctactcttgc cgcgctggtg cttgctccag ctgcgccggc aaggtcgctg ccggcaccgt       240
ggaccagtcg gaccagtcct tcctggacga tgcccagatg ggcaacggct tcgtgctgac       300
ctgcgtggcc taccccacct cggactgcac catccagacc caccaggagg aggccctgta       360
caccggtggt ggtgcatctt ggagccaccc gcagttcgag aagagcggcg gtggtgctag       420
cgccgctcct gctgctgagg ctcctctgag ccacgtgcag caggccctgg ctgagctggc       480
caagcccaag gacgacccca cccgcaagca cgtgtgcgtc caggtcgccc ctgctgtgcg       540
cgtggccatt gctgagactc tgggcctggc tcccggcgct accacccta agcagctggc       600 tgagggcctg cgccgcctgg gctttgatga ggtgttcgac accctgttcg gcgccgacct       660
gaccatcatg gaggagggct ctgagctgct gcaccgcctg accgagcacc tggaggctca       720
ccctcacagc gacgagcccc tgcccatgtt caccagctgc tgccccggct ggatcgccat       780
gctggagaag tcctaccccg acctgatccc ctacgtgtcc agctgcaaga gccccagat       840 gatgctggcc gctatggtca agagctacct ggccgagaag aagggcattg cccccaagga       900
catggtcatg gtgtccatca tgccctgcac gcgcaagcag agcgaggccg accgcgactg       960
gttctgcgtc gacgcagacc ctaccctgcg ccagctggac cacgtgatca ccaccgtcga      1020
gctgggcaac atcttcaagg agcgcggcat caacctggcg gagctgcctg agggcgagtg      1080
ggacaaccct atgggcgtgg gttctggcgc tggcgtgctg ttcggcacca ctggcggtgt      1140
catggaggcc gccctgcgca ccgcttacga gctgttcacc ggcaccccctc tgccccgcct      1200 gtctctgtct gaggtccgcg gcatggacgg catcaaggag actaacatca cgatggtgcc      1260
cgctcccggc agcaagttcg aggagctcct gaagcaccgc gctgccgctc gcgctgaggc      1320
tgctgctcac ggtactcccg gtcctctggc ttgggacggc ggtgctggct tcactagcga      1380
ggacggtcgc ggcggtatta cccctgcgcgt ggcagtggct aacggcctgg caacgccaa      1440 gaagctgatc accaagatgc aggccggcga ggcgaagtac gacttcgtcg agatcatggc      1500
ctgccccgct ggctgcgtcg gtggtggtgg ccagcctcgc agcaccgaca aggccatcac      1560
ccagaagcgc caggccgcgc tgtacaacct ggacgagaag tccaccctgc gccgcagcca      1620
cgagaacccc agcatccgcg agctgtacga caccctacctg ggcgagcccc tgggccacaa      1680
ggctcacgag ctgctccaca cccactacgt ggcaggcggc gtcgaggaga aggacgagaa      1740
gaagtag                                                                1747

<210> SEQ ID NO 6
<211> LENGTH: 2908
<212> TYPE: DNA
<213> ORGANISM: Chlamydomonas reinhardtii

<400> SEQUENCE: 6
tcgggtttcg ccacctctga cttgagcgtc gattttgtg atgctcgtca gggggggcgga        60 gcctatggaa aaacgccagc aacgcggcct ttttacggtt cctggccttt tgctggcctt       120
ttgctcacat gttctttcct gcgttatccc ctgattctgt ggataaccgt attaccgcct       180
ttgagtgagc tgataccgct cgccgcagcc gaacgaccga gcgcagcgag tcagtgagcg       240
aggaagcggt cgctgaggct tgacatgatt ggtgcgtatg tttgtatgaa gctacaggac       300
```

```
tgatttggcg ggctatgagg gcggggaag ctctggaagg gccgcgatgg ggcgcgcggc      360
gtccagaagg cgccatacgg cccgctggcg gcacccatcc ggtataaaag cccgcgaccc      420
cgaacggtga cctccacttt cagcgacaaa cgagcactta tacatacgcg actattctgc      480
cgctatacat aaccactcag ctagcttaag atcccatcaa gcttgcatgc cgggcgcgcc      540
agaaggagcg cagccaaacc aggatgatgt tgatggggt atttgagcac ttgcaaccct      600
tatccggaag cccctggcc cacaaaggct aggcgccaat gcaagcagtt cgcatgcagc      660
ccctggagcg gtgccctcct gataaaccgg ccagggggcc tatgttcttt acttttttac      720
aagagaagtc actcaacatc ttaaaatggc caggtgagtc gacgagcaag cccggcggat      780
caggcagcgt gcttgcagat ttgacttgca acgcccgcat tgtgtcgacg aaggcttttg      840
gctcctctgt cgctgtctca gcagcatct aaccctgcgt cgccgtttcc atttgcagga      900
gattcgaggt accatactcc accttcgccg cccgcgttgg cgctaagccc gctgtacgcg      960
gtgctcgccc cgccagccgc atgagctgca tggcctacaa ggtcaccctg aagacccctt     1020
cgggcgacaa gaccattgag tgccccgctg acacctacat cctggacgct gctgaggagg     1080
ccggcctgga cctgccctac tcttgccgcg ctggtgcttg ctccagctgc gccggcaagg     1140
tcgctgccgg caccgtggac cagtcggacc agtccttcct ggacgatgcc cagatgggca     1200
acggcttcgt gctgacctgc gtggcctacc ccacctcgga ctgcaccatc cagacccacc     1260
aggaggaggc cctgtacacc ggtggtggtg catcttggag ccacccgcag ttcgagaaga     1320
gcggcggtgg tgctagcgcc gctcctgctg ctgaggctcc tctgagccac gtgcagcagg     1380
ccctggctga gctggccaag cccaaggacg accccacccg caagcacgtg tgcgtccagg     1440
tcgcccctgc tgtgcgcgtg gccattgctg agactctggg cctggctccc ggcgctacca     1500
cccctaagca gctggctgag ggcctgcgcc gcctgggctt tgatgaggtg ttcgacaccc     1560
tgttcggcgc cgacctgacc atcatggagg agggctctga gctgctgcac cgcctgaccg     1620
agcacctgga ggctcaccct cacagcgacg agccctgcc catgttcacc agctgctgcc     1680
ccggctggat cgccatgctg gagaagtcct accccgacct gatcccctac gtgtccagct     1740
gcaagagccc ccagatgatg ctggccgcta tggtcaagag ctacctggcc gagaagaagg     1800
gcattgcccc caaggacatg gtcatggtgt ccatcatgcc ctgcacgcgc aagcagagcg     1860
aggccgaccg cgactggttc tgcgtcgacg cagaccctac cctgcgccag ctggaccacg     1920
tgatcaccac cgtcgagctg ggcaacatct tcaaggagcg cggcatcaac ctggcggagc     1980
tgcctgaggg cgagtgggac aaccctatgg gcgtgggttc tggcgctggc gtgctgttcg     2040
gcaccactgg cggtgtcatg gaggccgccc tgcgcaccgc ttacgagctg ttcaccggca     2100
cccctctgcc ccgcctgtct ctgtctgagg tccgcggcat ggacggcatc aaggagacta     2160
acatcacgat ggtgcccgct cccggcagca agttcgagga gctcctgaag caccgcgctg     2220
ccgctcgcgc tgaggctgct gctcacggta ctcccggtcc tctggcttgg gacggcggtg     2280
ctggcttcac tagcgaggac ggtcgcggcg gtattaccct gcgcgtggca gtggctaacg     2340
gcctgggcaa cgccaagaag ctgatcacca agatgcaggc cggcgaggcg aagtacgact     2400
tcgtcgagat catggcctgc cccgctggct gcgtcggtgg tggtggccag cctcgcagca     2460
ccgacaaggc catcacccag aagcgccagg ccgcgctgta caacctggac gagaagtcca     2520
ccctgcgccg cagccacgag aaccccagca tccgcgagct gtacgacacc tacctgggcg     2580
agcccctggg ccacaaggct cacgagctgc tccacaccca ctacgtggca ggcggcgtcg     2640
aggagaagga cgagaagaag taggaattcc cgctccgtgt aaatggaggc gctcgttgat     2700
```

```
ctgagccttg cccctgacg aacggcggtg gatggaagat actgctctca agtgctgaag    2760
cggtagctta gctccccgtt tcgtgctgat cagtcttttt caacacgtaa aaagcggagg    2820
agttttgcaa ttttgttggt tgtaacgatc ctccgttgat tttggcctct ttctccattg    2880
gcgggctggg cgtatttgaa gcgagatc                                       2908
```

<210> SEQ ID NO 7
<211> LENGTH: 3456
<212> TYPE: DNA
<213> ORGANISM: Chlamydomonas reinhardtii

<400> SEQUENCE: 7

```
atggcgcaca gcctcagcgc acacagccgt caggctggtg acagaaagct tggcgcgggc     60
gcggcctcgt cgcgcccgag ctgtccctcg cgccgcattg tgcgcgtcgc cgcgcatgcg    120
agcgcctcca aggccacgcc cgacgtcccg gtcgatgacc tgcctcccgc tcatgcccgc    180
gctgccgtcg cggccgccaa ccgccgcgct cgtgccatgg cttcggctga ggccgccgcg    240
gagaccctgg gtgacttcct ggggctcggc aagggcgggc tttcgcccgg gccaccgcc     300 aacctggaca gggaacaggt actgggtgtg ctggaggcgg tgtggcgccg cggcgacctc    360
aacctggagc gcgcgctgta cagccacgcc aacgccgtca ccaacaagta ctgcggcggc    420
ggtgtgtatt accgcggcct ggtggagttc tccaacatct gccagaacga ctgcagctac    480
tgcggcatcc gcaacaacca gaaggaggtg tggcgctaca ccatgccggt ggaggaggtg    540
gtggaggtgg ccaagtgggc gctggagaac ggcatccgca acatcatgct gcagggcggc    600
gagctcaaaa cggagcagcg cctggcgtat ctggaggcgt cgtgcgcgc catccgcgag    660 gagaccaccc agctggacct ggagatgcgc gcgcgcgccg cctccaccac cacagctgag    720
gccgccgcct ccgcgcaggc ggacgcagag gccaagaggg gcgagccgga gctaggcgtg    780
gtggtgtcgc tgagtgtggg cgagctgccc atggagcagt acgagcggct gttcagggct    840
ggcgcgcggc gctacctgat ccgcatcgag acctccaacc ccgacctgta cgctgcgctg    900
caccccgagc ccatgagctg gcacgcgcgc gtggagtgcc tgcgcaacct caagaaggcc    960
ggctacatgc tgggcactgg cgtgatggtg gggctgccgg ccagacgct gcacgacctg   1020 gcgggcgacg tcatgttctt ccgcgacatc aaggccgaca tgatcggcat gggccccttc   1080
atcacgcagc cggcacgcc cgccaccgac aagtggacgg cgctataccc caacgccaac   1140
aagaacagcc acatgaagtc catgttcgac ctcacaaccg ccatgaacgc gctggtgcga   1200
atcaccatgg gcaacgtcaa catcagcgcc accaccgcgc tgcaggccat catccccacc   1260
ggccgcgaga ttgcgctgga gcgcggcgcc aatgtggtga tgcccatcct cacgcccacc   1320
cagtaccgcg agtcctacca gctgtacgag ggcaagccct gcatcaccga caccgccgtg   1380
cagtgccggc gctgcctgga catgcgcctg cacagcgtgg gcaagacctc cgccgcgggc   1440
gtgtggggcg accccgcctc cttcctgcac cccatcgtgg gcgtgccgt gccgcacgac   1500 ctgtccagcc ccgcgctggc cgccgccgcc tccgccgact ccacgaggt gggagccggc   1560 ccctggaacc ccatccgact ggagcgattg gtggaggtgc cggaccgcta ccccgacccc   1620
gataaccatg gccgcaagaa ggccggggcc ggcaagggcg gcaaggccca cgactcccac   1680
gacgacggcg accacgacga ccaccaccac caccacggcg ccgcgcccgc gggcgccgcg   1740
gctgccaagg gcaccggtgc cgcgcgcgatc ggtggcggcg ccggcgcttc gcgccagcgc   1800
gtggcaggcg ctgcgcgcgc ctctgcgcgg ctgtgtgcgg gcgcgcgccg cgctgggcgc   1860
gtggtggcgt cgccgctgcg gccggcggcg gcgtgccgcg gcgtggcagt gaaggcggcg   1920
```

-continued

| | |
|---|---|
| gcggcggcgg ctggcgagga tgcgggcgcg ggcaccagtg gcgtgggcag caacattgtg | 1980 |
| accagccccg gcatcgccag caccaccgct cacggtgtgc cgcgaatcaa catcggcgtg | 2040 |
| ttcggagtca tgaatgcggg caagtcgacg ctggtgaacg ctctggcgca gcaggaggcg | 2100 |
| tgcatcgtgg actccacgcc cggcaccacc gccgacgtca agacggtgct tctagagttg | 2160 |
| cacgcgctgg gcccggccaa gctgctggac actgcggggc tggacgaggt gggcgggctg | 2220 |
| ggcgacaaga gcggcgcaa ggcgctcaac accctcaagg agtgcgacgt ggcggtgctg | 2280 |
| gtcgtggaca cggacacggc ggcggcggcc atcaagtccg gccgcctggc ggaggcgctg | 2340 |
| gagtgggagt ccaaggtgat ggagcaggcg cacaagtaca acgtcagccc agtgctgctg | 2400 |
| ctcaacgtca agagccgggg gctaccggag gcgcaggcag cgtccatgct ggaggcggtg | 2460 |
| gcaggcatgc tggacccaag caagcagatt ccccgcatgt cgctggacct ggccagcacg | 2520 |
| ccgctgcacg agcgctccac catcacctcg gccttcgtca aggagggcgc cgtgcgctcc | 2580 |
| agccgctacg gcgcgccgct gccaggctgc ctgccgcgct ggagcctggg ccgcaacgcc | 2640 |
| aggctgctca tggtcatccc catggacgcc gagaccccg gcggccgcct gctgcgcccca | 2700 |
| caggcgcagg tcatggagga ggccatccgg cactgggcca cggtactgag cgtgcgcctg | 2760 |
| gacctggacg cggcgcgcgg caagctagga cccgaggcgt gcgagatgga cgccagcgc | 2820 |
| tttgacggcg tcatcgcaat gatggagagg aacgacggcc ccacgctggt ggtcaccgac | 2880 |
| tcgcaggcta tcgacgtggt gcaccccctgg actctggacc gctcctccgg gcggccgctg | 2940 |
| gtgcccatca ccaccttctc catcgccatg gcctaccagc agaacggcgg gcggctggac | 3000 |
| cccttttgtgg aggggctgga ggcgctagag acgctgcagg acggcgaccg cgtgctgatc | 3060 |
| tcggaggcgt gcaaccacaa ccgcatcacc tccgcctgca acgacatcgg catggtgcag | 3120 |
| atccccaaca gctggaggc ggcgctgggc ggcaagaagc tgcagatcga gcacgccttc | 3180 |
| ggccgcgagt tcccggagct tgagtcgggc ggtatggacg tctgaagct ggccattcac | 3240 |
| tgcggcggct gcatgattga cgcccagaag atgcagcagc gcatgaagga cctgcacgag | 3300 |
| gcaggcgtgc ccgtcaccaa ctacggcgtg ttcttctctt gggccgcctg gcccgacgcc | 3360 |
| ctgcgccgcg cgctggagcc ctggggtgtc gagccgcccg taggcactcc cgccacgccc | 3420 |
| gccgccgcgc cggctaccgc agccagcggc gtgtaa | 3456 |

<210> SEQ ID NO 8
<211> LENGTH: 1704
<212> TYPE: DNA
<213> ORGANISM: Chlamydomonas reinhardtii

<400> SEQUENCE: 8

| | |
|---|---|
| atgtcggtac ctctgcagtg caatgcgggg cgcctgctcg cgggccagcg gccctgcggc | 60 |
| gtccgcgccc ggctgaatcg tcgcgtttgt gtcccagtca ccgcgcacgg caaggcctct | 120 |
| gcgacccgcg aatatgctgg tgacttcctt cccggcacta ccatttcaca cgcgtggagt | 180 |
| gtcgagcgtg agacgcacca caggtaccgc aaccccgccg agtggatcaa cgaggccgct | 240 |
| attcacaagg cgctggagac ctccaaggcg gacgcccagg acgccggacg ggtgcgcgag | 300 |
| atcctggcca aggccaagga aaaggccttc gtcaccgagc atgcgcccgt caacgccgag | 360 |
| tccaagtccg agttcgtgca aggcctgacg ctggaggagt gcgctacgct catcaacgtg | 420 |
| gactcgaaca acgtcgagct gatgaatgag atcttcgaca cggccctggc catcaaggag | 480 |
| cgcatctacg ggaaccgtgt ggtgctcttc gcgccgcttt acatcgccaa tcactgcatg | 540 |
| aacacctgca cctactgcgc cttccgctcc gccaacaagg gcatggagcg ctccatcctc | 600 |

```
accgacgacg acctacgcga ggaggtagcg gcgctgcagc gccagggcca ccgccgcatc    660
ctggcgctca ccggcgagca ccccaagtac acctttgaca acttcctgca cgccgtgaac    720
gtgatcgcat ctgtcaagac ggagccggag ggcagcatcc gccgcatcaa tgtggagatt    780
ccgcccctat cggtgtcgga catgcgccgc ctgaagaaca cggacagcgt gggcacgttc    840
gtgctgttcc aggagaccta ccaccgcgac accttcaagg tcatgcaccc ctccggccca    900
aagtccgact cgacttccg cgtgctgacg caggaccggg ccatgcgcgc cggccttgac     960
gacgtgggca tcggcgccct gttcggactg tacgactacc gctacgaggt gtgcgcgatg   1020
ttgatgcaca gcgagcacct ggagcgcgag tacaacgccg gccgcacac catcagcgtg    1080 cctcgcatgc gccctgccga cggctccgag ctgtccattg cgccgccgta cccggtcaat   1140
gacgctgact tcatgaaact ggtggcggtg ctgcgcatcg cggtgccgta caccggcatg   1200
atcctgtcca ccagggagtc gcccgagatg cgctctgcgc tgctcaagtg cggcatgagc   1260
cagatgagcg cgggcagccg cacggacgtg ggcgcctacc acaaggacca cacgctgtca   1320
accgaggcca acctgtccaa gctggcgggt cagttcacgc tgcaggacga cgccccacc    1380 aacgagatcg tcaagtggct gatggaggag ggctacgtgc ccagctggtg cacggcctgc   1440
taccgccagg gccgcaccgg cgaggacttc atgaacatct gcaaggccgg cgacatccac   1500
gacttctgcc accccaactc gctgctcacg ctccaggagt acctgatgga ctacgccgac   1560
cccgacctgc gcaagaaggg cgagcaggtg attgcgcgcg agatgggccc cgacgcctcg   1620
gagccgctgt cggcgcagag ccgcaagcga ctggagcgca agatgaagca ggtgctggag   1680
ggcgagcacg acgtgtacct gtaa                                          1704

<210> SEQ ID NO 9
<211> LENGTH: 1410
<212> TYPE: DNA
<213> ORGANISM: Chlamydomonas reinhardtii

<400> SEQUENCE: 9
gtcgctgctc acgccagcgc cagcaaggct actcctgatg tgcccgtgga cgacctgcct     60
cctgctcacg cgcgtgctgc cgtggctgct gctaaccgcc gcgctcgcgc tatggcttcc    120
gctgaggctg ctgccgagac tctgggcgac ttcctgggcc tgggcaaggg tggcctgtct    180
cccggcgcta ctgctaacct ggaccgcgag caggtcctgg gcgtgctgga ggctgtgtgg    240
cgccggggcg acctgaacct ggagcgcgct ctgtacagcc acgccaacgc cgtgaccaac    300
aagtattgcg gcggtggcgt gtactaccgg ggcctggtcg agttcagcaa catctgccag    360
aacgactgct cctactgcgg catccgcaac aaccagaagg aggtctggcg ctacaccatg    420
ccggtcgagg aggtggtcga ggtcgccaag tgggccctgg agaacggcat ccggaacatc    480
atgctccagg gcggcgagct caagaccgag cagcgcctgg cttacctgga ggcctgcgtc    540
cgcgccatcc gcgaggagac tactcagctg gacctggaga tgcgcgcacg cgctgcttcg    600
accaccactg ctgaggccgc tgcttccgcc caggccgacg ctgaggctaa gcgcggcgag    660
cctgagctgg gtgtcgtggt gtctctgagc gtcggcgagc tgccgatgga gcagtacgag    720
cgcctgtttc gcgctggcgc tcgccgctac ctgatccgca tcgagactag caaccccgac    780
ctgtacgccg ccctgcaccc cgagcctatg tcttggcatg ctcgcgtcga gtgcctgcgc    840
aacctgaaga aggccggcta catgctgggc accggcgtga tggtcggcct gcctggccag    900
actctgcacg acctggccgg cgacgtgatg ttcttccgcg acatcaaggc cgacatgatc    960
ggcatgggcc ccttcatcac ccagcccggc accccgcta ccgacaagtg gaccgctctg   1020
```

```
tacccccaacg cgaacaagaa cagccacatg aagtccatgt tcgacctgac caccgccatg    1080
aacgccctcg tgcgcatcac gatgggcaac gtgaacatca gcgccaccac cgccctccag    1140
gccatcattc ccactggccg cgagatcgct ctggagcgcg gtgccaacgt ggtcatgccc    1200
atcctgaccc ccacccagta ccgcgagagc taccagctgt acgagggcaa gccctgcatc    1260
accgacaccg ctgtgcagtg ccgccgctgc ctggacatgc gcctgcactc tgtgggcaag    1320
accagcgccg cgggcgtgtg gggcgaccct gcttccttcc tgcacccccat tgtgggcgtg    1380 cccgtgcccc acgacctgag cagccctgct                                     1410
```

<210> SEQ ID NO 10
<211> LENGTH: 1548
<212> TYPE: DNA
<213> ORGANISM: Chlamydomonas reinhardtii

<400> SEQUENCE: 10

```
gtgaaggctg ctgctgcggc tgctggcgag gacgcaggcg ctggtacttc tggcgtgggc      60
agcaacatcg tgaccagccc cggcattgcc agcaccactg ctcacggcgt gccccgcatc     120
aacatcggcg tgttcggcgt gatgaacgcc ggcaagtcga ccctggtcaa cgccctggct     180
cagcaggagg cctgcatcgt cgatagcacc cctggcacca ccgccgatgt caagaccgtg     240
ctgctggagc tgcacgccct gggccctgcc aagctgctgg acactgctgg cctggacgag     300
gtcggcggcc tgggcgacaa gaagcgccga aaggccctga cacccctgaa ggagtgcgac     360
gtcgccgtcc tggtggtgga caccgacacc gccgctgccg ccattaagtc tggccgcctg     420
gctgaggccc tggagtggga gagcaaggtc atggagcagg cccacaagta caacgtgtcc     480
ccggtcctgc tgctgaacgt gaagtctcgc ggcctgcccg aggcccaggc tgcttctatg     540
ctggaggccg tggctggcat gctggacccc agcaagcaga tcccccgcat gagcctggac     600
ctggccagca ctcctctgca cgagcgcagc accatcacca gcgccttcgt gaaggagggc     660
gctgtccgct ctagccgcta cggcgctcct ctgcctggtt gcctgcctcg ctggtccctg     720
ggtcgcaacg ctcgcctgct gatggtcatc ccgatggacg ccgagactcc cggtggtcgc     780
ctgctgcggc ctcaggctca ggtcatggag gaggctatcc gccactgggc caccgtgctg     840
tctgtgcggc tggacctgga cgctgctcgc ggcaagctgg gtcccgaggc ttgcgagatg     900
gagcgccagc gcttcgacgg cgtgatcgcc atgatggagc gcaacgacgg ccccacccctg    960 gtcgtgaccg acagccaggc cattgatgtg gtgcaccccct ggaccctgga ccgctcttct   1020
gggcggccgc tggtgcccat caccaccttc tcgatcgcta tggcctacca gcagaacggc   1080
ggtcgcctgg acccctttcgt cgagggcctg gaggcgctgg agactctcca ggacggcgac   1140
cgcgtgctga tcagcgaggc ctgcaaccac aaccgcatca cctccgcctg caacgacatc   1200
ggcatggtgc agatccccaa caagctggag gctgccctcg gcggcaagaa gctccagatc   1260
gagcacgcct tcggccgcga gttccctgag ctggagtctg gcggcatgga cggcctgaag   1320
ctggccattc actgcggcgg ctgcatgatc gacgcccaga gatgcagca gcgcatgaag   1380 gacctgcacg aggccggcgt gcccgtgacc aactacggcg tgttcttcag ctgggccgcg   1440
tggcctgatg ctctgcgccg cgctctggag ccttggggtg tcgagcctcc tgtgggcacc   1500
cctgctactc cagccgctgc tcctgctacc gccgccagcg gtgtctaa               1548
```

<210> SEQ ID NO 11
<211> LENGTH: 1605
<212> TYPE: DNA
<213> ORGANISM: Chlamydomonas reinhardtii

```
<400> SEQUENCE: 11
accgctcacg gcaaggcttc cgcaactcgc gagtacgccg gcgacttcct gcccggcacc      60
accatctctc atgcttggag cgtcgagcgc gagactcacc accgctaccg caaccccgcc     120
gagtggatca acgaggccgc catccacaag gccctggaga ctagcaaggc cgacgctcag     180
gacgctggcc gcgtgcgcga gatcctggcc aaggccaagg agaaggcctt tgtcaccgag     240
cacgcccccg tgaacgccga gagcaagagc gagttcgtgc agggcctgac cctggaggag     300
tgcgccaccc tgatcaacgt cgacagcaac aacgtcgagc tgatgaacga gattttcgac     360
accgccctgg ccatcaagga gcgcatctac ggcaaccgcg tggtgctgtt cgccccctg     420 tacattgcca accactgcat gaacacgtgc acctactgcg ccttccgcag cgccaacaag     480
ggcatggagc gcagcatcct gaccgacgac gacctgcgcg aggaggtggc agctctccag     540
cgccagggtc accgccgcat tctggctctg accggcgagc accccaagta caccttcgac     600
aactttctgc acgccgtgaa cgtgatcgcc tctgtcaaga ccgagcccga gggcagcatc     660
cgccgcatca acgtcgagat ccccccccctg tccgtgtccg acatgcgccg cctgaagaac     720
accgactccg tgggcacctt cgtgctgttt caggagactt accaccggga caccttcaag     780
gtcatgcacc ccagcggccc caagagcgac ttcgacttcc gcgtgctgac ccaggaccgc     840
gctatgcgcg ctggcctgga cgacgtgggc attggcgctc tgttcggcct gtacgactac     900
cgctacgagg tctgcgccat gctgatgcac agcgagcacc tggagcgcga gtacaacgct     960 ggccccccaca ccatctctgt gccccgcatg cgccctgctg atggcagcga gctgagcatt    1020 gctccccct accctgttaa cgacgccgac ttcatgaagc tggtggccgt gctgcgcatt    1080
gccgtgccct acaccggcat gatcctgagc accgcgaga gccccgagat gcgcagcgct    1140
ctgctgaagt gcggcatgag ccagatgagc gccggctctc gcaccgacgt gggcgcctac    1200
cacaaggacc acacccctgag caccgaggcc aacctgagca agctagcggg ccagtttacg    1260
ctccaggacg agcgccccac caacgagatc gtgaagtggc tgatggagga gggttatgtc    1320
cccagctggt gcaccgcatg ctaccgccag ggtcgcaccg gcgaggactt tatgaacatc    1380
tgcaaggccg gcgacatcca cgacttttgc caccccaaca gcctgctgac tctccaggag    1440
tacctgatgg actacgccga ccccgacctg cgcaagaagg gcgagcaggt catcgctcgc    1500
gagatgggcc ctgatgcttc cgagcctctg agcgcacaga gccgcaagcg cctggagcgc    1560
aagatgaagc aggtcctgga gggcgagcac gacgtgtacc tgtag                     1605

<210> SEQ ID NO 12
<211> LENGTH: 3066
<212> TYPE: DNA
<213> ORGANISM: Chlamydomonas reinhardtii

<400> SEQUENCE: 12
gcagaggttg ggaatcgctt tgaaaatcca gcaatcgggt ctcagctgtc caggccgca      60 cgcgccttgg acaaggcact tcagtaacgt actccaagcc ctctatctgc atgcccacaa     120
agcgcaggaa tgccgaccat cgtgccagac tgtgccgcgc ccgaaccgaa atccgtcact     180
ccccttggtt cacatggtgg catggtcccc cctgttcgcc caaagcctgg ttcagcgccc     240
agtggcaaac ggctttggct cagctccttg gtattgctgg tttctagcaa tctcgtccgt     300
tcctctgttg ccaatgtagc aggtgcaaac agtcgaatac ggttttactc aggggcaatc     360
tcaactaaca gaggccctgg gcctgttgcc tggaacctat gaagacgata atgccacggc     420
gactttcgag cctgagggaa gtttgcacct gtaccgcatt gtgcaaggtt acggtacatg     480
```

```
ataggggagg tgcgacgcgg taaggcttgg cgcagcttgg cgcgtctgcc ttgcatgcat    540
gtccgaaaca cgccacgtcg cgccacgaaa agcggtaaaa ggacctgaca tggtcctcca    600
gggtgttacc acttccattt cgctcagctg ggatggtgct cgtaggtgca ccagcgttga    660
ttatttcagg caggaagcgg ctgcgaagcc cgcctttcac tgaagactgg gatgagcgca    720
cctgtacctg ccagtatcgt accggcgcgc taccgatgcg tgtagtagag cttgctgcca    780
tacagtaact ctggtactcc cagccaccgg gcgtagcgag cagactcaat aagtatgatg    840
ggttcttatt gcagccgctg ttacagttta cagcgcaagg gaacacgccc ctcattcaca    900
gaactaactc aacctactcc atccatatgc aggcaagtaa tagtccaacc agtcttgcag    960
cggcgctagg ccgtctcgcg ctttcgaccc atctgacctt atcgcgtgct ccctctctcg   1020
ttctgggtgc agaccgtgcg tgctcccgcc gcctccggcg ttgccacccg cgtggctggc   1080
cgccgcatgt gccgccccgt ggcggccctg caggcaccgg cggtgcacc gctcacggca    1140
aggcttccgc aactcgcgag tacgccggcg acttcctgcc cggcaccacc atctctcatg   1200
cttggagcgt cgagcgcgag actcaccacc gctaccgcaa ccccgccgag tggatcaacg   1260
aggccgccat ccacaaggcc ctggagacta gcaaggccga cgctcaggac gctggccgcg   1320
tgcgcgagat cctggccaag gccaaggaga aggcctttgt caccgagcac gccccgtga    1380
acgccgagag caagagcgag ttcgtgcagg gcctgaccct ggaggagtgc gccaccctga   1440
tcaacgtcga cagcaacaac gtcgagctga tgaacgagat tttcgacacc gccctggcca   1500
tcaaggagcg catctacggc aaccgcgtgg tgctgttcgc cccctgtac attgccaacc    1560
actgcatgaa cacgtgcacc tactgcgcct tccgcagcgc caacaagggc atggagcgca   1620
gcatcctgac cgacgacgac ctgcgcgagg aggtggcagc tctccagcgc cagggtcacc   1680
gccgcattct ggctctgacc ggcgagcacc ccaagtacac cttcgacaac tttctgcacg   1740
ccgtgaacgt gatcgcctct gtcaagaccg agcccgaggg cagcatccgc cgcatcaacg   1800
tcgagatccc ccccctgtcc gtgtccgaca tgcgccgcct gaagaacacc gactccgtgg   1860
gcaccttcgt gctgtttcag gagacttacc accgggacac cttcaaggtc atgcacccca   1920
gcggccccaa gagcgacttc gacttccgcg tgctgaccca ggaccgcgct atgcgcgctg   1980
gcctggacga cgtgggcatt ggcgctctgt tcggcctgta cgactaccgc tacgaggtct   2040
gcgccatgct gatgcacagc gagcacctgg agcgcgagta caacgctggc ccccacacca   2100
tctctgtgcc ccgcatgcgc cctgctgatg gcagcgagct gagcattgct cccccctacc   2160
ctgttaacga cgccgacttc atgaagctgg tggccgtgct gcgcattgcc gtgccctaca   2220
ccggcatgat cctgagcacc cgcgagagcc ccgagatgcg cagcgctctg ctgaagtgcg   2280
gcatgagcca gatgagcgcc ggctctcgca ccgacgtggg cgcctaccac aaggaccaca   2340
ccctgagcac cgaggccaac ctgagcaagc tagcgggcca gtttacgctc caggacgagc   2400
gccccaccaa cgagatcgtg aagtggctga tggaggaggg ttatgtcccc agctggtgca   2460
ccgcatgcta ccgccagggt cgcaccgcg aggactttat gaacatctgc aaggccggcg    2520
acatccacga cttttgccac cccaacagcc tgctgactct ccaggagtac ctgatggact   2580
acgccgaccc cgacctgcgc aagaagggcg agcaggtcat cgctcgcgag atgggccctg   2640
atgcttccga gcctctgagc gcacagagcc gcaagcgcct ggagcgcaag atgaagcagg   2700
tcctggaggg cgagcacgac gtgtacctgt aggaattctg gaagtacgtt gatgttgtta   2760
tttcaactgg gtcaccgtag cttgctcgtg ccccagttgt ggatgcgagt tatacgtcat   2820
tgcgtaacat gttcatgata gactgcatta ggtaggcgtc gtgtgtgagc acatacagaa   2880
```

```
gtcatcacgc aaatggacac gttccggcga acccgagggg aaaggcttgg gccagtacat    2940
tatttcaaca ctaaaatatg taacataatg gaacttgagc acggtccggg agcgcaggct    3000
gggcttgggg gtcgcggctc gaaggagagg ggcgacgttg gggcaggtcg gggcttcaac    3060
cgggtt                                                               3066

<210> SEQ ID NO 13
<211> LENGTH: 4875
<212> TYPE: DNA
<213> ORGANISM: Chlamydomonas reinhardtii

<400> SEQUENCE: 13
actagagcag aggttgggaa tcgctttgaa aatccagcaa tcgggtctca gctgtctcag      60
gccgcacgcg ccttggacaa ggcacttcag taacgtactc caagccctct atctgcatgc     120
ccacaaagcg caggaatgcc gaccatcgtg ccagactgtg ccgcgcccga accgaaatcc     180
gtcactcccc ttggttcaca tggtggcatg gtcccccctg ttcgcccaaa gcctggttca     240
gcgcccagtg gcaaacggct ttggctcagc tccttggtat tgctggtttc tagcaatctc     300
gtccgttcct ctgttgccaa tgtagcaggt gcaaacagtc gaatacggtt ttactcaggg     360
gcaatctcaa ctaacagagg ccctgggcct gttgcctgga acctatgaag acgataatgc     420
cacggcgact ttcgagcctg agggaagttt gcacctgtac cgcattgtgc aaggttacgg     480
tacatgatag ggggagtgcg acgcggtaag gcttggcgca gcttggcgcg tctgccttgc     540
atgcatgtcc gaaacacgcc acgtcgcgcc acgaaaagcg gtaaaaggac ctgacatggt     600
cctccagggt gttaccactt ccatttcgct cagctgggat ggtgctcgta ggtgcaccag     660
cgttgattat ttcaggcagg aagcggctgc gaagcccgcc tttcactgaa gactgggatg     720
agcgcacctg tacctgccag tatcgtaccg gcgcgctacc gatgcgtgta gtagagcttg     780
ctgccataca gtaactctgg tactcccagc caccgggcgt agcgagcaga ctcaataagt     840
atgatgggtt cttattgcag ccgctgttac agtttacagc gcaagggaac acgcccctca     900
ttcacagaac taactcaacc tactccatcc atatgcaggc aagtaatagt ccaaccagtc     960
ttgcagcggc gctaggccgt ctcgcgcttt cgacccatct gaccttatcg cgtgctccct    1020
ctctcgttct gggtgcagac cgtgcgtgct cccgccgcct ccggcgttgc cacccgcgtg    1080
gctggccgcc gcatgtgccg ccccgtggcg gccctgcagg gtggtactca ccaccaccac    1140
caccacggct ctggcggcgg ttctggtggt ggttctggcg gtgtcgctgc tcacgccagc    1200
gccagcaagg ctactcctga tgtgcccgtg gacgacctgc ctcctgctca cgcgcgtgct    1260
gccgtggctg ctgctaaccg ccgcgctcgc gctatggctt ccgctgaggc tgctgccgag    1320
actctgggcg acttcctggg cctgggcaag ggtggcctgt ctcccggcgc tactgctaac    1380
ctggaccgcg agcaggtcct gggcgtgctg gaggctgtgt ggcgccgggg cgacctgaac    1440
ctggagcgcg ctctgtacag ccacgccaac gccgtgacca acaagtattg cggcggtggc    1500
gtgtactacc ggggcctggt cgagttcagc aacatctgcc agaacgactg ctcctactgc    1560
ggcatccgca caaccagaa ggaggtctgg cgctacacca tgccggtcga ggaggtggtc    1620
gaggtcgcca gtgggccct ggagaacggc atcggaaca tcatgctcca gggcggcgag    1680
ctcaagaccg agcagcgcct ggcttacctg gaggcctgcg tccgcgccat ccgcgaggag    1740
actactcagc tggacctgga gatgcgcgca cgcgctgctt cgaccaccac tgctgaggcc    1800
gctgcttccg cccaggccga cgctgaggct aagcgcggcg agcctgagct gggtgtcgtg    1860
gtgtctctga gcgtcggcga gctgccgatg gagcagtacg agcgcctgtt tcgcgctggc    1920
```

```
gctcgccgct acctgatccg catcgagact agcaaccccg acctgtacgc cgccctgcac      1980
cccgagccta tgtcttggca tgctcgcgtc gagtgcctgc gcaacctgaa gaaggccggc      2040
tacatgctgg gcaccggcgt gatggtcggc ctgcctggcc agactctgca cgacctggcc      2100
ggcgacgtga tgttcttccg cgacatcaag gccgacatga tcggcatggg ccccttcatc      2160
acccagcccg gcaccccgc taccgacaag tggaccgctc tgtaccccaa cgcgaacaag       2220
aacagccaca tgaagtccat gttcgacctg accaccgcca tgaacgccct cgtgcgcatc      2280
acgatgggca acgtgaacat cagcgccacc accgccctcc aggccatcat tcccactggc      2340
cgcgagatcg ctctggagcg cggtgccaac gtggtcatgc ccatcctgac ccccaccccag     2400 taccgcgaga gctaccagct gtacgagggc aagccctgca tcaccgacac cgctgtgcag     2460
tgccgccgct gcctggacat cgcctgcac  tctgtgggca agaccagcgc cgcgggcgtg    2520
tggggcgacc ctgcttcctt cctgcacccc attgtgggcg tgcccgtgcc ccacgacctg    2580
agcagccctg ctctcgctgc tgctgccagc gccgactttc acgaggtcgg cgctggtccc   2640
tggaacccca ttcgcctgga gcggctggtc gaggtgcccg accgctaccc tgaccctgac   2700
aaccatggcc gcaagaaggc tggcgctggc aagggcggca aggcccacga ctctcacgac   2760
gacggcgacc acgacgacca ccaccaccac cacggtgctg ctcccgctgg tgctgctgcc   2820
ggcaagggta ctggcgctgc tgctattggc ggcggtgctg gtgcttctcg ccagcgcgtg   2880
gcaggcgcag ctgctgcttc tgctcgcctg tgcgctggtg ctcgccgcgc tggtcgcgtg    2940
gtggcttctc ctctgcgccc tgctgctgct tgccagggcg tggccgtgaa ggctgctgct   3000
gcggctgctg gcgaggacgc aggcgctggt acttctggcg tgggcagcaa catcgtgacc   3060
agccccggca ttgccagcac cactgctcac ggcgtgcccc gcatcaacat cggcgtgttc   3120
ggcgtgatga acgccggcaa gtcgaccctg gtcaacgccc tggctcagca ggaggcctgc   3180
atcgtcgata gcacccctgg caccaccgcc gatgtcaaga ccgtgctgct ggagctgcac   3240
gccctgggcc ctgccaagct gctggacact gctggcctgg acgaggtcgg cggcctgggc   3300
gacaagaagc gccgcaaggc cctgaacacc ctgaaggagt gcgacgtcgc cgtcctggtg   3360
gtggacaccg acaccgccgc tgccgccatt aagtctggcc gcctggctga ggccctggag   3420
tgggagagca aggtcatgga gcaggcccac aagtacaacg tgtccccggt cctgctgctg   3480
aacgtgaagt ctcgcggcct gcccgaggcc caggctgctt ctatgctgga ggccgtggct   3540
ggcatgctgg accccagcaa gcagatcccc cgcatgagcc tggacctggc cagcactcct   3600
ctgcacgagc gcagcaccat caccagcgcc ttcgtgaagg agggcgctgt ccgctctagc   3660
cgctacggcg ctcctctgcc tggttgcctg cctcgctggt ccctgggtcg caacgctcgc   3720
ctgctgatgg tcatcccgat ggacgccgag actcccggtg gtcgcctgct gcggcctcag   3780
gctcaggtca tggaggaggc tatccgccac tgggccaccg tgctgtctgt gcggctggac   3840
ctggacgctg ctcgcggcaa gctgggtccc gaggcttgcg agatgagcg ccagcgcttc    3900 gacggcgtga tcgccatgat ggagcgcaac gacggcccca ccctggtcgt gaccgacagc   3960
caggccattg atgtggtgca ccccctggacc ctggaccgct cttctgggcg gccgctggtg   4020
cccatcacca ccttctcgat cgctatggcc taccagcaga acggcggtcg cctggacccct   4080 ttcgtcgagg gcctggaggc gctggagact ctccaggacg gcgaccgcgt gctgatcagc   4140
gaggcctgca accacaaccg catcacctcc gcctgcaacg acatcggcat ggtgcagatc   4200
cccaacaagt ggaggctgc cctcggcggc aagaagctcc agatcgagca cgccttcggc    4260
cgcgagttcc ctgagctgga gtctggcggc atggacggcc tgaagctggc cattcactgc   4320
```

```
ggcggctgca tgatcgacgc ccagaagatg cagcagcgca tgaaggacct gcacgaggcc    4380
ggcgtgcccg tgaccaacta cggcgtgttc ttcagctggg ccgcgtggcc tgatgctctg    4440
cgccgcgctc tggagccttg ggtgtcgag cctcctgtgg gcaccctgc tactccagcc     4500 gctgctcctg ctaccgccgc cagcggtgtc taagaattct ggaagtacgt tgatgttgtt    4560
atttcaactg ggtcaccgta gcttgctcgt gccccagttg tggatgcgag ttatacgtca    4620
ttgcgtaaca tgttcatgat agactgcatt aggtaggcgt cgtgtgtgag cacatacaga    4680
agtcatcacg caaatggaca cgttccggcg aacccgaggg gaaaggcttg ggccagtaca    4740
ttatttcaac actaaaatat gtaacataat ggaacttgag cacggtccgg gagcgcaggc    4800
tgggcttggg ggtcgcggct cgaaggagag gggcgacgtt ggggcaggtc ggggcttcaa    4860
ccgggtttca ctaga                                                    4875
```

<210> SEQ ID NO 14
<211> LENGTH: 470
<212> TYPE: PRT
<213> ORGANISM: Chlamydomonas reinhardtii

<400> SEQUENCE: 14

```
Val Ala Ala His Ala Ser Ala Ser Lys Ala Thr Pro Asp Val Pro Val
1               5                   10                  15

Asp Asp Leu Pro Pro Ala His Ala Arg Ala Ala Val Ala Ala Ala Asn
            20                  25                  30

Arg Arg Ala Arg Ala Met Ala Ser Ala Glu Ala Ala Glu Thr Leu
        35                  40                  45

Gly Asp Phe Leu Gly Leu Gly Lys Gly Gly Leu Ser Pro Gly Ala Thr
    50                  55                  60

Ala Asn Leu Asp Arg Glu Gln Val Leu Gly Val Leu Glu Ala Val Trp
65                  70                  75                  80

Arg Arg Gly Asp Leu Asn Leu Glu Arg Ala Leu Tyr Ser His Ala Asn
                85                  90                  95

Ala Val Thr Asn Lys Tyr Cys Gly Gly Val Tyr Tyr Arg Gly Leu
            100                 105                 110

Val Glu Phe Ser Asn Ile Cys Gln Asn Asp Cys Ser Tyr Cys Gly Ile
        115                 120                 125

Arg Asn Asn Gln Lys Glu Val Trp Arg Tyr Thr Met Pro Val Glu Glu
    130                 135                 140

Val Val Glu Val Ala Lys Trp Ala Leu Glu Asn Gly Ile Arg Asn Ile
145                 150                 155                 160

Met Leu Gln Gly Gly Glu Leu Lys Thr Glu Gln Arg Leu Ala Tyr Leu
                165                 170                 175

Glu Ala Cys Val Arg Ala Ile Arg Glu Thr Thr Gln Leu Asp Leu
            180                 185                 190

Glu Met Arg Ala Arg Ala Ala Ser Thr Thr Thr Ala Glu Ala Ala Ala
        195                 200                 205

Ser Ala Gln Ala Asp Ala Glu Ala Lys Arg Gly Glu Pro Glu Leu Gly
    210                 215                 220

Val Val Val Ser Leu Ser Val Gly Glu Leu Pro Met Glu Gln Tyr Glu
225                 230                 235                 240

Arg Leu Phe Arg Ala Gly Ala Arg Arg Tyr Leu Ile Arg Ile Glu Thr
                245                 250                 255

Ser Asn Pro Asp Leu Tyr Ala Ala Leu His Pro Glu Pro Met Ser Trp
            260                 265                 270
```

-continued

```
His Ala Arg Val Glu Cys Leu Arg Asn Leu Lys Lys Ala Gly Tyr Met
            275                 280                 285

Leu Gly Thr Gly Val Met Val Gly Leu Pro Gly Gln Thr Leu His Asp
290                 295                 300

Leu Ala Gly Asp Val Met Phe Phe Arg Asp Ile Lys Ala Asp Met Ile
305                 310                 315                 320

Gly Met Gly Pro Phe Ile Thr Gln Pro Gly Thr Pro Ala Thr Asp Lys
                325                 330                 335

Trp Thr Ala Leu Tyr Pro Asn Ala Asn Lys Asn Ser His Met Lys Ser
            340                 345                 350

Met Phe Asp Leu Thr Thr Ala Met Asn Ala Leu Val Arg Ile Thr Met
            355                 360                 365

Gly Asn Val Asn Ile Ser Ala Thr Thr Ala Leu Gln Ala Ile Ile Pro
370                 375                 380

Thr Gly Arg Glu Ile Ala Leu Glu Arg Gly Ala Asn Val Val Met Pro
385                 390                 395                 400

Ile Leu Thr Pro Thr Gln Tyr Arg Glu Ser Tyr Gln Leu Tyr Glu Gly
                405                 410                 415

Lys Pro Cys Ile Thr Asp Thr Ala Val Gln Cys Arg Arg Cys Leu Asp
                420                 425                 430

Met Arg Leu His Ser Val Gly Lys Thr Ser Ala Ala Gly Val Trp Gly
            435                 440                 445

Asp Pro Ala Ser Phe Leu His Pro Ile Val Gly Pro Val Pro His
            450                 455                 460

Asp Leu Ser Ser Pro Ala
465                 470

<210> SEQ ID NO 15
<211> LENGTH: 515
<212> TYPE: PRT
<213> ORGANISM: Chlamydomonas reinhardtii

<400> SEQUENCE: 15

Val Lys Ala Ala Ala Ala Ala Gly Glu Asp Ala Gly Ala Gly Thr
1               5                   10                  15

Ser Gly Val Gly Ser Asn Ile Val Thr Ser Pro Gly Ile Ala Ser Thr
                20                  25                  30

Thr Ala His Gly Val Pro Arg Ile Asn Ile Gly Val Phe Gly Val Met
            35                  40                  45

Asn Ala Gly Lys Ser Thr Leu Val Asn Ala Leu Ala Gln Gln Glu Ala
50                  55                  60

Cys Ile Val Asp Ser Thr Pro Gly Thr Thr Ala Asp Val Lys Thr Val
65                  70                  75                  80

Leu Leu Glu Leu His Ala Leu Gly Pro Ala Lys Leu Leu Asp Thr Ala
                85                  90                  95

Gly Leu Asp Glu Val Gly Gly Leu Gly Asp Lys Lys Arg Arg Lys Ala
                100                 105                 110

Leu Asn Thr Leu Lys Glu Cys Asp Val Ala Val Leu Val Val Asp Thr
            115                 120                 125

Asp Thr Ala Ala Ala Ile Lys Ser Gly Arg Leu Ala Glu Ala Leu
130                 135                 140

Glu Trp Glu Ser Lys Val Met Glu Gln Ala His Lys Tyr Asn Val Ser
145                 150                 155                 160

Pro Val Leu Leu Leu Asn Val Lys Ser Arg Gly Leu Pro Glu Ala Gln
                165                 170                 175
```

Ala Ala Ser Met Leu Glu Ala Val Ala Gly Met Leu Asp Pro Ser Lys
            180                 185                 190

Gln Ile Pro Arg Met Ser Leu Asp Leu Ala Ser Thr Pro Leu His Glu
        195                 200                 205

Arg Ser Thr Ile Thr Ser Ala Phe Val Lys Glu Gly Ala Val Arg Ser
    210                 215                 220

Ser Arg Tyr Gly Ala Pro Leu Pro Gly Cys Leu Pro Arg Trp Ser Leu
225                 230                 235                 240

Gly Arg Asn Ala Arg Leu Leu Met Val Ile Pro Met Asp Ala Glu Thr
                245                 250                 255

Pro Gly Gly Arg Leu Leu Arg Pro Gln Ala Gln Val Met Glu Glu Ala
            260                 265                 270

Ile Arg His Trp Ala Thr Val Leu Ser Val Arg Leu Asp Leu Asp Ala
        275                 280                 285

Ala Arg Gly Lys Leu Gly Pro Glu Ala Cys Glu Met Glu Arg Gln Arg
    290                 295                 300

Phe Asp Gly Val Ile Ala Met Met Glu Arg Asn Asp Gly Pro Thr Leu
305                 310                 315                 320

Val Val Thr Asp Ser Gln Ala Ile Asp Val Val His Pro Trp Thr Leu
                325                 330                 335

Asp Arg Ser Ser Gly Arg Pro Leu Val Pro Ile Thr Thr Phe Ser Ile
            340                 345                 350

Ala Met Ala Tyr Gln Gln Asn Gly Gly Arg Leu Asp Pro Phe Val Glu
        355                 360                 365

Gly Leu Glu Ala Leu Glu Thr Leu Gln Asp Gly Asp Arg Val Leu Ile
    370                 375                 380

Ser Glu Ala Cys Asn His Asn Arg Ile Thr Ser Ala Cys Asn Asp Ile
385                 390                 395                 400

Gly Met Val Gln Ile Pro Asn Lys Leu Glu Ala Ala Leu Gly Gly Lys
                405                 410                 415

Lys Leu Gln Ile Glu His Ala Phe Gly Arg Glu Phe Pro Glu Leu Glu
            420                 425                 430

Ser Gly Gly Met Asp Gly Leu Lys Leu Ala Ile His Cys Gly Gly Cys
        435                 440                 445

Met Ile Asp Ala Gln Lys Met Gln Gln Arg Met Lys Asp Leu His Glu
    450                 455                 460

Ala Gly Val Pro Val Thr Asn Tyr Gly Val Phe Ser Trp Ala Ala
465                 470                 475                 480

Trp Pro Asp Ala Leu Arg Arg Ala Leu Glu Pro Trp Gly Val Glu Pro
                485                 490                 495

Pro Val Gly Thr Pro Ala Thr Pro Ala Ala Pro Ala Thr Ala Ala
            500                 505                 510

Ser Gly Val
        515

<210> SEQ ID NO 16
<211> LENGTH: 534
<212> TYPE: PRT
<213> ORGANISM: Chlamydomonas reinhardtii

<400> SEQUENCE: 16

Thr Ala His Gly Lys Ala Ser Ala Thr Arg Glu Tyr Ala Gly Asp Phe
1               5                   10                  15

Leu Pro Gly Thr Thr Ile Ser His Ala Trp Ser Val Glu Arg Glu Thr
            20                  25                  30

```
His His Arg Tyr Arg Asn Pro Ala Glu Trp Ile Asn Glu Ala Ala Ile
         35                   40                  45

His Lys Ala Leu Glu Thr Ser Lys Ala Asp Ala Gln Asp Ala Gly Arg
 50                  55                  60

Val Arg Glu Ile Leu Ala Lys Ala Lys Glu Lys Ala Phe Val Thr Glu
 65                  70                  75                  80

His Ala Pro Val Asn Ala Glu Ser Lys Ser Glu Phe Val Gln Gly Leu
                 85                  90                  95

Thr Leu Glu Glu Cys Ala Thr Leu Ile Asn Val Asp Ser Asn Asn Val
            100                 105                 110

Glu Leu Met Asn Glu Ile Phe Asp Thr Ala Leu Ala Ile Lys Glu Arg
            115                 120                 125

Ile Tyr Gly Asn Arg Val Val Leu Phe Ala Pro Leu Tyr Ile Ala Asn
        130                 135                 140

His Cys Met Asn Thr Cys Thr Tyr Cys Ala Phe Arg Ser Ala Asn Lys
145                 150                 155                 160

Gly Met Glu Arg Ser Ile Leu Thr Asp Asp Leu Arg Glu Glu Val
                165                 170                 175

Ala Ala Leu Gln Arg Gln Gly His Arg Arg Ile Leu Ala Leu Thr Gly
            180                 185                 190

Glu His Pro Lys Tyr Thr Phe Asp Asn Phe Leu His Ala Val Asn Val
        195                 200                 205

Ile Ala Ser Val Lys Thr Glu Pro Glu Gly Ser Ile Arg Arg Ile Asn
        210                 215                 220

Val Glu Ile Pro Pro Leu Ser Val Ser Asp Met Arg Arg Leu Lys Asn
225                 230                 235                 240

Thr Asp Ser Val Gly Thr Phe Val Leu Phe Gln Glu Thr Tyr His Arg
                245                 250                 255

Asp Thr Phe Lys Val Met His Pro Ser Gly Pro Lys Ser Asp Phe Asp
            260                 265                 270

Phe Arg Val Leu Thr Gln Asp Arg Ala Met Arg Ala Gly Leu Asp Asp
        275                 280                 285

Val Gly Ile Gly Ala Leu Phe Gly Leu Tyr Asp Tyr Arg Tyr Glu Val
    290                 295                 300

Cys Ala Met Leu Met His Ser Glu His Leu Glu Arg Glu Tyr Asn Ala
305                 310                 315                 320

Gly Pro His Thr Ile Ser Val Pro Arg Met Arg Pro Ala Asp Gly Ser
                325                 330                 335

Glu Leu Ser Ile Ala Pro Pro Tyr Pro Val Asn Asp Ala Asp Phe Met
            340                 345                 350

Lys Leu Val Ala Val Leu Arg Ile Ala Val Pro Tyr Thr Gly Met Ile
        355                 360                 365

Leu Ser Thr Arg Glu Ser Pro Glu Met Arg Ser Ala Leu Leu Lys Cys
        370                 375                 380

Gly Met Ser Gln Met Ser Ala Gly Ser Arg Thr Asp Val Gly Ala Tyr
385                 390                 395                 400

His Lys Asp His Thr Leu Ser Glu Ala Asn Leu Ser Lys Leu Ala
                405                 410                 415

Gly Gln Phe Thr Leu Gln Asp Glu Arg Pro Thr Asn Glu Ile Val Lys
            420                 425                 430

Trp Leu Met Glu Glu Gly Tyr Val Pro Ser Trp Cys Thr Ala Cys Tyr
        435                 440                 445
```

-continued

```
Arg Gln Gly Arg Thr Gly Glu Asp Phe Met Asn Ile Cys Lys Ala Gly
    450                 455                 460

Asp Ile His Asp Phe Cys His Pro Asn Ser Leu Leu Thr Leu Gln Glu
465             470                 475                     480

Tyr Leu Met Asp Tyr Ala Asp Pro Asp Leu Arg Lys Lys Gly Glu Gln
            485                 490                 495

Val Ile Ala Arg Glu Met Gly Pro Asp Ala Ser Glu Pro Leu Ser Ala
            500                 505                 510

Gln Ser Arg Lys Arg Leu Glu Arg Lys Met Lys Gln Val Leu Glu Gly
        515                 520                 525

Glu His Asp Val Tyr Leu
    530
```